US006642368B1

(12) United States Patent
Yuan et al.

(10) Patent No.: US 6,642,368 B1
(45) Date of Patent: Nov. 4, 2003

(54) PROGRAMMED CELL DEATH AND CASPASE-12

(75) Inventors: Junying Yuan, Newton, MA (US); Nobuhiro Morishima, Saitama (JP)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 09/291,289

(22) Filed: Apr. 14, 1999

Related U.S. Application Data

(60) Provisional application No. 60/081,962, filed on Apr. 16, 1998.

(51) Int. Cl.[7] ............................................... C07H 21/02

(52) U.S. Cl. ..................... 536/23.1; 536/23.1; 435/226; 435/325; 435/219; 435/455

(58) Field of Search ............................... 435/325, 219, 435/455, 226; 536/23.1

(56) References Cited

U.S. PATENT DOCUMENTS

| 6,083,735 A | 7/2000 | Yuan et al. ................. 435/226 |
| 6,087,160 A | 7/2000 | Yuan et al. ............... 435/320.1 |
| 6,214,572 B1 | 4/2001 | Yuan et al. .................... 435/23 |
| 6,379,950 B1 | 4/2002 | Alnemri ................... 435/320.1 |
| 6,416,753 B1 | 7/2002 | Yuan et al. ................ 424/85.2 |

FOREIGN PATENT DOCUMENTS

WO  WO 95/00160  *  1/1995

OTHER PUBLICATIONS

Van de Craen et al., "Characterization of seven murine caspase family members", FEBS Letters, vol. 403, pp. 61–69, 1997.*

Alnemri, E.S. et al., "Human ICE/CED–3 Protease Nomenclature," Cell 87:171 (1996).

Barinaga, M. et al., "Cell Suicide: By ICE, Not Fire," Science 263:754–756 (1994).

Barr, P.J. and L.D. Tomei, "Apoptosis and Its Role in Human Disease," Bio/Technol. 12:487–493 (1994).

Duan, H. et al., "ICE–LAP3, a Novel Mammalian Homologue of the Caenorhabditis elegans Cell Death Protein Ced–3 Is Activated during Fas– and Tumor Necrosis Factor–induced Apoptosis," J. Biol. Chem. 271:1621–1625 (1996).

Ellis, R.E. et al., "Mechanisms and Functions of Cell Death," Annu. Rev. Cell Biol. 7:663–698 (1991).

Enari, M. et al., "Sequential activation of ICE–like and CPP32–like proteases furing Fas–mediated apoptosis," Nature 380:723–726 (1996).

Faucheu, C. et al., "A novel human protease similar to the interleukin–1β converting enzyme induces apoptosis in transfected cells," EMBO J. 14:1914–1922 (1995).

Fernandes–Alnemri, T. et al., "CPP32, a Novel Human Apoptotic Protein with Homology to Caenorhabditis elegans Cell Death Protein Ced–3 and Mammalian Interleukin–1β–converting Enzyme," J. Biol. Chem. 269:30761–30764 (1994).

Fernandes–Alnemri, T. et al., "In vitro activation on CPP32 and Mch3 and Mch4, a novel human apoptotic cysteine protease containing two FADD–like domains," Proc. Natl. Acad. Sci. USA 93:7464–7469 (1996).

Gagliardini, V. et al., "Prevention of Vertebrate Neuronal Death by the crmA Gene," Science 263:826–828 (1994).

Kuida, D. et al., "Altered Cytokine Export and Apoptosis in Mice Deficient in Interleukin–1β Converting Enzyme," Science 267:2000–2003 (1995).

Kuida, K. et al., "Decreased apoptosis in the brain and premature lethality in CPP32–deficient mice," Nature 384:368–372 (1996).

Kumar, S. et al., "Induction of apoptosis by the mouse Nedd2 gene, which encodes a protein similar to the product of the Caenorhabditis elegans cell death gene ced–3 and the mammalian IL–1β–converting enzyme," Genes & Develop. 8:1613–1626 (1994).

Li, P. et al., "Mice Deficient in IL–1β–Converting Enzyme Are Defective in Production of Mature IL–1β and Resistant to Endotoxic Shock," Cell 80:401–411 (1995).

Miura, M. et al., "Induction of Apoptosis in Fibroblasts by IL–1β–Converting Enzyme, a Mammalian Homolog of the C. elegans Cell Death Gene ced–3," Cell 75:653–660 (1993).

Munday, N.A. et al., "Molecular Cloning and Pro–apoptotic Activity of $ICE_{rel}II$ and $ICE_{rel}III$, Members of the ICE/CED–3 Family of Cysteine Proteases," J. Biol. Chem. 270:15870–15876 (1995).

Nett, M.A. et al., "Molecular Cloning of the Murine IL–1β Converting Enzyme cDNA," J. Immunol. 149:3254–3259 (1992).

Nicholson, D.W. et al., "Identification and inhibition of the ICE/CED–3 protease necessary for mammalian apoptosis," Nature 376:37–43 (1995).

Shi, L. et al., "Activation of an interleukin 1 converting enzyme–dependent apoptosis pathway by granzyme B," Proc. Natl. Acad. Sci. USA 93:11002–11007 (1996).

(List continued on next page.)

Primary Examiner—Karen Cochrane Carlson
Assistant Examiner—Hope A. Robinson
(74) Attorney, Agent, or Firm—Sterne, Kessler, Goldstein & Fox P.L.L.C.

(57) ABSTRACT

This invention relates to nucleic acids encoding caspase-12, proteins encoded by casp-12 nucleic acids, vectors, and hosts transformed with vectors. Caspase-12 is a member of the caspase family, which also includes mammalian interleukin-1β-converting enzyme (ICE). Caspases are thought to carry out the execution phase of apoptosis in a cascade of proteolytic events. The invention also relates to the use of caspase-12 to induce programmed cell death.

16 Claims, 15 Drawing Sheets

OTHER PUBLICATIONS

Stennicke, H.R. and G.S. Salvesen, "Biochemical Characteristics of Caspases–3, –6, –7, and –8," *J. Biol. Chem.* 272:25719–25723 (Oct. 1997).

Tewari, M. and V.M. Dixit, "Fas– and Tumor Necrosis Factor–induced Apoptosis Is Inhibited by the Poxvirus crmA Gene Product," *J. Biol. Chem.* 270:3255–3260 (1995).

Tewari, M. et al., "Yama/CPP32β, a Mammalian Homolog of CED–3, Is a CrmA–Inhibitable Protease That Cleaves the Death Substrate Poly(ADP–Ribose) Polymerase," *Cell* 81:801–809 (1995).

Thornberry, N.A. et al., "A novel heterodimeric cysteine protease is required for interleukin–1β processing in monocytes," *Nature* 356:768–774 (1992).

Van de Craen, M. et al., "Characterization of seven murine caspase family members," *FEBS Letters* 403:61–69 (Feb. 1997).

Walker, N.P.C. et al., "Crystal Structure of the Cysteine Protease Interleukin–1β–Converting Enzyme: A (p20/p10)$_2$ Homodimer," *Cell* 78:343–352 (1994).

Wang, L. et al., "Ich–1, an Ice/ced–3–Related Gene, Encodes Both Positive and Negative Regulators of Programmed Cell Death," *Cell* 78:739–750 (1994).

Wang, S. et al., "Identification and Characterization of Ich–3, a Member of the Interleukin–1β Converting Enzyme (ICE)/Ced–3 Family and an Upstream Regulator of ICE," *J. Biol. Chem.* 271:20580–20587 (1996).

Wang, S. et al., "Murine Caspase–11, an ICE–Interacting Protease, Is Essential for the Activation of ICE," *Cell* 92:501–509 (Feb. 1998).

Wilson, K.P. et al., "Structure and mechanism of interleukin–1β converting enzyme," *Nature* 370:270–275 (1994).

Xue, D. et al., "The *Caenorhabditis elegans* cell–death protein CED–3 is a cysteine protease with substrate specificities similar to those of the human CPP32 protease," *Genes & Develop.* 10:1073–1083 (1996).

Yuan, J. et al., "The *C. elegans* Cell Death Gene ced–3 Encodes a Protein Similar to Mammalian Interleukin–1β–Converting Enzyme," *Cell* 75:641–652 (1993).

Database Medline on Dialog, US National Library of Medicine (Bethesda, MD), Swiss–Prot37 Accession No. 008736, Caspase–12 precursor (ED 3.4.22) from Mus musculus, Nov. 1, 1997. See especially amino acids 87–419 which comprise SEQ ID NO:14 with the exception of 1 conservative substitution at position 17 of SEQ ID NO:14. Published in *FEBS Letters* 403:61–69 (Feb. 1997).

Database Medline on Dialog, US National Library of Medicine, (Bethesda, MD) GenEmb1 Accession No. Y13090, Caspase–12, cysteine protease from mouse, May 27, 1997. See especially nucleic acids 291–1293 which comprise SEQ ID NO:3 with the exception of 2 mismatches. Published in *FEBS Letters* 403:61–69 (Feb. 1997).

Database Medline on Dialog, US National Library of Medicine (Bethesda, MD), Swiss–Prot37 Accession No. 008736, Caspase–12 precursor (EC 3.4.22) from Mouse, Nov. 1, 1997. See especially amino acids 145–419 which comprise amino acids 145–419 of SEQ ID NO:2. Published in *FEBS Letters* 403:61–69 (Feb. 1997).

Database Medline on Dialog, US National Library of Medicine, (Bethesda, MD) GenEmb1 Accession No. Y13090, Caspase–12, cysteine protease from mouse, May 27, 1997. See especially nucleic acids 466–1290 which encode amino acids 145–419 of SEQ ID NO:2. Published in *FEBS Letters* 403:61–69 (Feb. 1997).

Database Medline on Dialog, US National Library of Medicine, (Bethesda, MD) GenEmb1 Accession No. Y13090, Caspase–12, cysteine protease from mouse, May 27, 1997. See especially nucleic acids 316–1290 which encode amino acids 95–419 SEQ ID NO:2. Published in *FEBS Letters* 403:61–69 (Feb. 1997).

Database Medline on Dialog, US National Library of Medicine (Bethesda, MD), Swiss–Prot37 Accession No. 008736, Caspase–12 Precursor (EC 3.4.22) from Mouse. See especially amino acids 95–419 which comprise amino acids 95–419 of SEQ ID NO:2. Published in *FEBS Letters* 403:61–69 (Feb. 1997).

Pending Non–Provisional U.S. patent application 08/459,455, Yuan et al., filed Jun. 2, 1995 (Not published).

Pending Non–Provisional U.S. patent application 09/549,066, Yuan et al., filed Apr. 13, 2000 (Not published).

\* cited by examiner

```
CTTTTTTTTT TTTTTTTTTT TATGTCCTGG AGTCCTGCAC AGCCATGGCG GCCAGGAGGA CACATGAAAG AGATCCAATC    80
                ↓                              M  A  A  R  R  T  H  E  R  D  P  I
TACAAGATCA AAGGTTTGGC CAAGGACATG CTGGATGGGG TTTTTGATGA CCTGGTGGAG AAGAATGTTT TAAATGGAGA   160
 Y  K  I  K  G  L  A  K  D  M  L  D  G  V  F  D  D  L  V  E  K  N  V  L  N  G  D
TGAGTTACTC AAAATAGGGG AAAGTGCGAG TTTCATCCTG AACAAGGCTG AGAATCTGGT TGAGAACTTC TTAGAGAAAA   240
 E  L  L  K  I  G  E  S  A  S  F  I  L  N  K  A  E  N  L  V  E  N  F  L  E  K  T
CAGACATGGC AGGAAAAATA TTTGCTGGCC ACATTGCCAA TTCCCAGGAA CAGCTGAGTT TACAATTTTC TAATGATGAG   320
 D  M  A  G  K  I  F  A  G  H  I  A  N  S  Q  E  Q  L  S  L  Q  F  S  N  D  E
GATGATGGAC CTCAGAAGAT ATGTACACCT TCTTCTCCAT CAGAATCCAA GAGAAAAGTA GAGGATGATG AAATGGAGGT   400
 D  D  G  P  Q  K  I  C  T  P  S  S  P  S  E  S  K  R  K  V  E  D  D  E  M  E  V
AAATGCTGGA TTGGCCCATG AATCACATCT AATGCTGACA GCTCCTCATG GACTCCAGAG CTCAGAAGTC CAAGATACAC   480
 N  A  G  L  A  H  E  S  H  L  M  L  T  A  P  H  G  L  Q  S  S  E  V  Q  D  T  L
TGAAGCTTTG TCCACGTGAT CAGTTTTGTA AGATAAAGAC AGAAAGGGCA AAAGAGATAT ATCCAGTGAT GGAGAAGGAG   560
 K  L  C  P  R  D  Q  F  C  K  I  K  T  E  R  A  K  E  I  Y  P  V  M  E  K  E
GGACGAACAC GTCTGGCTCT CATCATCTGC AACAAAAAGT TTGACTACCT TTTTGATAGA GATAATGCTG ATACTGACAT   640
 G  R  T  R  L  A  L  I  I  C  N  K  K  F  D  Y  L  F  D  R  D  N  A  D  T  D  I
TTTGAACATG CAAGAACTAC TTGAAAATCT TGGATACTCT GTGGTGTTAA AGAAAAACCT TACAGCTCAG GAAATGGAGA   720
 L  N  M  Q  E  L  L  E  N  L  G  Y  S  V  V  L  K  E  N  L  T  A  Q  E  M  E  T
CAGAGTTAAT GCAGTTTGCT GGCCGTCCAG AGCACCAGTC CTCAGACAGC ACATTCCTGG TGTTTATGTC CCATGGCATC   800
 E  L  M  Q  F  A  G  R  P  E  H  Q  S  S  D  S  T  F  L  V  F  M  S  H  G  I
CTGGAAGGAA TCTGTGGGGT GAAGCACCGA AACAAAAAGC CAGATGTTCT TCATGATGAC ACTATCTTCA AAATTTTCAA   880
 L  E  G  I  C  G  V  K  H  R  N  K  K  P  D  V  L  H  D  D  T  I  F  K  I  F  N
CAACTCTAAC TGTCGGAGTC TGAGAAACAA ACCCAAGATT CTCATCATGC AGGCCTGCAG AGGCAGATAT AATGGAACTA   960
 N  S  N  C  R  S  L  R  N  K  P  K  I  L  I  M  Q  A  C  R  G  R  Y  N  G  T  I
TTTGGGTATC CACAAACAAA GGGATAGCCA CTGCTGATAC AGATGAGGAA CGTGTGTTGA GCTGTAAATG GAATAATAGT  1040
 W  V  S  T  N  K  G  I  A  T  A  D  T  D  E  E  R  V  L  S  C  K  W  N  N  S
ATAACAAAGG CCCATGTGGA GACAGATTTC ATTGCTTTCA AATCTTCTAC CCCACATAAT ATTTCTTGGA AGGTAGGCAA  1120
 I  T  K  A  H  V  E  T  D  F  I  A  F  K  S  S  T  P  H  N  I  S  W  K  V  G  K
GACTGGTTCC CTCTTCATTT CCAAACTCAT TGACTGCTTC AAAAAGTACT GTTGGTGTTA TCATTTGGAG GAAATTTTTC  1200
 T  G  S  L  F  I  S  K  L  I  D  C  F  K  K  Y  C  W  C  Y  H  L  E  E  I  F  R
GAAAGGTTCA ACACTCATTT GAGGTCCCAG GTGAACTGAC CCAGATGCCC ACTATTGAGA GAGTATCCAT GACACGCTAT  1280
 K  V  Q  H  S  F  E  V  P  G  E  L  T  Q  M  P  T  I  E  R  V  S  M  T  R  Y
TTCTACCTTT TTCCCGGGAA TTAGCACAGG CAACTCTCAT GCAGTTCACA GTCAAGTATT GCTGTAGCTG AGAAGAAAAG  1360
 F  Y  L  F  P  G  N  ***
AAAAATTCCAA GATCCCAGGA TTTTTAAATG TGTAAAACTT TT                                          1402
```

```
caspase-5                                                             -MF KGILQSGLDN FVINHMLKNN VAGQTSIQTL VPNTDQKSTS    42
Caspase-12  MAARRTHERD PIYKIKGLAK DML-------- ---------- -------DGVF DDLVEKNVLN GDELLKIGES ASFILNKAEN LVENFLEKTD    67
hICE        MADKVLKEKR KLFIRSMGEG TI-------- ---------- -------NGLL DELLQTRVLN KEEMEKVKRE NATVMDKTRA LIDSVIPKGA    66
mICE        MADKILRAKR KQFINSVSIG TI-------- ---------- -------NGLL DELLEKRVLN QEEMDKIKLA NITAMDKARD LCDHVSKKGA    66
caspase-11  MAENKHPDKP LKVLEQLGKE VL-------- ---------- -------TEYL EKLVQSNVLK LKEEDKQKFN NAERSDKRMV FVDAMKKKHS    66
caspase-4   MAEGNHRKKP LKVLESLGKD FL-------- ---------- -------TGVL DNLVEQNVLN WKKEEKKKYY DAKTEDKVRA MADSMQEKQR    66
caspase-5   VKKDNHKKKT VKMLEYLGKD VL-------- ---------- -------HGVF MYLAKHDVLT LKEEEKKKYY DAKTEDKALI LVDSLR-KNR   107
caspase-2   MAADRGRRIL GVCGMPHPHQ ETLKKNRVVL AKQLLLSELL EHLLEKDIIT LE-MRELIQA KVGSFSQNVE LLNLLPKRGP    79
caspase-3                                                                                                         0
CED-3       MMRQDRRSLL ERNIMMFSSH ---------- ---------- -LKVDEIL EVLIAKQVLN SDNGDMI-NS CCGTVREKRRE IVKAVQRRGB    66

12 MAGKIFAGHI ANSQEQLSLQ FSN------- ---------- ---------- ---------- ---------- ----------    90
       hICE QACQICITYI CEEDSYLAGT LGL------- ---------- ---------- ---------- ---------- ----------    89
       mICE PASQIFITYI CNEDCYLAGI LEL------- ---------- ---------- ---------- ---------- ----------    89
         11 KVGEMLL--- ---------- ---------- ---------- ---------- ---------- ---------- ----------    73
          4 MAGQMLL--- ---------- ---------- ---------- ---------- ---------- ---------- ----------    73
          5 VAHQMFT--- ---------- ---------- ---------- ---------- ---------- ---------- ----------   114
          2 QAFDAFCEAL RETKQGHLED MLL------- ---------- ---------- ---------- ---------- ----------   102
          3 ---------- ---------- ---------- ---------- ---------- ---------- ---------- ----------     0
       CED-3 VAFDAFYDAL RSTGHEGLAE VLEPLARSVD SNAVEFECPM SPASHRRSRA LSPAGYTSPT RVHRDSVSSV SSFTSYQDIY   146

12 ------D EDDGPQKICT PSSPSESKRK VEDDEMEVNA GLAHESHLML TAPHGLQSSE VQDTLKLCPR DQFCKIKTER   161
       hICE ------SADQ TSGNYLNMQD SQGVLSSFPA PQAVQDN--- --PAMPTSSG SEGNVKLCSL EEAQRIWKQK   148
       mICE ------QSAP SAETFVATED SKGGHPSSSE TKE-EQN--- --KEDGTFPG LTGTLKFCPL EKAQKLWKEN   147
         11 -------QTFFSVDP G-----SHHG EANLEME--- ----EPKK SLMTLKLCSP EEFTRLCREK   117
          4 -------QTFFNIDQ I------SPNK KAHPNME--- ----AGPPESGE STDALKLCPH EEFLRLCKER   121
          5 -------QTLLNMDQ K------ITSV KPLLQID--- ----AGPPESAE STNILKLCPR EEFLRLCKKN   162
          2 TILSGLQHVL PPLSCDYDLS LPFPVCESCP LYKKLRLSTD TVEHSLDNKD GPVCLQVKPC TPEFYQTHF-   171
          3 ------ME NTENSVDSKS IKNLEPKIIH GSESMDSGI- SLDNSY                                37
       CED-3 SRARSRSRSR ALHSSDRHNY SSPPVNAFPS QPSSANSSFT GCSSLGYSS- SRNRSFSKAS GPTQYIFHEE DMNFVDAPTI   225
```

FIG. 2B

```
   12 A-----KEIY PVMEKEGRTR LALIICNKKF ---DYLFDRD NADTDILNMQ ELLENLGYSV VL  KENLTA QEMETELMQF 231
 hICE S-----AEIY PIMDKSSRTR LALIICNEEF ---DSIPRRT GAEVDITGMT MLLQNLGYSV DV--KKNLTA SDMITELEAF 218
 mICE P-----SEIY PIMNTTTRTR LALIICNTEF ---QHLSPRV GAQVDLREMK LLEDLGYTV  KV--KENLTA LEMVKEVKEF 217
   11 T-----QEIY PIKEANGRTR KALIICNTEF ---KHLSLRY GAKFDIIGMK GLLEDLGYDV VV--KENLTA EGMESEMKDF 187
    4 A-----EEIY PIKERNNRTR LALIICNTEF ---DHLPPRN GADFDITGMK ELLLLEGLDY SVDVEENLTA RDMESALRAF 193
    5 H-----DEIY PIKKREDRRR LALIICNTKF ---DHLPARN GAHYDIVGMK RLLQGLGYTV VD--EKNLTA RDMESVLRAF 232
    2 ------QLAY R LQSRPRG- LALVLSNVHF TGEKELEFRS GGDVDHSTLV TLFKLLGYDV HV--LCDQTA QEMQEKLQNF 241
    3 ------KMDY PE------MG LCIIINNKNF HKSTGNTSRS GIDVDAANLR ETFRNLKYEV RN--KNDLTR KEIVELMRDV 103
CED 3 SRVFDEKTMY R-NFSSPRG- MCLIINNEHF ---EQMPTRN GTKADKDNLT NLFRCMGYTV IC--KDNLTG RGMLLTIRDF 298

12 AGRPEHQSSD STFLVFMSHG ILEGICGVKH RNKKPDVLHD DTIFKIFNNS NCRSLRNKPK ILIMQACRGR YNGTIWVSTN 311
 hICE AHRPEHKTSD STFLVFMSHG IREGICGKKH SEQVPDILQL MAIFNMLNTK NCPSLKDKPK VIIIQACRGD SPGVVWFKDS 298
 mICE AACPEHKTSD STFLVFMSHG IQEGICGTTY SNEVSDILKV DTIFQMMNTL KCPSLKDKPK VIIIQACRGE KQCVVLLKDS 297
   11 AALSEHQTSD STFLVLMSHG TLHGICGTMH SEKTPDVLQY DTIYQIFNNC HCPGLRDKPK VIIVQACRGG NSGEMWIRES 267
    4 ATRPEHKSSD STFLVLMSHG ILEGICGTVH DEKKPDVLLY DTIFQIFNNR NCLSLKDKPK VIIVQACRGA NRGELWVRDS 273
    5 AARPEHKSSD STFLVLMSHG ILEGICGTAH KKKKPDVLLY DTIFQIFNNR NCLSLKDKPK VIIVQACRGE KHGELWVRDS 312
    2 AQLPAHRVTD SCIVALLSHG VEGAIYGV-- ---DGKLLLQL QEVFQLFDNA NCPSLQNKPK MFFIQACRGD ETDRGVDQQD 316
    3 SK-EDHSKRS SFVCVLLSHG KEGIIFGT-- -----NGPVDL KKITNFFRGD RCRSLTGKPK LFIIQACRGT ELDCGIETDS 176
CED-3 AK--HESHGD SAILVILSHG KENVIIGV-- ---DDIPIST HEIYDLLNAA NAPRLANKPK IVFVQACRGE RRDNGFPVLD 371

12 KGIATADTDE ERVLSCKWMNN SIT------- ------KAHV ETDFIAFKSS TPHNISWKVG KTGSLFISKL IDCFKKYCWC 378
 hICE VGVSGNLSLP TTEEFE--DD AIK------- -------KAHI EKDFIAFCSS TPDNVSWRHP TMGSVFIGRL IGHMQEYACS 363
 mICE VRDSEE-DFL TDAIFE--DD GIK------- -------KAHI EKDFIAFCSS TPDNVSWRHP VRGSLFIESL IKHMKEYAWS 361
   11 SKPQLCRGVD LPRNME--AD AVK------- ------LSHV EKDFIAFYST TPHHLSYRDK TGGSYFITRL ISCFRKHACS 332
    4 PASLEVASSQ SSENLE--ED AVY------- ------KTHV EKDFIAFCSS TPHNVSWRDS TMGSIFITQL ITCFQKYSWC 338
    5 PASLAVISSQ SSENLE--AD SVC------- ------KIHE EKDFIAFCSS SPHNVSWRDR TRGSIFITEL ITCFQKYSCC 377
    2 GKNHAGSPGC EESDAGKEKL PKM------- -------RLPT RSDMICGYAC LKGTAAMRNT KRGSWYIEAL AQVFSERACD 383
    3 GVDDDMAC-- ---------- ---------- ---------- HKIPV EADFLYAYST APGYYSWRNS TAQYSVSWRNS CAMLKQYADK 229
CED-3 SVDGVPAFLR RGMDNRDGPL FNFLGCVRPQ VQQWRKKPS QADILIAYAT TAQYSVSWRNS ARGSWFIQAV CEVFSTHAKD 451
```

```
12    YHLEEIFRKV QHSFEVPGE- ---------- -L TQMPTIERVS MTRYFYLFPG N   419
hICE  CDVEEIFRKV RFSFEQPDG- ---------- -R AQMPTTERVT LTRCFYLFPG H   404
mICE  CDLEDIFRKV RFSFEQPKF- ---------- -R LQMPTADRVT LTKRFYLFPG H   402
11    CHLFDIFLKV QQSFEKASI- ---------- -H SQMPTIDRAT LTRYFYLFPG N   373
4     CHLEEVFRKV QQSFETPRA- ---------- -K AQMPTIERLS MTRYFYLFPG N   379
5     CHLMEIFRKV QKSFEVPQA- ---------- -K AQMPTIERAT LTRDFYLFPG N   418
2     MHVADMLVKV NALIKDREG- YAPGTEFHRC KEMS-EYCST LCRHLYLFPG HPPT    435
3     LEFMHILTRV NRKVATEFES FSFDATFHAK KQIP-CIVSM LTKELYFYH          277
CED-3 MDVVELLTEV NKKVACGFQT SQGSNIL--- KQMP-EMTSR LLKKFYFWPE ARNSAV 503
```

FIG. 2C

```
ATG GCG GCC AGG AGG ACA CAT GAA AGA GAT CCA ATC TAC AAG ATC AAA    48
 M   A   A   R   R   T   H   E   R   D   P   I   Y   K   I   K
GAA TTT TCT AAT GAT GAG GAT GAT GGA CCT CAG AAG ATA TGT ACA CCT    96
 E   F   S   N   D   E   D   D   G   P   Q   K   I   C   T   P
TCT TCT CCA TCA GAA TCC AAG AGA AAA GTA GAG GAT GAT GAA ATG GAG   144
 S   S   P   S   E   S   K   R   K   V   E   D   D   E   M   E
GTA AAT GCT GGA TTG GCC CAT GAA TCA CAT CTA ATG CTG ACA GCT CCT   192
 V   N   A   G   L   A   H   E   S   H   L   M   L   T   A   P
CAT GGA CTC CAG AGC TCA GAA GTC CAA GAT ACA CTG AAG CTT TGT CCA   240
 H   G   L   Q   S   S   E   V   Q   D   T   L   K   L   C   P
CGT GAT CAG TTT TGT AAG ATA AAG ACA GAA AGG GCA AAA GAG ATA TAT   288
 R   D   Q   F   C   K   I   K   T   E   R   A   K   E   I   Y
CCA GTG ATG GAG AAG GAG GGA CGA ACA CGT CTG GCT CTC ATC ATC TGC   336
 P   V   M   E   K   E   G   R   T   R   L   A   L   I   I   C
AAC AAA AAG TTT GAC TAC CTT TTT GAT AGA GAT AAT GCT GAT ACT GAC   384
 N   K   K   F   D   Y   L   F   D   R   D   N   A   D   T   D
ATT TTG AAC ATG CAA GAA CTA CTT GAA AAT CTT GGA TAC TCT GTG GTG   432
 I   L   N   M   Q   E   L   L   E   N   L   G   Y   S   V   V
TTA AAA GAA AAC CTT ACA GCT CAG GAA ATG GAG ACA GAG TTA ATG CAG   480
 L   K   E   N   L   T   A   Q   E   M   E   T   E   L   M   Q
TTT GCT GGC CGT CCA GAG CAC CAG TCC TCA GAC AGC ACA TTC CTG GTG   528
 F   A   G   R   P   E   H   Q   S   S   D   S   T   F   L   V
TTT ATG TCC CAT GGC ATC CTG GAA GGA ATC TGT GGG GTG AAG CAC CGA   576
 F   M   S   H   G   I   L   E   G   I   C   G   V   K   H   R
AAC AAA AAG CCA GAT GTT CTT CAT GAT GAC ACT ATC TTC AAA ATT TTC   624
 N   K   K   P   D   V   L   H   D   D   T   I   F   K   I   F
AAC AAC TCT AAC TGT CGG AGT CTG AGA AAC AAA CCC AAG ATT CTC ATC   672
 N   N   S   N   C   R   S   L   R   N   K   P   K   I   L   I
ATG CAG GCC TGC AGA GGC AGA TAT AAT GGA ACT ATT TGG GTA TCC ACA   720
 M   Q   A   C   R   G   R   Y   N   G   T   I   W   V   S   T
AAC AAA GGG ATA GCC ACT GCT GAT ACA GAT GAG GAA CGT GTG TTG AGC   768
 N   K   G   I   A   T   A   D   T   D   E   E   R   V   L   S
TGT AAA TGG AAT AAT AGT ATA ACA AAG GCC CAT GTG GAG ACA GAT TTC   816
 C   K   W   N   N   S   I   T   K   A   H   V   E   T   D   F
ATT GCT TTC AAA TCT TCT ACC CCA CAT AAT ATT TCT TGG AAG GTA GGC   864
 I   A   F   K   S   S   T   P   H   N   I   S   W   K   V   G
AAG ACT GGT TCC CTC TTC ATT TCC AAA CTC ATT GAC TGC TTC AAA AAG   912
 K   T   G   S   L   F   I   S   K   L   I   D   C   F   K   K
TAC TGT TGG TGT TAT CAT TTG GAG GAA ATT TTT CGA AAG GTT CAA CAC   960
 Y   C   W   C   Y   H   L   E   E   I   F   R   K   V   Q   H
TCA TTT GAG GTC CCA GGT GAA CTG ACC CAG ATG CCC ACT ATT GAG AGA  1008
 S   F   E   V   P   G   E   L   T   Q   M   P   T   I   E   R
GTA TCC ATG ACA CGC TAT TTC TAC CTT TTT CCC GGG AAT TAG          1050
 V   S   M   T   R   Y   F   Y   L   F   P   G   N
```

FIG.9

PROGRAMMED CELL DEATH AND CASPASE-12

This application claims the benefit of the filing date of U.S. Provisional Application No. 60/081,962, filed Apr. 16, 1998 and is incorporated herein by reference.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds. The U.S. Government has certain rights in this invention.

BACKGROUND OF THE INVENTION

1. Field of the Invention

This invention is generally in the field of molecular biology. This invention relates to the control of programmed cell death.

2. Related Art

Programmed Cell Death

Apoptosis, also referred to as programmed cell death or regulated cell death, is a process by which organisms eliminate unwanted cells. Such cell death occurs as a normal aspect of animal development as well as in tissue homeostasis, such as in tissue remodeling and the establishment of immune self-tolerance, during aging and in disease (Raff, M. C., *Nature* 356:397–400 (1992); Glucksmann, A., *Biol. Rev. Cambridge Philos. Soc.* 26:59–86 (1950); Ellis et al., *Dev.* 112:591–603 (1991); Vaux et al., *Cell* 76:777–779 (1994); Thompson, C. B., *Science* 267:1456–1462 (1995)). Programmed cell death can also act to regulate cell number, to facilitate morphogenesis, to remove harmful or otherwise abnormal cells and to eliminate cells that have already performed their function. Additionally, programmed cell death is believed to occur in response to various physiological stresses such as hypoxia or ischemia. The morphological characteristics of apoptosis include plasma membrane blebbing, condensation of nucleoplasm and cytoplasm and degradation of chromosomal DNA at inter-nucleosomal intervals. (Wyllie, A. H., in *Cell Death in Biology and Pathology*, Bowen and Lockshin, eds., Chapman and Hall (1981), pp. 9–34).

Apoptosis is achieved through an endogenous mechanism of cellular suicide (Wyllie, A. H., in *Cell Death in Biology and Pathology*, Bowen and Lockshin, eds., Chapman and Hall (1981), pp. 9–34) and occurs when a cell activates its internally encoded suicide program as a result of either internal or external signals. The suicide program is executed through the activation of a carefully regulated genetic program (Wylie, A. H., et al., *Int. Rev. Cyt.* 68: 251 (1980); Ellis, R. E., et al., *Ann. Rev. Cell Bio.* 7: 663 (1991); Yuan, Y. *Curr. Op. Cell. Biol.* 7:211–214 (1995)). In many cases, gene expression appears to be required for apoptosis, since cell death can be prevented by inhibitors of RNA or protein synthesis (Cohen et al., *J. Immunol.* 32:38–42 (1984); Stanisic et al., *Invest. Urol.* 16:19–22 (1978); Martin et al., *J. Cell Biol.* 106:829–844 (1988).

Acute and chronic disregulation of cell death is believed to lead to a number of major human diseases (Barr et al. *Biotech.* 12:487–493 (1995); Thompson C. B., *Science* 267:14561462 (1995)). These diseases include but are not limited to malignant and pre-malignant conditions, neurological and neurodegenerative disorders, heart disease, immune system disorders, intestinal disorders, kidney disease, aging, viral infections and AIDS.

Malignant and pre-malignant conditions may include solid tumors, B cell lymphomas, chronic lymphocytic leukemia, prostate hypertrophy, preneoplastic liver foci and resistance to chemotherapy. Neurological disorders may include stroke, Alzheimer's disease, amyotrophic lateral sclerosis, prion-associated disorder and ataxia telangiectasia. Heart disease may include ischemic cardiac damage and chemotherapy-induced myocardial damage. Immune system disorders may include AIDS, type I diabetes, lupus erythematosus, Sjogren's syndrome and glomerulonephritis. Intestinal disorder may include dysentery, inflammatory bowel disease and radiation- and HIV-induced diarrhea. Kidney disease may include polycystic kidney disease and anemia/erythropoiesis. Specific references to many of these pathophysiological conditions as involving disregulated apoptosis can be found in Barr et al. Id.-Table I.

Caspases

Caspases are a family of proteins, previously referred to as ICE or ced-3 proteins, involved in the regulation of apoptosis. A genetic pathway of programmed cell death has been identified in the nematode *Caenorhabditis elegans* (Ellis, R. E., et al., *Annual Review of Cell Biology* 7:663–698 (1991).) In this genetic pathway, the genes ced-3 and ced-4 are required for cell death, while another gene, ced-9, is a negative regulator of cell death. The ced-3 gene encodes a cysteine protease (Yuan, J., et al., *Cell* 75:641–652 (1993)) which shares sequence similarity to the mammalian interleukin-1β-converting enzyme (ICE), also called caspase-1, which catalyzes the processing of pro-interleukin-1β to its biologically active form (Thornberry, N. A., et al., *Nature* 356:768–774 (1992)). The active centers of ICE and Ced-3 are remarkably conserved with an identical pentapeptide QACRG (SEQ ID NO:3) in which the cysteine is the catalytic residue (Yuan, J., et al., *Cell* 75:641–652 (1993); Thornberry, N. A., et al., *Nature* 356:768–774 (1992)). ICE and Ced-3 exhibit unique requirement for Asp at P1 position for cleavage with different preference for P2–P4 positions in their substrates (Thornberry, N. A., et al., *Nature* 356:768–774 (1992); Xue, D., et al., *Genes and Development* 10:1073–1083 (1996)). The ICE/Ced-3 family of cysteine proteases have recently been renamed as caspases (Alnemri, E. S., et al., *Cell* 87:171 (1996)), which stands for cysteine aspartic acid specific proteases. There have been at least ten human caspases identified (Stennicke, H. R. and Salvesen, G. S., *J. Biol. Chem.* 272(41):25719–25723 (1997)).

Overexpression of ICE in a rat fibroblast cell line results in apoptosis, which can be blocked by mammalian Bcl-2, a homolog of the nematode cell death suppressor, Ced-9 (Miura, M., et al., *Cell* 75:653–660 (1993)). While Ced-3 is the only caspase identified in *C. elegans*, at least twelve caspases have been identified in mammals (Kumar, S., et al., *Genes and Development* 8:1613–1626 (1994); Wang, L., et al., *Cell* 78:739–750 (1994); Femandez-Alnemri, T., et al., *J. Biol. Chem.* 269:30761–30764 (1994); Tewari, M., *Cell* 81:801–809 (1995); Faucheu, C., et al., *The EMBO Journal* 14:1914–1922 (1995); Munday, N. A., et al., *J. Biol. Chem.* 270:15870–15876 (1995); Duan, H., et al., *J. Biol. Chem.* 271:1621–1625 (1996); Wang, S., et al., *J. Biol. Chem.* 271:20580–20587(1996); Van de Craen, M., et al., *FEBS Letters* 403:61–69 (1997)).

The members of the caspase family are expressed in multiple tissues and cell types during development and adult life. Thus, unlike that in *C. elegans* where a single ced-3 gene controls all programmed cell death, multiple homologs of CED-3 regulate mammalian apoptosis. Interesting results have come from gene knockout experiments where mice that are mutant for ICE and caspase-3 have been generated (Li, P., et al., *Cell* 80:401–411 (1995); Kuida, K., et al., *Science* 267:2000–2003 (1995); Kuida, K., et al., *Nature* 384:368–372 (1996)). The results emerging from analyses of these mutant mice support the hypothesis that these homologs act in both parallel and sequential fashion to regulate apoptosis (Enari, M., et al., *Nature* 380:723–725 (1996)). Ice–/– embryonic fibroblasts and B lymphoblasts are resistant to granzyme B-induced apoptosis (Shi, L., et al., *Proc. Natl. Acad. Sci. US A* 93:11002–11007 (1996)). Caspase-3–/– mutant mice are defective in brain development, exhibiting a variety of hyperplasias and disorganizations which may be due to the absence of apoptosis, although their thymocytes respond normally to a variety of apoptotic agents (Kuida, K., et al., *Nature* 384:368–372 (1996)). These results suggest that either ICE or caspase-3 is critical for certain types of apoptosis in certain cells while their functions in other cell types are redundant.

Inhibitors of the caspase family prevent apoptosis induced by a variety of signals such as trophic factor deprivation, Fas and TNF, suggesting that the members of the caspase family are critical regulators of mammalian apoptosis (Miura, M., et al., *Cell* 75:653–660 (1993); Gagliardini, V., et al., *Science* 263:97–100 (1994); Tewari, M., and Dixit, V. M., *J. Biol. Chem.* 270:3255–3260 (1995)). Since cells have been found to express multiple caspases (Wang, L., et al., *Cell* 78:739–750 (1994)), it is proposed that caspases may act in a proteolytic cascade to carry out the execution of cells (Enari, M., et al., *Nature* 380:723–725 (1996)). Caspases are synthesized as proforms which are to be activated through cleavages after specific Asp residues during activation process. For example, active ICE is generated from its 45 kDa precursor protein through specific cleavages at four Asp residues, which give rise to the 20 kDa (p20) and 10 kDa (p10) subunits.

The unique specificity of the caspase family suggests that either autoprocessing or cleavage by other homologs is responsible for the activation of the proforms. In vitro, pro-ICE can be activated by active caspase-4 (Faucheu, C., et al., *The EMBO Journal* 14:1914–1922 (1995)), pro-caspase-3 by active ICE (Tewari, M., *Cell* 81:801–809 (1995); Nicholson, D. W., et al., *Nature* 376:37–43 (1995)) and pro-caspase-3 and pro-caspase-7 by active caspase-10 (Fernandes-Alnemri. T., et al., *Proc. Natl. Acad. Sci. USA* 93:7464–7469 (1996)). In apoptosis induced by anti-Fas antibody, a transient increase in ICE-like activity was detected prior to an elevation in caspase-3-like activity, supporting the idea that the caspase family of proteases act in a proteolytic cascade (Enari, M., et al., *Nature* 380:723–725 (1996)).

SUMMARY OF THE INVENTION

In the present invention, the gene encoding caspase-12, (casp-12—previously referred to as Ich-4), was isolated through degenerate polymerase chain reaction and sequenced. Casp-12 has at least two alternative splicing products, casp-12S and casp-12L. Casp-12L contains an open reading frame of 419 amino acid residues. Casp-12S contains an open reading frame of 349 amino acid residues. Fragments of caspase-12 were also obtained: casp-12Δ, consisting of the open reading frame for amino acid residues 95–419 of casp-12L; and casp-12Δ2, consisting of the open reading frame for amino acid residues 145–419 of casp-12L.

This invention is thus directed, inter alia, to isolated nucleic acid molecules comprising a nucleotide sequence encoding the amino acid sequence of caspase-12S as shown in FIG. 9 (SEQ ID NO:14) or as encoded by the cDNA clone contained in ATCC Deposit No. 209710. The invention is also directed to isolated nucleic acid molecules comprising the nucleotide sequence of caspase-12S as shown in FIG. 9 (SEQ ID NO: 13); nucleic acid molecules comprising a nucleotide sequence encoding caspase-12Δ (amino acid residues 95 to 419 of SEQ ID NO:2); and nucleic acid molecules comprising a nucleotide sequence encoding caspase-12Δ2 (amino acid residues 145 to 419 of SEQ ID NO:2). The invention is also directed to nucleic acid molecules comprising a nucleotide sequence complementary to the above-described sequences.

Also provided for are nucleic acid molecules at least 80%, preferably 85% or 90%, still more preferably 95%, 96%, 97%, 98%, or 99% identical to any of the above-described nucleic acid molecules. Also provided for are nucleic acid molecules which hybridize under stringent conditions to any of the above-described nucleic acid molecules.

The present invention also provides for recombinant vectors comprising an above-described nucleic acid molecule, and host cells transformed with such vectors.

Also provided are isolated polypeptides comprising the amino acid sequence of caspase-12S as shown in FIG. 9 (SEQ ID NO: 14) or as encoded by the cDNA clone contained in ATCC Deposit No. 209710, as well as polypeptides comprising the amino acid sequence of caspase-12Δ (amino acid residues 95 to 419 of SEQ ID NO:2) and polypeptides comprising the amino acid sequence of caspase-12Δ2 (amino acid residues 145 to 419 of SEQ ID NO:2). Also provided are polypeptides at least 80%, more preferably 85% or 90%, still more preferably 95%, 96%, 97%, 98%, or 99% identical to any of the above-described polypeptides.

Also provided are methods for inducing programmed cell death in a cell comprising contacting the cell with an above-described polypeptide.

Overexpression of casp-12L, casp-12S, and casp-12Δ in rat fibroblast cells caused apoptosis. The apoptotic activity of caspase-12 was not inhibitable by CrmA, a serpin encoded by cowpox virus which is a specific inhibitor of ICE, by Bcl-2, a mammalian cell death suppressor. The pro-caspase-12 protein was cleaved effectively by several other members of the caspase family in vitro, while recombinant caspase-12 protein and fragments thereof poorly cleaved other caspases except pro-caspase-12 itself. Therefore, the invention provides for a method of modulating apoptosis comprising contacting a cell with the protein encoded for by casp-12L, casp-12S, casp-12Δ or casp-12Δ2.

BRIEF DESCRIPTION OF THE FIGURES

FIGS. 1A–1B. caspase-12 cDNA. FIG. 1A shows the cDNA sequence (SEQ ID NO:1) and deduced amino acid sequence (SEQ ID NO:2) of caspase-12. Horizontal arrows indicate the position of degenerate PCR primers used for the initial screening of mouse thymus cDNA library. The alternative splicing sites are indicated by vertical arrows. Diamonds indicate the position of the termination codon. FIG. 1B is a diagram of the alternative splicing and protein structure of caspase-12. The exons and introns between them are shown as bars and lines, respectively (top). Nucleotides at the exon/intron boundaries are indicated. Numbers above the bars correspond to nucleotide numbers in the caspase-12L cDNA sequence. A schematic comparison of caspase-12L (419 residues) and caspase-12S (349 residues) proteins is shown at the bottom. Potential cleavage sites for maturation of the precursor proteins are indicated below the bars with the residues at the sites.

FIGS. 2A–2D. Sequence alignment of caspase-12. FIGS. 2A–C show the sequence alignment of caspase-12 protein with other members of the caspase family: caspase-5 (SEQ ID NO:4), hICE (SEQ ID NO:5), mICE (SEQ ID NO:6), caspase-11 (SEQ ID NO:7), caspase-4 (SEQ ID NO:8), caspase-5 (SEQ ID NO:4), caspase-2 (SEQ ID NO:10), caspase-3 (SEQ ID NO:11) and CED-3 (SEQ ID NO:12). Seven amino acid residues well conserved among the caspase family are marked with either asterisks (catalytic residues) or filled diamonds (P1 binding). Open diamonds indicate the residues for S2–S4 subsites. FIG. 2D shows the alignment of amino acid residues involved in substrate binding. Amino acid residues of each member of the caspase family are described by one-letter codes: ICE (SEQ ID NO:31), caspase-12 (SEQ ID NO:32); caspase-11 (SEQ ID NO:33), caspase-2 (SEQ ID NO:34), caspase-3 (SEQ ID NO:35) and CED-3 (SEQ ID NO:9). Numbering above the residues corresponds to the positions in human ICE. Seven residues which form the P1 active pocket of ICE are grouped into those involved in catalysis (His, Gly, Cys) and those for binding (Arg, Gln, Arg, Ser).

FIG. 4A shows Rat-1 cells that were transiently transfected with the casp-12L-lacZ construct, fixed 24 hr later, and stained with anti-β-galactosidase antibody (left panels) or by Hoechst dye 33258 (right panels). The round cells expressing the casp-12L-lacZ fusion proteins show condensed and fragmented nuclei. FIG. 4B shows Rat-1 cells that were transiently transfected with the control lacZ vector and treated as in A. The nuclear morphology in β-galactosidase-positive cells is normal and noncondensed (indicated by arrows). FIG. 4C shows Rat-1 cells and rat embryonic fibroblast cells that were transfected with the expression constructs, fixed 24 hr later, and stained with X-Gal solution for 3 hr. The data shown are the percentage of round blue cells among total number of blue cells counted. In each transfection, over 200 blue cells were randomly chosen and counted. The data of Rat-1 cells collected from at least three independent experiments. The constructs used were: casp-12L-lacZ, casp-12S-lacZ, casp-12Δ-lacZ, ICE-lacZ, lacZ. Rat embryonic fibroblast cells (REF) were also transfected with either casp-12L-lacZ or lacZ.

FIG. 5A shows a bcl-2 expressing stable transfectant, Rat-1/bcl-2, that was transiently transfected with casp-12L-lacZ. Cell death was assayed as described in FIG. 4C. FIG. 5B shows a crmA expressing transfectant, Rat-1/crmA, that was transiently transfected with casp-12L-lacZ. The data from transfection of the parental cell line, Rat-1 (FIG. 4C), are included in the figures for comparison. The lacZ construct was also used for transfection as a control.

FIG. 8A shows SDS-polyacrylamide gel electrophoresis of partially purified proteins. Δ, casp-12Δ (amino acid residues 95–419 of SEQ ID NO:2); Δ2, casp-12Δ2 (amino acid residues 145–419 of SEQ ID NO:2). Proteins were run on 15% gel and detected by Coomassie brilliant blue staining. Arrowheads indicate polypeptides derived from caspase-12 proteins. FIG. 8B is a diagram of processing sites on caspase-12Δ and caspase-12Δ2. FIG. 8C shows [$^{35}$S]-labeled proteins that were incubated with (+) or without (−) partially purified caspase-12Δ2 for 1 hr at 37° C. Reaction was stopped by boiling with the addition of sample buffer for SDS-polyacrylamide gel electrophoresis. The molecular sizes in kilodaltons are indicated at the left.

FIG. 9. Sequence of casp-12S. cDNA sequence (SEQ ID NO:13) and deduced amino acid sequence (SEQ ID NO:14) of caspase-12S.

DETAILED DESCRIPTION OF THE PREFERRED EMBODIMENTS

Figure 1B:
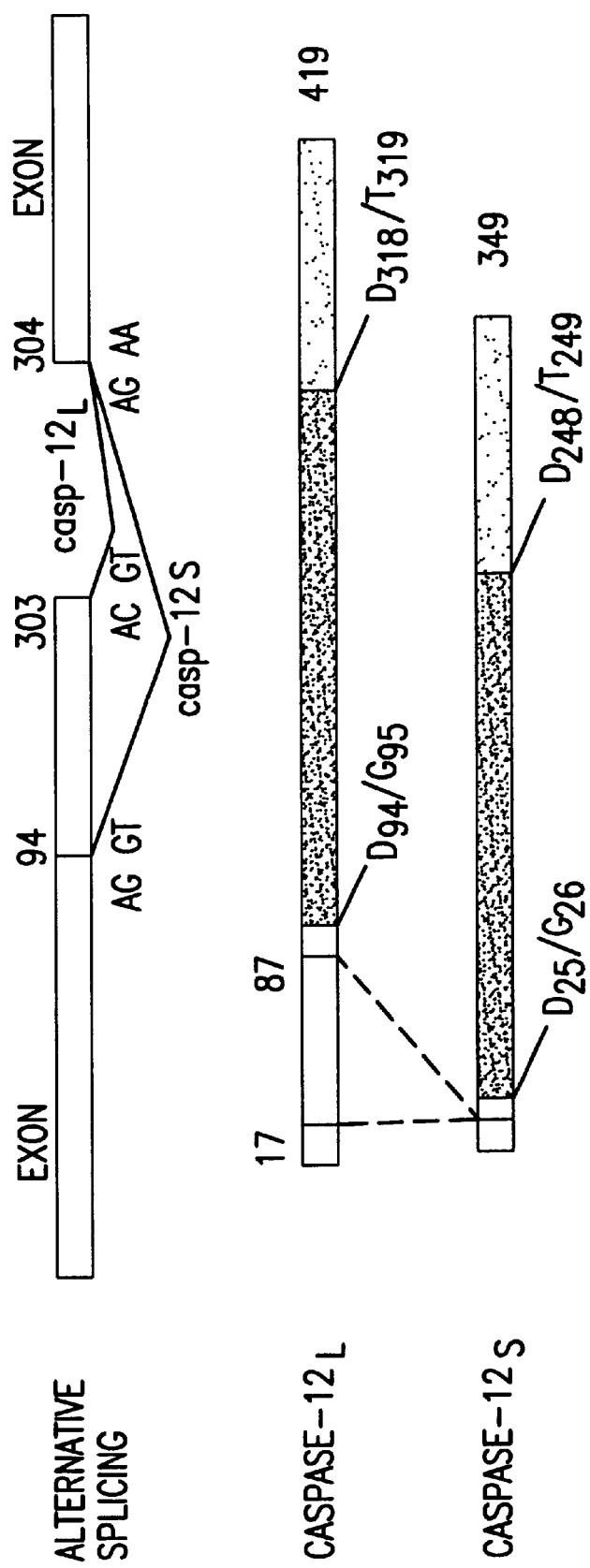

In the description that follows, a variety of technical terms are used. These terms shall have their ordinary well-recognized meaning in the art, unless the context indicates otherwise. In order to provide clearer and more consistent understanding of the specification and the claims, the following definitions are provided.

Caspase. This is the current designation for members of the ICE/Ced-3 family of apoptosis proteins.

Caspase-12 activity. A polypeptide having caspase-12 activity should be understood to be a polypeptide having "caspase-12 activity" similar, but not necessarily identical activity to the caspase-12 protein measured in a particular biological assay. For example, caspase-12 is able to induce programmed cell death in rat embryonic fibroblast cells. Therefore, a polypeptide which is able to induce programmed cell death in rat embryonic fibroblast cells is said to have "caspase-12 activity."

Cell Extract. A cell extract that contains the nucleic acid or polypeptide of interest should be understood to mean a preparation such as a homogenate or cell-free preparation obtained from cells that express the polypeptide or contain the nucleic acid of interest. The term "cell extract" is intended to include culture media, especially spent culture media from which the cells have been removed.

Fragment. A fragment of a molecule should be understood as referring to a nucleic acid molecule or polypeptide that contains a shortened nucleotide or amino acid sequence compared to a reference nucleic acid molecule or polypeptide. The fragment may or may not retain one or more desired chemical or biological properties of the full-length nucleic acid molecule or polypeptide. Examples of caspase-12 fragments are casp-12Δ or casp-12Δ2.

Functional Derivative. A functional derivative of caspase-12 should be understood as referring to a polypeptide, or nucleic acid encoding a polypeptide, that possesses a biological activity that is substantially similar to the biological activity of caspase-12. A functional derivative may or may not contain post-translational modifications such as covalently linked carbohydrates, depending on the necessity of such modifications for the performance of a specific function. The term "functional derivative" is intended to include the "fragments," "variants," "analogues," or "chemical derivatives" of a molecule. The derivative retains at least one of the naturally-occurring functions of the parent gene or protein. The function can be any of the regulatory gene functions or any of the function of the finally processed protein. The degree of activity of the function need not be quantitatively identical to the caspase-12 activity as long as the qualitative function is substantially similar.

Host. As used herein, a "host" or a "host cell" is a cell into which a recombinant nucleic acid has been introduced. A heterologous host is a host that normally does not express the gene or protein of interest.

Isolated. As used herein, an "isolated" molecule refers to a molecule that has been removed from its native environment. Isolated nucleic acid molecules include nucleic acid molecules contained in a recombinant vector; purified nucleic acid molecules in solution, and nucleic acid molecules produced in heterologous host cells. Isolated polypeptides include recombinantly produced polypeptides expressed in host cells; native or recombinant polypeptides which have been essentially or partially purified by any suitable technique known in the art; and polypeptides produced synthetically.

Modulating programmed cell death. Modulating programmed cell death should be understood as referring to either an increase or a decrease in programmed cell death following manipulation of a cell. Such manipulation can be the result of transfection or transformation of cells with particular casp-12 constructs, e.g., casp-12S or casp-12L. Alternatively, one may contact a cell with a polypeptide of interest.

Mutation. A "mutation" should be understood as referring to a detectable change in the genetic material which may be transmitted to daughter cells and possibly even to succeeding generations giving rise to mutant cells or mutant organisms. If the descendants of a mutant cell give rise only to somatic cells in multicellular organisms, a mutant spot or area of cells arises. Mutations in the germ line of sexually reproducing organisms may be transmitted by the gametes to the next generation resulting in an individual with the new mutant condition in both its somatic and germ cells.

A mutation may be any (or a combination of) detectable change affecting the chemical or physical constitution, mutability, replication, phenotypic function, or recombination of one or more nucleotides. In a mutation, nucleotides may be added, deleted, substituted, inverted or transposed to new positions with and without inversion. Mutations may occur spontaneously or can be induced experimentally by application of mutagens. A mutant variation of a nucleic acid molecule results from a mutation. A mutant polypeptide may result from a mutant nucleic acid molecule.

Nucleotide sequence. As used herein "nucleotide sequence" refers to a series of deoxyribonucleotides, in the case of DNA, or of ribonucleotides, in the case of RNA. Nucleotide sequences are herein presented as a sequence of deoxyribonucleotides, abbreviated as follows: A for adenine, C for cytosine, G for guanine, and T for thymine. However, the nucleotide sequences presented herein are intended to also represent RNA sequences, wherein each deoxyribonucleotide thymine is replaced by a ribonucleotide uracil.

Operably linked. Two nucleotide sequences are said to be "operably linked" if induction of promoter function results in the transcription of the coding sequence and if the nature of the linkage between the two DNA sequences does not: (1) result in the introduction of a frame-shift mutation; (2) interfere with the ability of regulatory sequences to direct the expression of the coding sequence; or (3) interfere with the ability of the coding sequence template to be transcribed by the promoter region sequence. Thus, a promoter region would be operably linked to a nucleotide sequence if the promoter were capable of effecting transcription of that nucleotide sequence.

% identical. As used herein, a first nucleotide sequence is said to be, for instance, "95% identical" to the nucleotide sequence of a second reference nucleic acid if the first nucleotide sequence is identical to the complete length of the reference sequence, except that the nucleotide sequence of the first nucleic acid may include up to 5 substitutions per each 100 nucleotides of the second, reference sequence. This includes any combination of deletions, insertions, or single nucleotide substitutions up to five per each 100 nucleotides of the reference sequence. Likewise, a sequence is "85% identical" to a reference sequence if the nucleotide sequence of the nucleic acid is identical to the reference sequence except that the nucleotide sequence may include up to 15 substitutions per each 100 nucleotides of reference sequence. This applies equally to amino acid sequences, therefore one amino acid sequence may be, for example, 95% identical to a second amino acid sequence by having 95 out of 100 of the same amino acids as the reference amino acid sequence.

As a practical matter, whether any particular nucleic acid molecule is at least 80%, 85%, 90%, 95%, 96%, 97%, 98%, or 99% identical to, for instance, the nucleotide sequence shown in FIG. 1 (SEQ ID NO:1) or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman (*Advances in Applied Mathematics* 2:482–489 (1991)) to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

Population. A "population of nucleic acid molecules" is a mixture of nucleic acid molecules, in which at least some nucleic acid molecules are non-identical to the other nucleic acid molecules in the mixture. This includes, inter alia, cDNA libraries made from one cell type; extractions from heterologous cells, which include both DNA and RNA, or which include DNA or RNA only; and extractions from homologous cells, which include both DNA and RNA, or which include DNA or RNA only.

Purified. Preparations made from biological cells or hosts that are said to be "purified" are any cell extract containing the indicated nucleic acid or polypeptide including a crude extract of the nucleic acid or polypeptide of interest. Such preparations include molecules removed from their native environment. For example, in the case of a polypeptide, a purified preparation can be obtained following an individual technique or a series of preparative or biochemical techniques, and the polypeptide of interest can be present at various degrees of purity in these preparations. The procedures include, but are not limited to, ammonium sulfate fractionation, gel filtration, ion exchange chromatography, affinity chromatography, density gradient centrifigation, electrophoresis, and other techniques known to those of skill in the art. See, e.g., *Current Protocols in Molecular Biology*, John Wiley and Sons (1996).

A preparation of nucleic acid or polypeptide that is "pure" should be understood to mean a preparation free from naturally occurring materials with which such nucleic acid or polypeptide is normally associated in nature. "Essentially pure" should be understood to mean a "highly" purified preparation that contains at least 95% of the nucleic acid or protein of interest. Preparations of nucleic acids or polypeptides of interest that are "partially pure" are less pure than preparations that are essentially pure, and include crudely purified nucleic acids or polypeptides.

Stringent Hybridization. Stringent hybridization conditions should be understood to be those conditions normally used by one of skill in the art to establish at least a 90% homology between complementary pieces of nucleic acids. Lesser homologies, such as at least 70% homology or preferably at least 80% homology, may also be desired and obtained by varying the hybridization conditions.

There are only two required conditions for hybridization to a denatured strand of nucleic acid to occur: (1) there must be complementary single strands in the sample; and (2) the ionic strength of the solution of single-stranded nucleic acid must be fairly high so that the bases can approach each other; operationally, this is greater than 0.2 M. A third condition affects the rate of hybridization: the nucleic acid concentration mush be high enough for intermolecular collisions to occur at a reasonable frequency.

Conditions routinely used by those of skill in the art are set out in readily available procedure texts, e.g., *Current Protocols in Molecular Biology*, Vol. I, Chap. 2.10, John Wiley & Sons, Publishers (1994) or Sambrook et al., *Molecular Cloning*, Cold Spring Harbor (1989), incorporated herein by reference. As would be known by one of skill in the art, the ultimate hybridization stringency reflects both the actual hybridization conditions as well as the washing conditions following the hybridization. One of skill in the art would know the appropriate manner in which to change these conditions to obtain a desired result.

For example, a prehybridization solution should contain sufficient salt and nonspecific nucleic acid to allow for hybridization to non-specific sites on the solid matrix, at the desired temperature and in the desired prehybridization time. For example, for stringent hybridization, such prehybridization solution could contain 6×sodium chloride/sodium citrate (1×SSC is 0.15 M NaCl, 0.015 M Na citrate; pH 7.0), 5×Denhardt's solution, 0.05% sodium pyrophosphate and 100 µg per ml of herring sperm DNA. An appropriate stringent hybridization mixture might then contain 6×SSC, 1×Denhardt's solution, 100 µg per ml of yeast tRNA and 0.05% sodium pyrophosphate.

Alternative conditions for nucleic acid hybrid analysis could entail the following:

1) prehybridization at room temperature and hybridization at 68° C.;
2) washing with 0.2×SSC/0.1% SDS at room temperature;
3) as desired, additional washes at 0.2×SSC/0.1% SDS at 42° C. (moderate-stringency wash); or
4) as desired, additional washes at 0.1×SSC/0.1% SDS at 68° C. (high stringency).

Known hybridization mixtures, e.g., that of Church and Gilbert, *Proc. Natl. Acad. Sci. USA* 81:1991–1995 (1984), comprising the following composition may also be used: 1% crystalline grade bovine serum albumin/1 mM EDTA/0.5M NaHPO$_4$, pH 7.2/7% SDS. Additional, alternative but similar reaction conditions can also be found in Sambrook et al., *Molecular Cloning*, Cold Spring Harbor (1989). Formamide may also be included inprehybridization/hybridization solutions as desired.

It should be understood that these conditions are not meant to be definitive or limiting and may be adjusted as required by those of ordinary skill in the art to accomplish the desired objective.

Vector. As used herein, a vector is a vehicle which provides an appropriate nucleic acid environment for a transfer of a nucleic acid of interest into a host cell. Such a vector may be used for cloning or expressing a desired sequence, such as a nucleotide sequence of a caspase-12 encoding nucleic acid of the invention, in an appropriate host. An expression vector may contain the nucleic acid of interest operably linked to a homologous or heterologous promoter or regulatory sequences.

In one embodiment of the present invention, isolated nucleic acid molecules having a nucleotide sequence encoding an amino acid sequence corresponding to caspase-12 are provided. In one preferred embodiment, the isolated nucleic acid molecule has a nucleotide sequence encoding the amino acid sequence of casp-12S as shown in FIG. 9 (SEQ ID NO:14). In another preferred embodiment, the isolated nucleic acid molecule has a nucleotide sequence encoding the amino acid sequence encoded by the cDNA clone deposited as ATCC Deposit No. 209710 on Mar. 18, 1998 at the American Type Culture Collection (ATCC), 10801 University Boulevard, Manassas, Va., 20110-2209. In another preferred embodiment, the isolated nucleic acid molecule has a nucleotide sequence encoding the amino acid sequence of casp-12Δ (amino acids 95 to 419 of SEQ ID NO:2). In yet another preferred embodiment, the isolated nucleic acid molecule has a nucleotide sequence encoding the amino acid sequence of casp-12Δ2 (amino acids 145 to 419 of SEQ ID NO:2).

Additionally, nucleic acid molecules of the invention may include only the coding region of the sequence, with or without leader sequences.

Isolated nucleic acid molecules of the present invention may be in the form of RNA, for example, mRNA, or in the form of DNA, for example, cDNA. The DNA may be double-stranded or single-stranded. Single-stranded DNA or RNA may by the coding strand, which is also known as the sense strand, or it may be the non-coding strand, which is also known as the anti-sense strand.

The nucleic acid molecules of the present invention may be chemically synthesized or they may be produced using standard cloning and screening procedures which are well known in the art. See, e.g., *Current Protocols in Molecular Biology*, John Wiley and Sons (1996). Provided in Example 1 is a description of one preferred method for cloning and screening for the nucleic acid molecules of the present invention.

As can be appreciated by one of ordinary skill in the art, there are nucleic acid molecules other than those specifically depicted here, which due to the degeneracy of the genetic code, will encode the amino acid sequence of casp-12S as shown in FIG. 9 (SEQ ID NO:14) or as encoded by the cDNA clone contained in ATCC Deposit No. 209710. All degenerate variants of the claimed sequences are also encompassed by the invention. The genetic code is well known in the art. Thus, it would be routine for one skilled in the art to generate nucleic acids, other than those specifically depicted here, that still encode the amino acid sequence of the invention.

In another embodiment of the present invention, there are provided nucleic acid molecules having a nucleotide sequence that is at least 80%, and preferably at least 85% or 90%, still more preferably at least 95%, 96%, 97%, 98%, or 99%, identical to the nucleotide sequences described above. The present invention is directed to nucleic acid molecules having a nucleotide sequence at least 80% identical to the nucleotide sequence of the above-recited nucleic acid molecules irrespective of whether or not they encode a polypeptide having caspase-12 activity. This is because, even where a particular nucleic acid molecule does not encode a polypeptide having caspase-12 activity, one of skill in the art would still know how to use the nucleic acid molecule, for instance as a probe. Uses of the nucleic acid molecules of the present invention that do not encode a polypeptide having caspase-12 activity include, inter alia, isolating the caspase-12 gene or allelic variants thereof in a cDNA library; flourescent in situ hybridization ("FISH") to metaphase chromosomal spreads to provide precise chromosomal location of the caspase-12 gene as described in Verma et al., *Human Chromosomes: a Manual of Basic Techniques*, Pergamon Press, New York (1988); and Northern Blot analysis for detecting caspase-12 mRNA expression in specific tissues.

Preferred, however, are nucleic acid molecules having a nucleotide sequence at least 80%, more preferably 85% or 90%, still more preferably at least 95%, 96%, 97%, 98%, or 99% identical to the nucleotide sequence of the above-described nucleic acid molecules which in fact encode a polypeptide having a caspase-12 activity. One of ordinary skill in the art would immediately recognize that, due to the degeneracy of the genetic code, a large number of nucleic acid molecules having a nucleotide sequence at least 80%, more preferably 85% or 90%, still more preferably at least 95%, 96%, 97%, 98%, or 99% identical to the nucleotide sequence of the above-described nucleic acid molecules will encode a polypeptide of the present invention. Since the degenerate variants of the claimed molecules all encode the same polypeptide as the original sequence, it would be clear to the skilled artisan that degenerate the variants will encode a polypeptide having activity similar to that of the original sequence, even without performing screening assays, e.g. for caspase-12 activity. Uses of nucleic acid molecules which encode a polypeptide having caspase-12 activity include, inter alia, modulating programmed cell death by inserting the nucleic acid molecule into a cell, and production of polypeptides with caspase-12 activity by inserting the nucleic acid molecule into a vector, transforming a host cell with the vector, and inducing expression of the polypeptide.

It will be further recognized by those skilled in the art that, even for such nucleic acid molecules that are not degenerate variants, a reasonable number will also encode a polypeptide having caspase-12 activity. This is because the skilled artisan is aware of possible amino acid substitution that are less likely or not likely to significantly affect protein function.

For example, "conservative" amino acid substitutions generally have little effect on activity of a polypeptide. Typically seen as conservative amino acid substitutions are: exchange of aromatic residues Phe and Try; exchange of the basic residues Lys and Arg; exchange of the amide residues Asn and Gln; exchange of the acidic residues Asp and Glu; exchange of the hydroxyl residues Ser and Thr; and substitution among the aliphatic residues Ala, Val, Leu, and Ile. Further guidance concerning how to make phenotypically silent amino acid substitution is provided, for example, in Bowie et al., *Science* 247:1306–1310 (1990).

A further embodiment of the present invention provides for a vector comprising a nucleic acid molecule described above. Vectors useful in the present invention include chromosomal-, episomal- and virus-derived vectors, for example, vectors derived from bacterial plasmids, yeast episomes, yeast chromosomal elements, viruses such as bacteriophage, baculoviruses, papova viruses, herpes viruses, vaccinia viruses, adenoviruses, fowl pox viruses, pseudorabies viruses and retroviruses, and vectors derived from combinations thereof, such as cosmids and phagemids.

If desired, a recombinant vector encoding a fusion product of a polypeptide of the invention may be constructed. For example, the nucleotide sequence encoding a polypeptide of the invention may be linked to a signal sequence which allows secretion of the polypeptide from, or the compartmentalization of the polypeptide in, a particular host. Such signal sequences may be designed with or without specific protease sites such that the signal peptide sequence is amenable to subsequent removal. Alternatively, the polypeptide may be fused to a sequence which enabled easier purification of the polypeptide, for example, a Histidine tag.

For cloning into a vector, a nucleic acid molecule of the present invention is randomly sheared or enzymatically cleaved, and ligated into an appropriate vector. Methods for cloning nucleic acids into vectors are well known in the art. See, for example, Sambrook et al., *Molecular Cloning*, Cold Spring Harbor (1989).

The nucleic acid molecules may be joined to a vector containing a selectable marker suitable for use in identifying cells transformed with the vector. Examples of selectable markers include dihydrofolate reductase or neomycin resistance for eukaryotic cell culture and tetracycline or ampicillin resistance genes for culturing in bacteria.

Certain preferred vectors provide for specific expression of the nucleic acid molecule, which may be inducible and/or cell-type specific. Particularly preferred among such vectors are those inducible by environmental factors that are easily manipulated, such as temperature or nutrient additives. In this regard, the nucleic acid insert should be operably linked to an appropriate promoter, for example, the phage lambda PL promoter, the *E. coli* lac promoter, the SV40 early and late promoters, the CMV immediate early promoter, the HSV thymidine kinase promoter, the promoters of retroviral LTRs, and metallotionein promoters.

Still another embodiment of the present invention is a host transformed with a vector described above. The sequence may be incorporated into the genome of the host cell, or it may be maintained extrachromasomally. Recombinant vectors may be introduced into host cells using well known techniques such as infection, transduction, transfection, transvection, electroporation, and transformation.

Examples of appropriate hosts include, but are not limited to, bacterial cells, such as *E. coli* and *Salmonella typhimurium* cells; fungal cells, such as yeast cells; insect cells, such as Drosophila S2 and Spodoptera Sf9 cells; animal cells, such as CHO, COS cells, NIH 3T3 cells, human 293 cells, 293T cells, and HeLa cells; and plant cells. Appropriate culture conditions for the above-described host cells are known in the art.

Expression of the polypeptides of the invention from recombinant vectors in hosts may require the presence of regulatory regions functional in such hosts. The precise nature of the regulatory regions needed for gene expression may vary between species or cell types, but shall in general include, as necessary, 5' non-transcribed and/or non-translated and/or 3' non-transcribed and/or non-translated (non-coding) sequences involved with the regulation of transcription and translation, such as the TATA box, capping sequence, CAAT sequence, sequences for transcriptional termination, and the like. Such 5' non-transcribed control sequences may include the region which contains a promoter for transcriptional control of the operably linked gene.

In eukaryotic hosts, where transcription is not linked to translation, control regions may or may not provide an initiator methionine (ATG) codon, depending on whether the cloned sequence contains such a methionine. Such regions will, in general, include a promoter region sufficient to direct the initiation of RNA synthesis in the host cell. The promoter region may be a homologous or heterologous promoter. A heterologous promoter is one that is not normally associated with the nucleic acid being expressed. For example, the use of a cytomegalovirus promoter with a mouse ICE gene on or an acting promoter with a mouse ICE gene are uses of a heterologous promoter. The homologous promoter for casp-12 is the promoter with which the casp-12 gene is operably linked naturally.

Further embodiments of this invention relate to caspase-12 polypeptides. In one preferred embodiment, there is provided an isolated polypeptide having an amino acid sequence of caspase-12S as shown in FIG. 9 (SEQ ID NO:14). In another preferred embodiment, there is provided an isolated polypeptide having an amino acid sequence of caspase-12S as encoded by the cDNA clone contained in ATCC Deposit No. 209710. In another preferred embodiment, there is provided an isolated polypeptide having an amino acid sequence of caspase-12Δ (amino acid residues 95–419 of SEQ ID NO:2). In yet another preferred embodiment, there is provided an isolated polypeptide having an amino acid sequence of caspase-12Δ2 (amino acid residues 145–419 of SEQ ID NO:2).

Polypeptides of the present invention include, but are not limited to, naturally purified products, chemically synthesized polypeptides, and polypeptides produced by recombinant techniques. Expression of polypeptides by recombinant techniques may result in different post-translational modifications, dependent on the host cell. These modified forms of the polypeptides are also encompassed by the claimed invention.

It would be readily recognized by one of skill in the art that some amino acid residues of caspase-12S could be varied without significant effect on the structure or function of the protein. Such variations include deletions, insertions, inversions, repeats, and type substitutions. Guidance concerning which amino acid changes are likely to be phenotypically silent can be found in Bowie et al., *Science* 247:306–1310 (1990).

Thus, another embodiment of the present invention are polypeptides which are 80%, more preferably 85% or 90%, still more preferably at least 95%, 96%, 97%, 98%, or 99% identical to the above-described polypeptides. Preferably, these polypeptides will display caspase-12 activity. A skilled artisan is fully aware of possible amino acid substitution that are less likely or not likely to significantly affect protein function. Guidance concerning how to make phenotypically silent amino acid substitution is provided, for example, in Bowie et al., *Science* 247:1306–1310 (1990).

The polypeptides of the invention may be used for the purpose of generating polyclonal or monoclonal antibodies using standard techniques known in the art (Klein, J., *Immunology: The Science of Cell-Noncell Discrimination*, John Wiley & Sons, N.Y. (1982); Kennett et al., *Monoclonal Antibodies, Hybridoma: A New Dimension in Biological Analyses*, Plenum Press, N.Y. (1980); Campbell, A., "Monoclonal Antibody Technology," In: *Laboratory Techniques in Biochemistry and Molecular Biology* 13, Burdon et al. eds., Elseiver, Amsterdam (1984); Harlow and Lane, *Antibodies, A Laboratory Manual*, Cold Spring Harbor Laboratory, N.Y. (1988)). Such antibodies may be used in assays for determining gene expression and for screening expression libraries. Purified protein would serve as the standard in such assays.

The present inventors have shown that caspase-12 induces apoptosis in cells. Thus, another embodiment of the present invention is a method of inducing programmed cell death in a cell comprising contacting the cell with a polypeptide described above. For the purpose of inducing programmed cell death in a cell, the polypeptides of the present invention can be administered to a cell in vitro or in vivo.

The polypeptides may be administered to the cell exogenously. The polypeptides may also be administered through recombinant expression. For example, homologous recombination can be used to express the polypeptides of the invention in cells. Extrachromosomal nucleic acids with the appropriate nucleotide sequence can also be introduced into cells.

Induction of apoptosis can be used to treat, inter alia, malignant and pre-malignant conditions, and autoimmune disorders. Malignant and pre-malignant conditions may include solid tumors, B cell lymphomas, chronic lymphocytic leukemia, prostate hypertrophy, preneoplastic liver foci and resistance to chemotherapy.

The following are presented as representative, but non-limiting, examples of the present invention. Other suitable modifications are within the scope of the present invention and will be apparent to one of ordinary skill in the art.

EXAMPLE 1

Caspase-12 is a Member of the Caspase Family

To isolate additional members of the caspase family, two degenerate primers based upon sequences of two conserved regions among the members of the caspase family were designed: the pentapeptide motif QACRG (SEQ ID NO:3) around the active cysteine residue and a hexapeptide sequence FYLFPG (SEQ ID NO:17) at the C-terminus. This pair of degenerate primers were used to amplify cDNA from mouse thymus which generated a 400 bp fragment as expected for caspases. This fragment was cloned and subjected to restriction enzyme and sequence analyses, which showed that there are several different cDNA species in this 400 bp band. One of them, named caspase-12, was a novel member of the caspase family with a deduced amino acid sequence sharing about 35% identity with mouse ICE. Southern blot analysis of mouse genomic DNA showed that caspase-12 is a single copy gene. Using this cDNA clone as a probe, nine clones from mouse thymus cDNA library were isolated. These nine positive clones can be classified into two groups: Long form of the caspase-12 cDNA (plasmid pNB6, casp-12L) and short form (plasmid pNB7, casp-12S).

Methods

PCR amplification of Caspase-12 cDNA

Standard techniques of molecular cloning were used as described (Sambrook, J., et al., *Molecular cloning: a laboratory manual* (second edition), Cold Spring Harbor Laboratory, Cold Spring Harbor, N.Y. (1989)), unless otherwise stated. A partial cDNA clone for caspase-12 was amplified from murine thymus cDNA by polymerase chain reaction (PCR) using degenerate oligonucleotide primers: upstream, 5'-TG(GATC) CC(GATC) GGGAA(GATC) AGG TAG AA-3' (SEQ ID NO:15); downstream, 5'-ATC AT(ATC) ATC CAG GC(GATC) TGC AG(AG) GG-3' (SEQ ID NO:16) (bases in parentheses indicate degenerate nucleotides). The following conditions were used for the PCR reactions: 1×reaction buffer (Promega), 1.5 mM MgCl$_2$, 200 mM dNTP, 2 mM each primer, 1 unit of Taq DNA polymerase (Promega) in a total volume of 50 μl. cDNA was denatured for 4 min at 94° C. prior to 25 cycles of 94° C. for 1 min, 46° C. for 1 min, 72° C. for 2 min. A 0.4 kb PCR product was cloned into the EcoRV site of pBluescript II SK(−) plasmid vector (Stratagene). *E. coli* cells were transformed with the plasmid DNA and individual colonies were isolated and prepared for DNA sequencing. A novel caspase cDNA was identified based upon DNA sequence and was named caspase-12.

The 0.4 kb cDNA fragment was labeled with [$^{32}$P] dATP (Amersham) and used to screen a murine thymus cDNA library (Stratagene) under high stringent conditions. Nine positive clones were identified from about 10$^7$ phage clones. The plasmid DNAs were excised from phage DNAs by an in vivo excision protocol (Stratagene). Eight out of the nine clones contain identical sequences with a 419 amino acid residue open reading frame and was designated as caspase-12L (FIG. 1A). The ninth clone is 210 bp shorter than caspase-12L because it does not contain the bases 94 through 303 of caspase-12L (FIG. 1B). The missing sequence starts from a dinucleotide sequence, GT, which is a probable mammalian splice donor site. Analysis of the caspase-12 genomic clones showed that the base 303/304 is located exactly at a splice junction, and the base 304 is preceded by a dinucleotide sequence AG in the intronic sequence, conforming to the GT/AG rule for splice donor/acceptor site (FIG. 1B). Thus, the shorter clone was likely derived from an alternatively spliced mRNA. The short form of mRNA was named caspase-12S which contains an open reading frame of 349 amino acid residues.

A potential processing site in pro-caspase-12L is found at Asp94/Gly95 (Asp24/Gly25 in caspase-12S). The 210 bp sequence which is missing in caspase-12S (codons 17–87) probably encodes the sequence within the pro-domain of the caspase-12 (FIG. 1B), which could be removed during proteolytic processing of precursor form to generate a mature protein. Both caspase-12L and caspase-12S proteins have another possible processing site (Asp318/Thr319 in caspase-12L, Asp248/Thr249 in caspase-12S), corresponding to the cleavage site between p20 and p10 fragments of ICE. Thus, the difference between caspase-12L and caspase-12S is in their pro-domains and processing of caspase-12L and caspase-12S would give rise to a mature enzyme of identical subunit composition and sequences.

The caspase family can be divided into three subfamilies according to their amino acid sequence similarity: the ICE subfamily, the caspase-2 subfamily, and the caspase-3 subfamily (Duan, H., et al., *J. Biol. Chem.* 271:1621–1625 (1996)). The caspase-12L protein shares 41% sequence identity with human ICE (Thornberry, N. A., et al., *Nature* 356:768–774 (1992)), 41% sequence identity with mouse ICE (Miura, M., et al., *Cell* 75:653–660 (1993); Nett, M. A., et al., *J. Immunol.* 149:3254–3258 (1992), 42% sequence identity with mouse caspase-11 (Wang, S., et al., *J. Biol. Chem.* 271:20580–20587(1996)), 49% with human caspase-4 (Faucheu, C., et al, *The EMBO Journal* 14:1914–1922 (1995)), 46% with human caspase-5 (Munday, N. A., et al., *J. Biol. Chem.* 270:15870–15876 (1995)), 21% with human caspase-2L (Wang, L., et al., *Cell* 78:739–750 (1994)), 20% with human caspase-3 (Fernandez-Alnemri, T., et al., *J. Biol. Chem.* 269:30761–30764 (1994)), and 18% with the *C. elegans* Ced-3 (Yuan, J., et al., *Cell* 75:641–652 (1993)) (FIGS. 2A–C, Table 1). The comparison of the caspase-12 amino acid sequence with those of other caspase family members suggests that caspase-12 belongs to the ICE subfamily, which includes ICE, caspase-4, -5 and -11.

TABLE 1

Sequence Similarity Among Caspase Family (% Identity)

|  | hICE | caspase-11 | caspase-4 | caspase-5 | caspase-2 | caspase-3 | CED-3 |
|---|---|---|---|---|---|---|---|
| caspase-12 | 41 | 42 | 49 | 46 | 21 | 20 | 18 |
| hICE |  | 46 | 49 | 49 | 26 | 32 | 28 |
| caspase-11 |  |  | 60 | 54 | 30 | 32 | 26 |
| caspase-4 |  |  |  | 73 | 28 | 32 | 27 |
| caspase-5 |  |  |  |  | 25 | 30 | 25 |
| caspase-2 |  |  |  |  |  | 28 | 28 |
| caspase-3 |  |  |  |  |  |  | 34 |

Figure 2D:
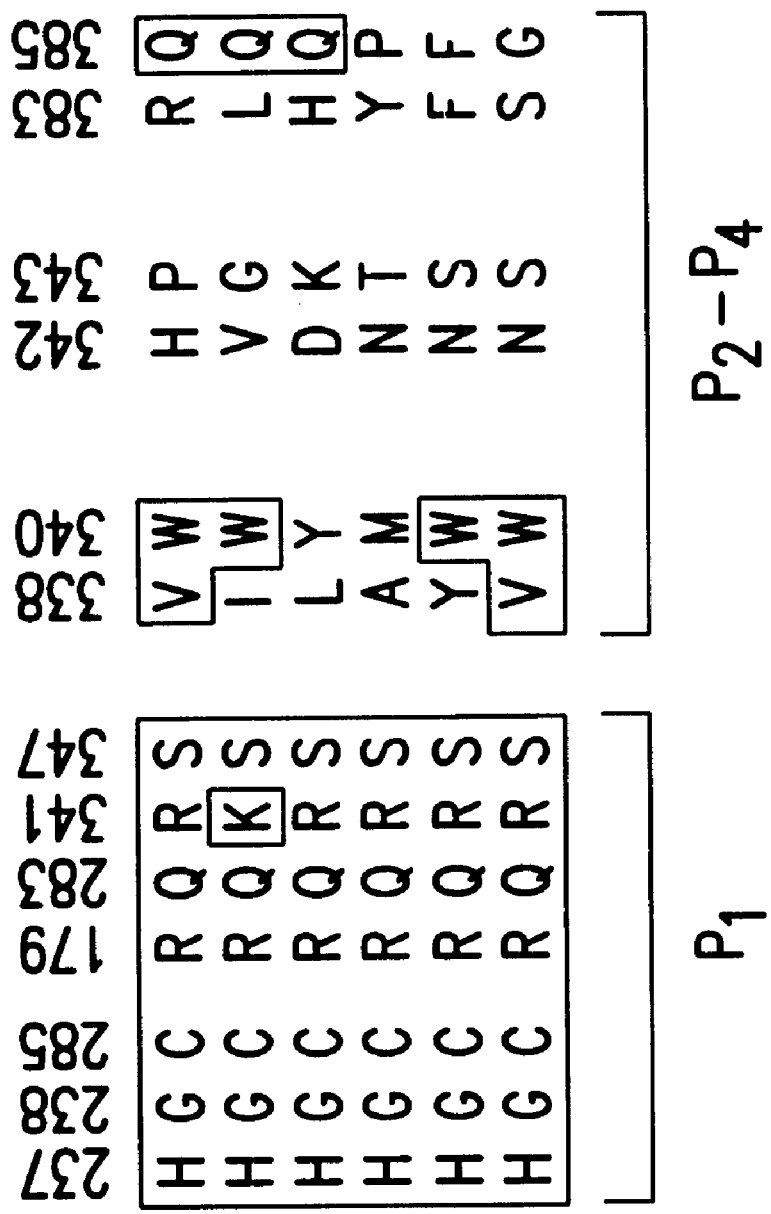

The X-ray crystallography of the ICE protein has revealed that the p10 subunit apparently makes a direct contact with P2-P4 amino acid residues of a substrate (Walker, N. P. C., et al., *Cell* 78:343–352 (1994); Wilson, K. P., et al., *Nature* 370:270–275 (1994)). Three groups of amino acid residues in ICE are assumed to be the subsites (S2–S4) which recognize and bind to the P2–P4 substrate determinants (FIG. 2D). The first group (Val338 and Trp340 in human ICE) is best conserved among the caspase family. The second one (His342 and Pro343) is least conserved among the ICE subfamily (ICE, caspase-12 and caspase-11), whereas the other three members (caspase-2, caspase-3 and CED-3) show similar composition (Asn and Thr/Ser). The variation in the amino acid composition of the subsites probably reflects different substrate specificity.

Sequence alignment of caspase-12 with ICE reveals that the three residues involved in catalysis of ICE (His237, Gly238 and Cys285, (Walker, N. P. C., et al., *Cell* 78:343–352 (1994); Wilson, K. P., et al., *Nature* 370:270–275 (1994)) are conserved in caspase-12 (His250, Gly251 and Cys298. FIGS. 2A–2D) as well as the residues that are part of the P1 Asp binding pocket in ICE (Arg179, Gln283, Arg341 and Ser347) which correspond to Arg192, Gln286, Lys356, Ser362 in caspase-12 with the only substitution of Arg with Lys at residue 356. This is the first example that a member of the caspase family shows such a substitution at this position. The residues in ICE that make up the groove for binding P2–P4 residues of the substrate (Val338, Trp340, His342, Pro343, Arg383 and Gln385) are less conserved in caspase-12, in which only Trp and Gln are conserved with the corresponding amino acid residues, Ile353, Trp355, Val357, Gly368, Leu398, and Gln400 (FIG. 2D). These results suggest that caspase-12 is a member of the caspase family with P1 Asp specificity but likely to have different P2–P4 preference in its substrates in comparison to that of ICE.

EXAMPLE 2

Expression Pattern of Casp-12

To examine the expression pattern of both casp-12L and casp-12S, fragments of casp-12L and casp-12S messages were amplified by RT-PCR.

Methods

RT-PCR mRNA was isolated from mouse brain, thymus, lung, heart, liver, kidney, spleen, and intestine using the MicroFast mRNA isolation kit (Invitrogen). One microgram of mRNA was used for reverse transcription with random primers and Moloney murine leukemia virus (MoMLV) reverse transcriptase (Invitrogen). The caspase-12 cDNA was amplified with PCR. The conditions of PCR were as follows: 94° C., 1 min; 50° C., 2 min; 72° C., 2 min, 30 cycles. The primers used were: upstream, 5'-GAGATCCAATCTACAAGATC-3' (SEQ ID NO:18); downstream, 5'-CACCACAGAGTATCCAAG-3' (SEQ ID NO:19). These two specific primers span the 210 bp region that is deleted in casp-12S and were designed using sequences from separate exons so that the possibility of amplification from contaminating genomic DNA could be eliminated.

Figure 3:
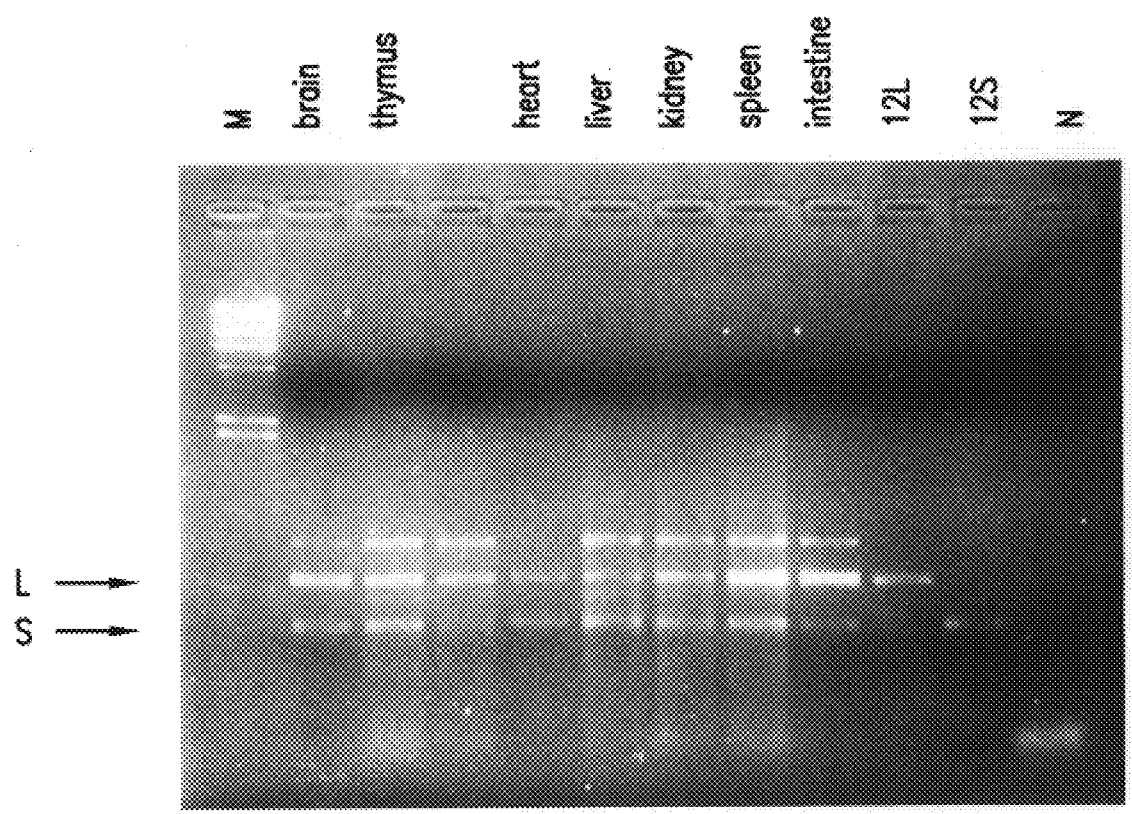
FIG. 3. RT-PCR analysis of caspase-12 in mouse adult tissues. cDNA samples were reverse transcribed from mRNA isolated from brain, thymus, heart, lung, liver, kidney, spleen, and intestine. Lane 12L, PCR products (617 bp) by using casp-12L as a positive control. Lane 12S, PCR products (407 bp) by using casp-12S as a positive control. Arrows indicate these casp-12L and casp-12S specific fragments. M, lambda phage DNA HindIII digest as molecular weight standard. N, negative control as no DNA templates were used for PCR.

In the PCR reaction, both casp-12L and casp-12S can be amplified simultaneously to produce DNA fragments of 617 bp and 407 bp, respectively. Both fragments were amplified from all the tissues examined which include brain, thymus, lung, heart, liver, kidney, spleen and intestine (FIG. 3). These results indicate that both caspase-12L and caspase-12S are ubiquitously expressed in adult tissues. Since ubiquitous expression of several members of the caspase family has been found in adult tissues (Kumar, S., et al., *Genes and Development* 8:1613–1626 (1994); Wang, L., et al, *Cell* 78:739–750 (1994); Fernandez-Alnemnri, T., et al., *J. Biol. Chem.* 269:30761–30764 (1994); Tewari, M., *Cell* 81:801–809 (1995); Faucheu, C., et al., *The EMBO Journal* 14:1914–1922 (1995); Munday, N. A., et al, *J. Biol. Chem.* 270:15870–15876 (1995); Duan, H., et al., *J. Biol. Chem.* 271:1621–1625 (1996); Wang, S., et al., *J. Biol. Chem.* 271:20580–20587 (1996); Van de Craen, M., et al., *FEBS Letters* 403:61–69 (1997)), the caspase-12 protein is likely coexpressed with other members of the caspase family in a single cell.

There was another intense band of 900 bp in each lane of the RT-PCR products (FIG. 3). Cloning and sequencing of this fragment showed that it contains no similarity to casp-12, and it did not hybridize to the casp-12 genomic clones, indicating that this band was amplified from a different genetic locus.

EXAMPLE 3

Overexpression of casp-12 cDNA Induces Apoptosis in Mammalian Cells

To examine if expression of caspase-12 induces apoptosis, a transient expression system was used to overexpress caspase-12 in mammalian cells. Expression constructs of ICE, casp-2 and casp-11 fused with *E. coli* lacZ have been successfully used to demonstrate that expression of these ICE family members induces apoptosis (Miura, M., et al., *Cell* 75:653–660 (1993); Wang, L., et al., *Cell* 78:739–750 (1994); Wang, S., et al., *J. Biol. Chem.* 271:20580–20587 (1996)). Transfected cells are easily detected by staining with X-gal because of the β-galactosidase activity of lacZ. Expression constructs of casp-12L and casp-12S fused with lacZ gene in pcDNA3 vector, which contains the cytomegalovirus (CMV) promoter, were generated. These expression constructs were introduced into Rat-1 cells by transfection, and the expression of the genes were examined 24 hr after transfection using X-gal reaction.

Methods

Plasmid Construction

The long form of caspase-12 cDNA (casp-12L) within pNB6 was amplified by using Vent DNA polymerase (New England Biolabs) and the following primers: upstream, 5'-CTC GAA TTC ATG GCG GCC AGG AGG ACA CAT G-3' (SEQ ID NO:20); and downstream, 5'-CTC GGA TCC TTC CCG GGA AAA GGT AG-3' (SEQ ID NO:21). The amplified fragments were digested with EcoRI and BamHI and then cloned into pBluescript II SK(−) (pBSI95). pBI95Z was made by inserting BamHI fragment of lacZ (Miura, M., et al., *Cell* 75:653–660 (1993)) into pBSI95. The casp-12-lacZ fusion gene was cut out from pBI95Z by using KpnI and XbaI and inserted into pcDNA3 vector (Invitrogen) digested with KpnI and XbaI to generate pNB15. The expression construct pNB16, a fusion of the short form of caspase-12 cDNA (casp-12S) and lacZ in pcDNA3 vector, was generated through the same strategy as described above, using pNB7 instead of pNB6 as a template for PCR.

For the expression construct of caspase-12Δ (amino acid residues 95–419 of SEQ ID NO:2), a part of casp-12L was amplified by PCR with following primers: upstream, 5'-CTC GGT ACC ATG GGA CCT CAG AAG ATA TGT AC-3' (SEQ ID NO:22); and downstream, 5'-CTC GTC GAC CCA TTC CCG GGA AAA AGG TAG-3' (SEQ ID NO:23). The upstream primer contains an ATG for an artificial initiation codon. The amplified fragments were digested with KpnI/SalI and fused with lacZ inpBluescript II SK(−) vector. The casp-12Δ-lacZ fusion gene was excised from the pBluescript-based plasmid using KpnI and XbaI and inserted into KpnI/XbaI sites of pcDNA3 vector.

Cell Culture and Transient Transfection

Rat-1, rat embryonic fibroblast cells, NG108-15, HeLa and COS-1 were maintained in culture at 37° C. with 5% $CO_2$ in Dulbecco's modified Eagle's medium containing 10% (v/v) fetal bovine serum (BioWhittaker) and 50 units/ml penicillin and 50 μg/ml streptomycin (Sigma). The day before transfection, cells were seeded at a density of $1.3 \times 10^4$ cells/cm². Expression constructs were transferred to cells with either calcium phosphate or lipofectamine (GIBCO BRL) as previously described (Miura, M., et al., *Cell* 75:653–660 (1993); Kumar, S., et al., *Genes and Development* 8:1613–1626 (1994); Wang, L., et al., *Cell* 78:739–750 (1994)). The expression of chimeric genes in cells was detected by staining of cells with 5-bromo-4-chloro-3-indolyl β-D-galactoside (X-gal) as previously described (Miura, M., et al., *Cell* 75:653–660 (1993); Kumar, S., et al., *Genes and Development* 8:1613–1626 (1994); Wang, L., et al., *Cell* 78:739–750 (1994)). Immunostaining of transfected cells was done as previously described using mouse monoclonal anti-lacZ antibody (Miura, M., et al., *Cell* 75:653–660 (1993); Kumar, S., et al., *Genes and Development* 8:1613–1626 (1994); Wang, L., et al., *Cell* 78:739–750 (1994)).

Figure 4A:
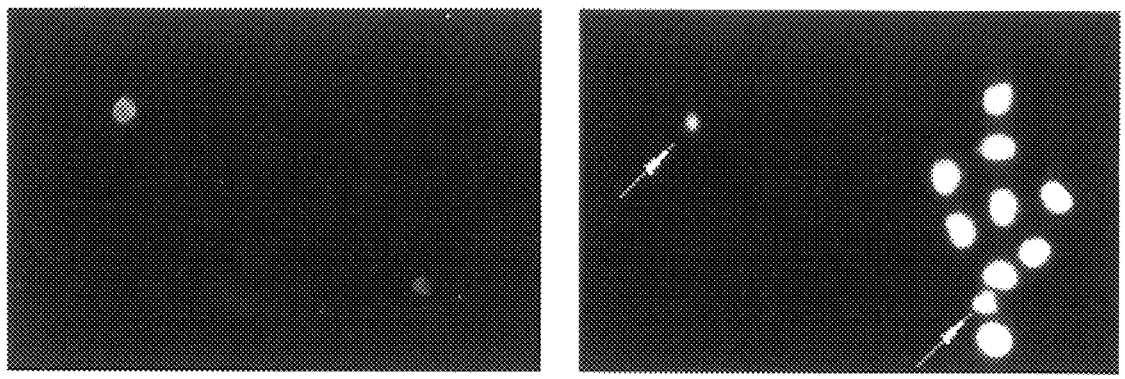
FIGS. 4A–4C. Cell death induced by overexpression of caspase-12.
Figure 4B:
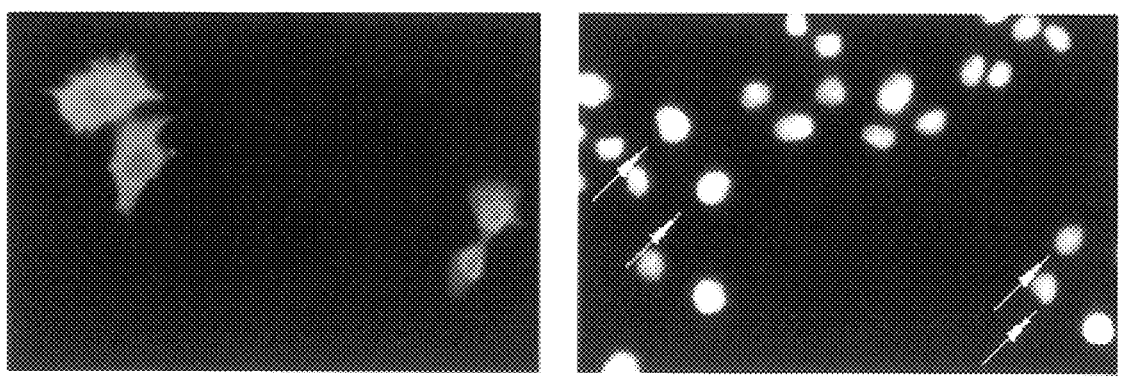

More than half of X-gal positive cells transfected with casp-12-lacZ fusion construct are round and smaller than healthy X-gal positive cells transfected with lacZ alone. Such reduction of cell size is a characteristic feature of apoptotic cells (Miura, M., et al., *Cell* 75:653–660 (1993); Jacobson, M. D., et al., *Nature* 361:365–369 (1993)). To confirm that the casp-12 overexpression causes apoptosis, the nuclear morphology of the cell death induced by casp-12 expression was examined by staining the casp-12L-lacZ transfected Rat-1 cells with anti-B-galactosidase antibody and Hoechst dye 33258. β-galactosidase-positive round cells which had been transfected with casp-12L-lacZ had condensed and fragmented nuclei, characteristic of cells undergoing apoptosis (FIGS. 4A and 4B).

Figure 4C:
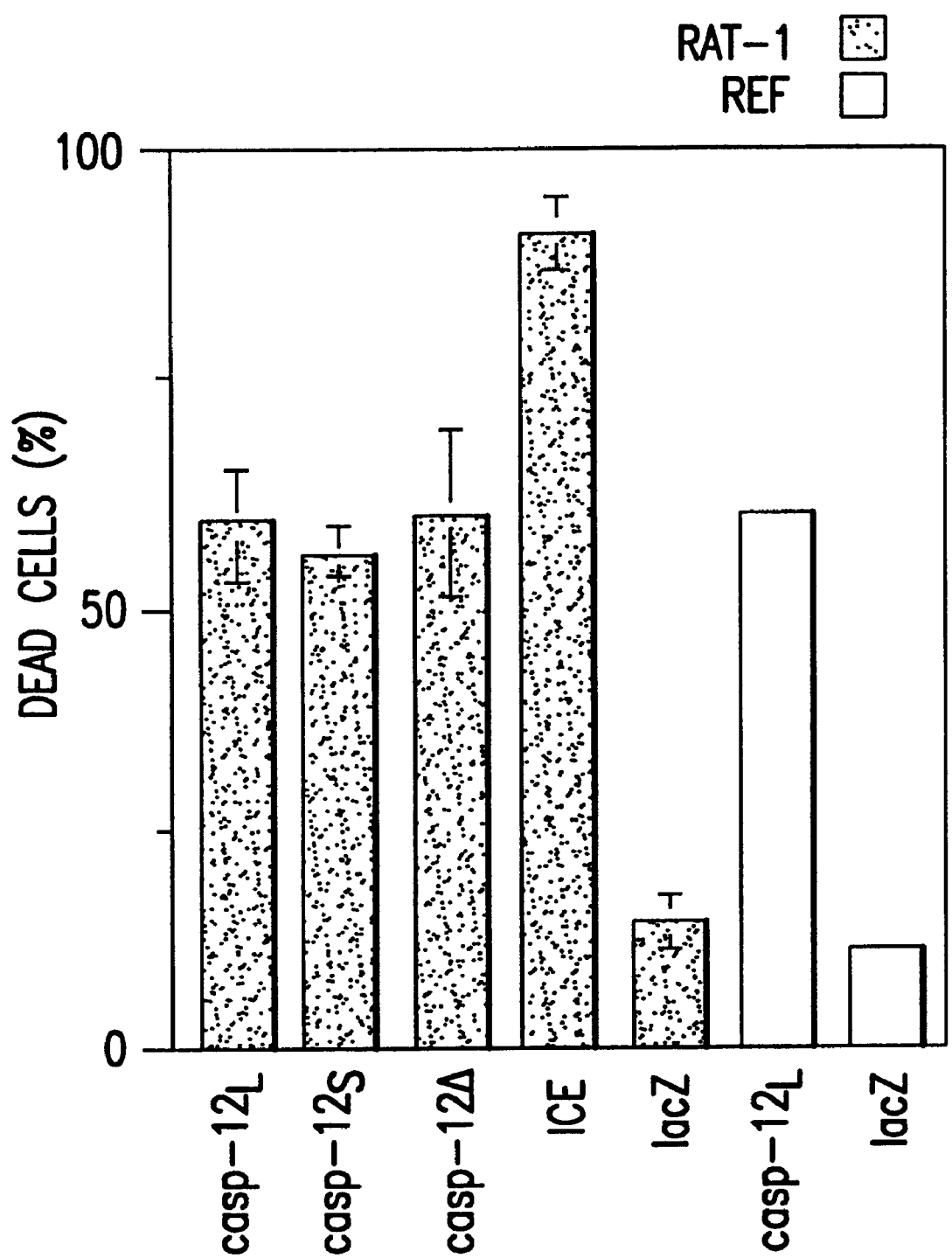

The percentage of cell death induced by caspase-12L and caspase-12S in Rat-1 cells are about 60% (FIG. 4C). A similar result was obtained using primary culture of rat embryonic fibroblasts. About 60% of transfected rat embryonic fibroblasts were round and small (FIG. 4C). Thus, overexpression of casp-12 causes cell death of both an established cell line and primary cells. The apoptotic activity of casp-12, however, is weaker than that of ICE and casp-2, since overexpression of ICE and casp-2 caused over 90% of cells to die (Miura, M., et al., Cell 75:653–660 (1993); Wang, L., et al., Cell 78:739–750 (1994)). In a parallel experiment (FIG. 4C), the same culture of Rat-1 cells were efficiently killed by overexpression of ICE (Miura, M., et al, Cell 75:653–660 (1993)).

The N-terminal pro-domains of the caspase family may have a role in regulating proteolytic activation of the precursor proteins and removal of the pro-domain often results in higher activity (Yuan, J., et al., Cell 75:641–652 (1993); Thornberry, N. A., et al., Nature 356:768–774 (1992); Duan, H., et al., J. Biol. Chem. 271:1621–1625 (1996)). Based upon the sequence homology of caspase-12 with other members of the caspase family, Asp94-Gly95 of caspase-12L was identified as a possible cleavage site (FIG. 1B). To examine the possibility that the pro-domain of caspase-12 may have inhibitory function which reduces cell-killing activity of caspase-12, an expression construct was made which lacked the first 94 amino acids of caspase-12L with remaining Gly95-Asn419 (caspase-12Δ) fused to the lacZ sequence. This casp-12Δ-lacZ fusion construct was transfected into Rat-1 cells and the efficiency of cell-killing was examined by X-gal staining. The truncated construct exhibited a cell-killing activity comparable to that of caspase-12L and caspase-12S (60% dead cells, FIG. 4C). Thus, unlike the pro-domains of other members of the caspase family (Duan, H., et al, J. Biol. Chem. 271:1621–1625 (1996)), the pro-domain of caspase-12 does not appear to have an inhibitory function to the apoptotic activity of caspase-12. The relatively lower cell-killing activity of caspase-12 is likely intrinsic to the caspase-12 protein, rather than due to the inhibition of the pro-domain. This result also shows that the Gly95-Asn419 portion of the caspase-12 protein is sufficient to exhibit its killing activity.

Although the percentages of apoptotic cells induced by overexpression of either full-length caspase-12 or a truncated caspase-12Δ cDNA are comparable to each other, the full-length caspase-12 protein is not active in vitro. It is thus likely that the maturation of caspase-12 in vivo requires other caspases.

EXAMPLE 4

Effects of Cell Death Suppressors on Caspase-12 Cytotoxicity

Cell death induced by overexpression of ICE, casp-2 and casp-11 can be effectively inhibited by bcl-2 (Miura, M., et al., Cell 75:653–660 (1993); Wang, L., et al., Cell 78:739–750 (1994); Wang, S., et al., J. Biol. Chem. 271:20580–20587 (1996)). bcl-2 is a mammalian homolog of the C. elegans ced-9 gene, which is a cell death suppressor in the worm (Ellis, R. E., et al., Annual Review of Cell Biology 7:663–698 (1991)). CrmA is a serpin encoded by cowpox virus which is a discriminatory inhibitor of the caspase family with high affinity for ICE and low affinity for caspase-2 and caspase-3 (Ray, C. A., et al., Cell 69:597–604 (1992), Komiyama, T., et al., J. Biol. Chem. 269:19331–19337 (1994)). Apoptosis induced by ICE and caspase-11 but not caspase-2 can be suppressed by CrmA (Miura, M., et al., Cell 75:653–660 (1993); Wang, L., et al., Cell 78:739–750 (1994); Wang, S., et al., J. Biol. Chem. 271:20580–20587 (1996)). Expression of either bcl-2 or crmA prevents apoptosis of many cell types induced by different stimuli (Miura, M., et al., Cell 75:653–660 (1993); Gagliardini, V., et al., Science 263:97–100 (1994); Tewari, M., and Dixit, V. M., J. Biol. Chem. 270:3255–3260 (1995); Tewari, M., et al., J. Biol. Chem. 270:22605–22708 (1995); Enari, M., et al, Nature 375:78–81 (1995); Los, M., et al., Nature 375:81–83 (1995); Miura, M., et al., Proc. Natl. Acad. Sci. USA 92:8318–8322 (1995)).

Figure 5B:
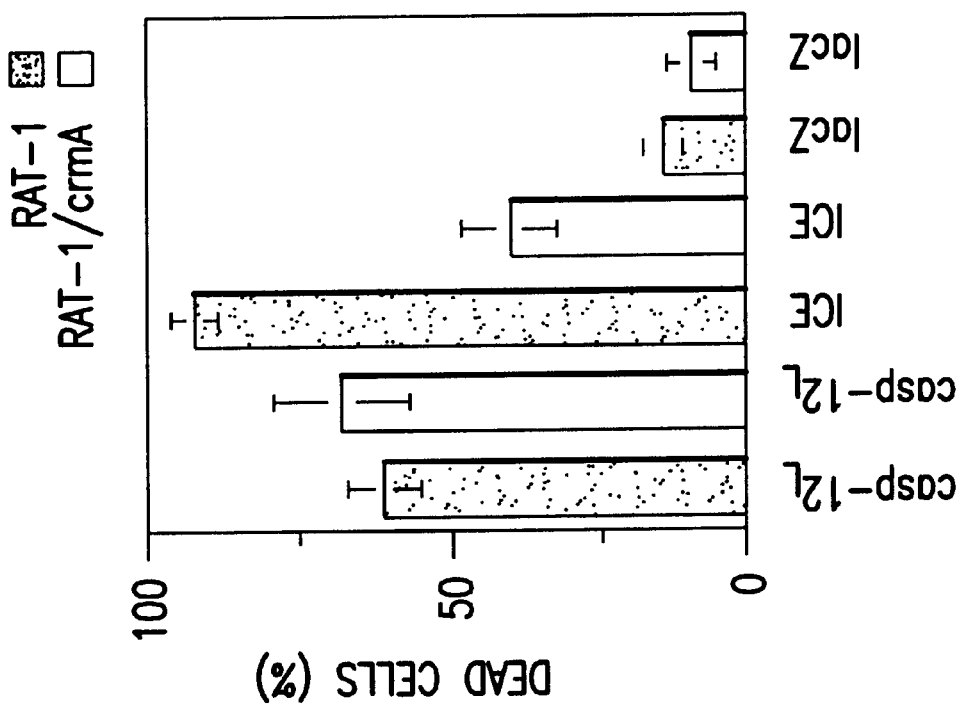
FIGS. 5A–5B. Effect of cell death suppressors on the killing activity of caspase-12.
Figure 5A:
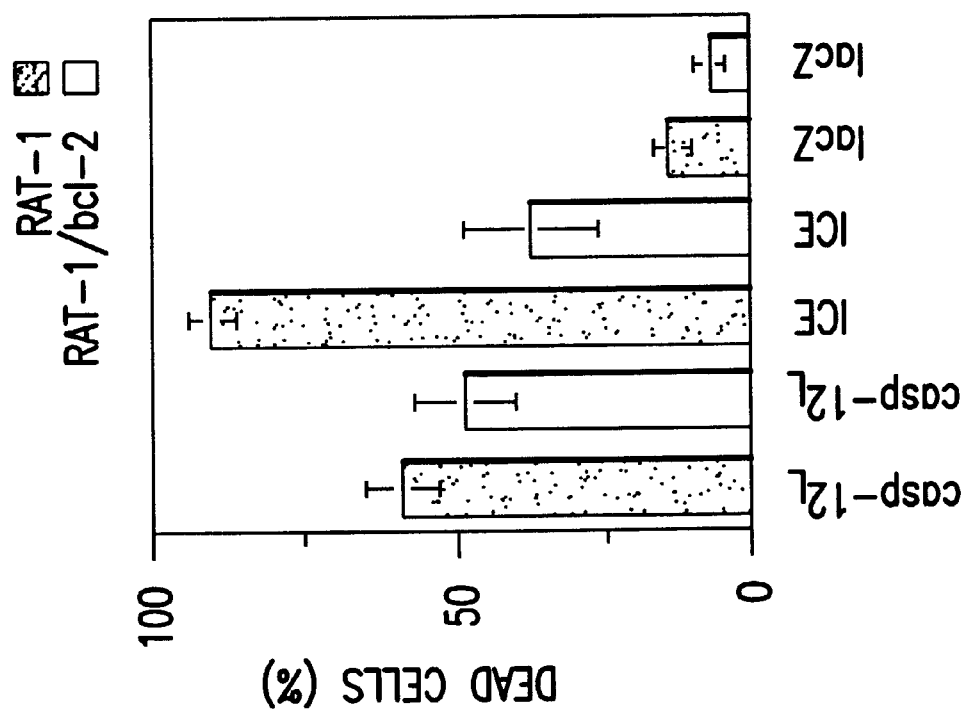

To determine if expression of bcl-2 and crmA can inhibit apoptosis induced by casp-12 overexpression, casp-12L-lacZ fusion construct was transfected into stable cell lines of Rat-1 that overexpresses either bcl-2 or crmA (Miura, M., et al., Cell 75:653–660 (1993)). Cell death was assayed as described above (Example 3). The results showed that the cell death induced by overexpression of casp-12 can be only very weakly inhibited by Bcl-2 (FIG. 5A) but not by CrmA (FIG. 5B). The magnitude of the bcl-2 suppression against toxicity of casp-12 overexpression was about 10% (60% for Rat-1, 50% for Rat-1/bcl-2) which is much smaller than that observed for ICE and casp-2 (FIG. 5A; Wang, L., et al., Cell 78:739–750 (1994)). Statistical analysis suggests that the suppression of caspase-12 by Bcl-2 is not significant with the t-value of 0.35 (P<0.05). Although the ICE-induced apoptosis was suppressed by 50% in Rat-1/crmA cells (Wang, L., et al., Cell 78:739–750 (1994)), caspase-12-induced apoptosis is not suppressed in the same stable cell line (FIG. 5B).

CrmA is known to be a suicide substrate, which forms an equimolar complex with ICE (Komiyama, T., et al., J. Biol. Chem. 269:19331–19337 (1994)). The results thus indicate that although caspase-12 may belong to the ICE subfamily, its substrate specificity is quite different from that of ICE. It has been found that another virus inhibitor for the caspase family, baculovirus p35, could not efficiently suppress the cell-killing activity of caspase-12 (N. Morishima et al., unpublished data). As p35 is an effective inhibitor of ICE, caspase-2 and caspase-3 (Xue, D., and Horvitz, H. R., Nature 377:248–251 (1995)), the substrate specificity of caspase-12 appears to be unique among the members of the caspase family.

Unlike ICE, casp-2 and casp-11, cytotoxicity of casp-12 overexpression was not effectively suppressed by Bcl-2. Thus, caspase-12 may control apoptotic pathways that are not sensitive to the inhibition of Bcl-2. Although Bcl-2 is a potent inhibitor of cell death under many circumstances, some types of cell death have been shown to be resistant to Bcl-2 action. For example, Fas-induced apoptosis is not inhibitable by Bcl-2 in several cell types examined (Memon, S. A., et al., J. Immunol. 155:4644–4652 (1995); Strasser, A., et al., The EMBO Journal 14:6136–6147 (1995)). Caspase-12 could be involved in such Bcl-2 resistant cell death pathway. Alternatively, caspase-12 may control a step which is downstream from the point of Bcl-2 inhibition in the apoptosis pathway. This hypothesis will predict that ICE, caspase-2 and caspase-11 activate apoptosis before or at the step inhibitable by Bcl-2 whereas caspase-12 activates apoptosis after that step. Armstrong et al. (Armstrong, R. C., et al., J. Biol. Chem. 271:16850–16855 (1996)) have shown that Bcl-2 prevents pro-caspase-3 processing. It is thus probable that downstream effectors activated by caspase-3 are insensitive to Bcl-2. The evidence shows that pro-caspase-12 can be cleaved by caspase-3 while caspase-12 cannot efficiently cleave other caspases tested.

EXAMPLE 5

Cell Type Specificity of Caspase-12 Cytotoxicity

Figure 6:
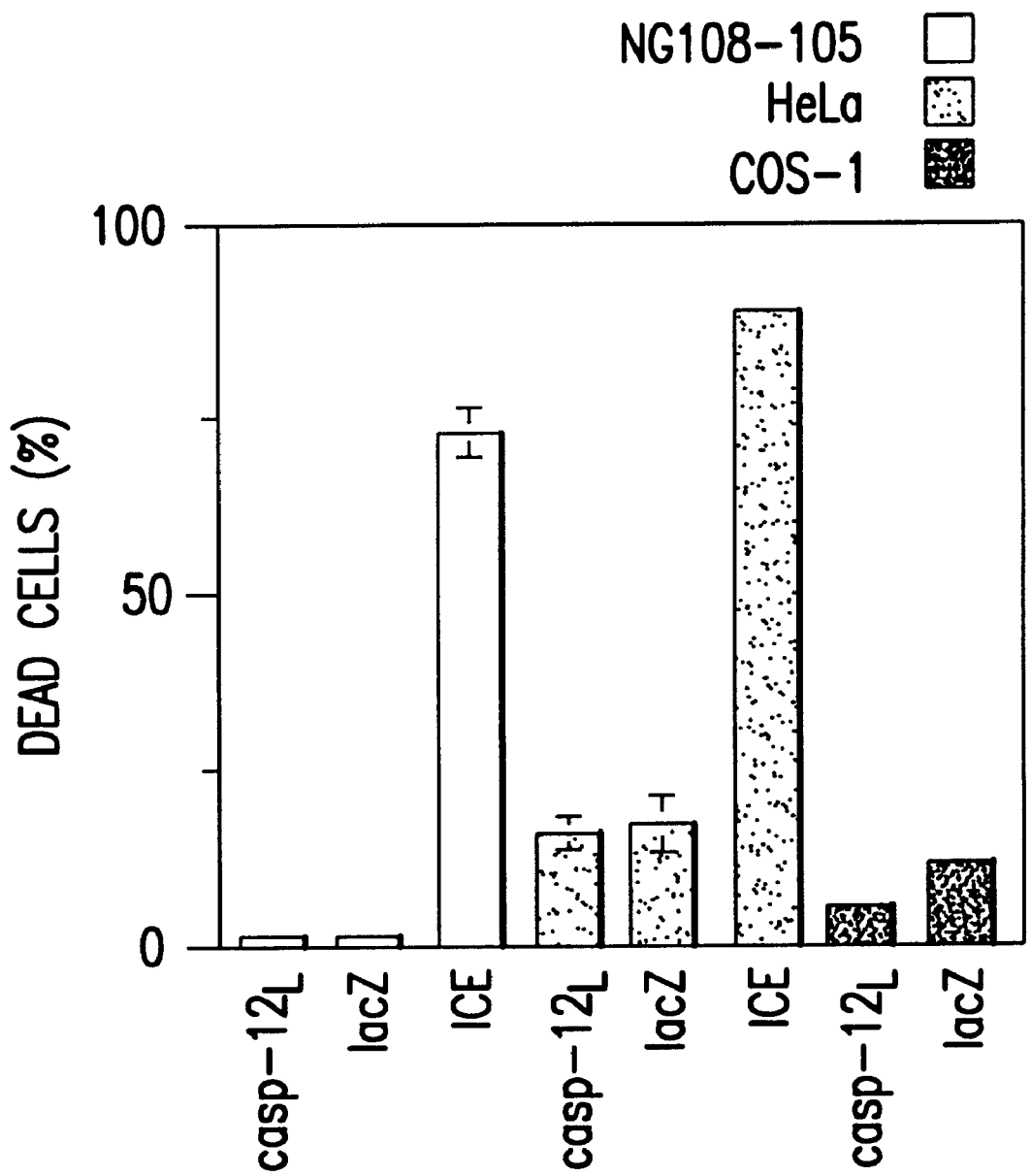
FIG. 6. The cell type specificity of caspase-12-induced cell killing activity. NG108-15, HeLa and COS-1 cells were transfected with casp-12L-lacZ, casp-12S-LacZ, lacZ or ICE-lacZ. Staining of transfectants were done and the data are presented as in FIG. 4C.

The cytotoxic effects of caspase-12 exhibited cell type specificity. The casp-12L-LacZ constructs were transfected into NG108-15, HeLa and COS-1 cells and cell killing effects were assayed to see if caspase-12 kills tumor cell lines as well as Rat-1 fibroblast cells. The results showed that these tumor cell lines are resistant to apoptosis induced by casp-12L expression (FIG. 6). COS-1 cells were established by transformation of monkey kidney cells with SV40 (Gluzman, Y., Cell 23:175–182 (1981)) and are resistant to apoptosis induced by overexpression of ICE and casp-2 (Wang, L., et al., Cell 78:739–750 (1994)). The neuroblastoma/glioma hybrid cell line NG108-15 and HeLa cells are sensitive, however, to apoptosis induced by overexpression of ICE and casp-2 (Wang, L., et al., Cell 78:739–750 (1994)). Control experiments using Ice-lacZ construct showed that overexpression of ICE induced apoptosis of both tumor cell lines effectively under the same experimental conditions (about 70% dead cells as to NG108-15 and 90% for HeLa). These results suggest that the apoptosis inducing activity of caspase-12 may be more sensitive to transformation status of cells than that of ICE and caspase-2.

Caspase-12 is unique among the caspases because of its cell type specificity; fibroblast cells are sensitive to its overexpression, while tumor cell lines examined are resistant. Therefore, one use of casp-12 may be to specifically kill fibroblast cells. The spectrum of caspase-12 killing activity could be related to regulatory mechanism of cell death. One of the possibilities is that the action spectrum that caspase-12 shows is somehow relevant to difference in terms of cell transformation. Tumor cells may lack either substrates or activators of caspase-12, or tumor cells could have specific inhibitors of caspase-12. An aspect of tumorigenesis now well recognized is that cells lose their ability to undergo apoptosis during tumor progression (Symonds, H., et al., Cell 78:703–711 (1994); White, E. Nature 371:21–22 (1994); Fisher, D. E., Cell 78:539–542 (1994)). Identification of the proteins which interact with caspase-12 is thus important and could provide further insight into both apoptosis and tumorigenesis.

EXAMPLE 6

In vitro Cleavage of Caspase-12

Recent data suggest an ordered activation of caspases (Enari, M., et al., Nature 380:723–725 (1996)). To examine if the caspase-12 protein is a substrate for other members of the caspase family, [$^{35}$S]-labeled caspase-12 precursor was incubated with *Escherichia coli* lysates containing the caspase family members.
Methods
Plasmid Construction Casp-12L was amplified through PCR with the following primers: upstream, 5'-CTG GAT CCG TAT GGC GGC CAG GAG GAC ACA TGA AAG AGA TCC-3' (SEQ ID NO:24); and downstream, 5'-CTC GTC GAC CCA TTC CCG GGA AAA AGG TAG-3' (SEQ ID NO:25). Casp-12Δ was amplified through PCR with the following primers: upstream, 5'-CTC GGT ACC ATG GGA CCT CAG AAG ATA TGT AC-3' (SEQ ID NO:22); and downstream, 5'-CTC CTC GAG CTA ATT CCC GGG AAA AAG G-3' (SEQ ID NO:26). The amplified fragments were cleaved by either BamHI/SalI or KpnI/XhoI, and cloned into pcDNA3.
In vitro Cleavage ICE, casp-2 and casp-3 were cloned into a pET-15b vector (Novagen) and their expression was induced in the presence of 0.2–0.3 mM IPTG (Wang, S., et a., *J. Biol. Chem.* 271:20580–20587 (1996); Cryns, V. L., et al., *J. Biol. Chem.* 271:31277–31282 (1996)). Bacterial lysates containing the ICE-like proteases were prepared as described (Wang, S., et al., *J. Biol. Chem.* 271:20580–20587 (1996); Cryns, V. L., et al., *J. Biol. Chem.* 271:31277–31282 (1996)). [$^{35}$S]-labeled proteins were prepared by in vitro transcription and translation using a TNT coupled reticulocyte lysate system (Promega) and [$^{35}$S]methionine (Amersham). Labeled proteins were incubated at 37° C. with purified caspase-12Δ2 or at 30° C. with *E. coli* lysates containing the caspase family members. The reaction mixture contained 25 mM Hepes (pH 7.5) with 5 mM EDTA, 5 mM dithiothreitol, 10% sucrose, 10 μg/ml leupeptin and 250 μM phenylmethylsulfonyl fluoride. Amount of proteins used for cleavage reaction were: 0.1 μg for partially purified caspase-12Δ2, 25–70 μg for *E. coli* lysate. To inactivate caspase-12Δ2 with thiol reagents, purified caspase-12Δ2 was preincubated with either 1 mM 5, 5'-dithio-bis(2-nitrobenzoic acid) (DTNB) at 25° C. for 60 min or 2 mM iodoaceamide at 0° C. for 60 min in the absence of reducing reagents such as dithiothreitol, and subsequently the enzyme solution was used for reaction with [$^{35}$S]-labeled proteins. For the inhibition experiments using DTNB, dithiothreitol was omitted from reaction mixture. Peptide inhibitors, YVAD-CHO (SEQ ID NO:36) (Thornberry, N. A., et al., *Nature* 356:768–774 (1992)) and DEVD-CHO (SEQ ID NO:37) (Nicholson, D. W., et al., *Nature* 376:37–43 (1995)) were purchased from Peptide Institute Inc. (Osaka, Japan). Cleavage products were analyzed by either 10- or 15% SDS-polyacrylamide gel electrophoresis. Detection of proteins were done by fluorography using ENLIGHTNING solution (New England Nuclear) as previously described (Cryns, V. L., et al., *J. Biol. Chem.* 271:31277–31282 (1996)).

Figure 7:
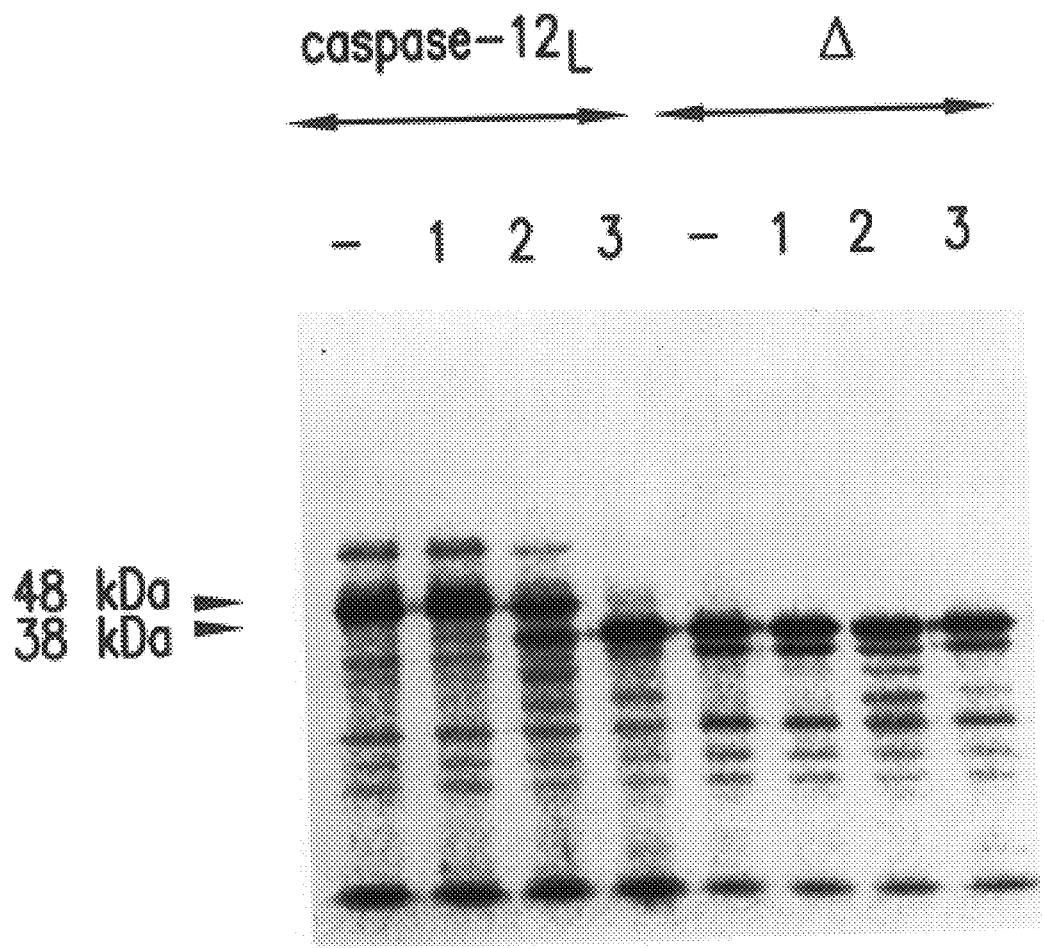
FIG. 7. In vitro cleavage of caspase-12 by other members of the caspase family. [$^{35}$S]-labeled caspase-12, either casp-12L or casp-12Δ, was incubated with E. coli lysate expressing other caspases (1, ICE; 2, caspase-2; 3, caspase-3) for 3 hr at 30° C. Control samples (−) were incubated in the absence of E. coli lysate.

It was found that caspase-2 and caspase-3 can cleave pro-caspase-12 protein, generating smaller fragments of about 40 kDa (FIG. 7). Thus, the precursor form of caspase-12 may be a substrate of several caspases. Among these proteases, caspase-3 was focused on because the probable processing site in pro-caspase-12 (Asp$_{91}$Glu$_{92}$AsP$_{93}$Asp$_{94}$/Gly$_{95}$) (SEQ ID NO:38) matches the consensus sequence for caspase-3 cleavage, DXXD (SEQ ID NO:30); Nicholson, D. W., et al., (SEQ ID NO:36) *Nature* 376:37–43 (1995)). Cleavage of the caspase-12 precursor at this site by caspase-3 would generate a fragment of 38 kDa, whose size is comparable to that of the fragment observed in cleavage experiments with caspase-3. Caspase-2 has a preference for the DXXD (SEQ ID NO:30) sequence, while its cleavage efficiency is also dependent on a P5 residue, which makes this enzyme unique among the caspase family (Van de Craen, M., et al., *FEBS Letters* 403:61–69 (1997)). Cleavage of pro-caspase-12 by caspase-2 generated a fragment of about 40 kDa at a lower cleavage efficiency, compared to caspase-3 digestion.

To examine if caspase-3 cleaves at the peptide bond between Asp94 and Gly95, in vitro cleavage of caspase-12Δ was tried. Casp-12Δ was cloned into pcDNA3 vector with an artificial initiation codon. FIG. 7 shows that the truncated form is identical in size to the fragment generated from pro-caspase-12 by caspase-3 digestion. Caspase-3 treatment of the truncated form did not produce any smaller fragments. These results suggest that the truncated protein does not contain the cleavage site for caspase-3, and that caspase-3 likely cleaves between Asp94 and Gly95.

Caspase-12 can be cleaved by other members of the caspase family (caspase-2, caspase-3). Removal of the N-terminal portion of caspase-12 (Met1 through Asp94) resulted in autoprocessing of the truncated protein when it was expressed in *E. coli*. These results suggest the possibility that caspase-12 can be activated by caspase-3 (or caspase-3-like protease) in vivo through removal of the N-terminal pro-domain. The 38 kDa fragment of caspase-12 generated by the action of caspase-3, however, did not get processed further. Autoprocessing of ICE occurs under particular conditions (Ramage, P., et al., *J. Biol. Chem.* 270:9378–9383 (1995)).

EXAMPLE 7

Protease Activity of Recombinant Caspase-12

To study the enzymatic properties of caspase-12, caspase-12 cDNA was expressed in *E. coli* for protein production.
Methods
Plasmid Construction For production of histidine-tagged proteins, casp-12Δ was inserted into a prokaryotic expression vector, pRSET-A (Invitrogen). Primers used were: upstream, 5'-CTC GGA TCC GGA CCT CAG AAG ATA TGT AC-3' (SEQ ID NO:27); and downstream, 5'-CTC GGA TCC CTA ATT CCC GGG AAA AAG GTA G-3' (SEQ ID NO:28). The amplified fragments were digested with BamHI and inserted into the BamHI site of pRSET-A, which encodes an N-terminal histidine tag. Similarly, bacterial expression plasmid for caspase-12Δ2 (amino acid residues 145–419 of SEQ ID NO:2) was constructed by using another upstream primer, 5'-CTC GGA TCC ACA CTG AAG CTT TGT CCA CG-3' (SEQ ID NO:29).
Production of Recombinant Caspase-12 Protein casp-12Δ and casp-12Δ2 were cloned into a pRSET-A vector (Invitrogen), and the resultant plasmid was introduced into *E. coli* BL21(DE3) pLys. Production of the histidine tagged proteins were induced by 0.1 mM isopropyl-1-thio-β-D-galactopyranoside (IPTG), and the protein was purified with a pET system (Novagen) according to the manufacturer's protocol. Purified protein was stored at −80° C. in 50 mM Tris-HCl (pH7.5) containing 100 mM NaCl and 50% glycerol. N-terminal sequencing was done according to the method of Matsudaira (LeGendre, N., and Matsudaira, P., *Bio Techniques* 6:154–159 (1988)) with an Applied Biosystems 473A Protein Sequencer.

Figure 8A:
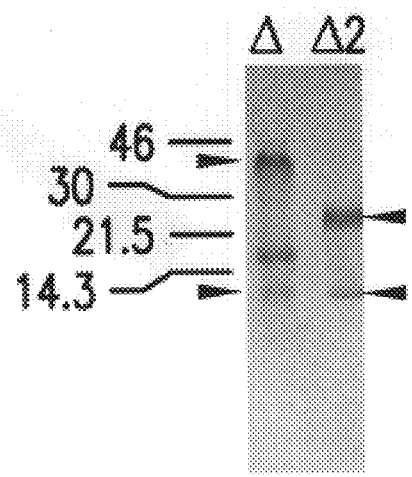
FIGS. 8A–8C Protease activity of caspase-12Δ2.

Full-length caspase-12 protein expressed and purified from *E. coli* was stable without any processing and protease activity in vitro. Thus, a truncated caspase-12 cDNA (caspase-12Δ corresponding to Gly95-Asn419) was expressed in *E. coli* after removal of N-terminal pro-domain coding region and tagged its N-terminal with a His rich sequence. The His-tagged caspase-12Δ protein (approximately 42 kDa including the tag portion of 4.2 kDa) from *E. coli* was partially purified. The purified proteins consisted of three polypeptides of 42 kDa, 17 kDa and 10 kDa (FIG. 8A). Microsequencing of these polypeptide chains revealed that the 42 kDa polypeptide contains the N-terminal His-tag, suggesting that it is an intact form of caspase-12Δ. The 10 kDa polypeptides were a mixture of two polypeptides (roughly equal quantities), one of which has the N-terminal His-tag. The other polypeptide of 10 kDa is the predicted small subunit of caspase-12Δ whose sequence started right after Asp318 in caspase-12 sequence. The 17 kDa polypeptide turned out to be a contaminating *E. coli* His rich protein, the ferric uptake regulation protein. Since there is no reported protease of bacterial origin which shows Asp specificity, it is very likely that the autoprocessing of the caspase-12 protein took place at the position of Asp318 either before or during the purification of the truncated protein. It is also probable that the smaller subunit was obtained by the Ni column chromatography because of its physical association with the intact form of caspase-12Δ.

Figure 8C:
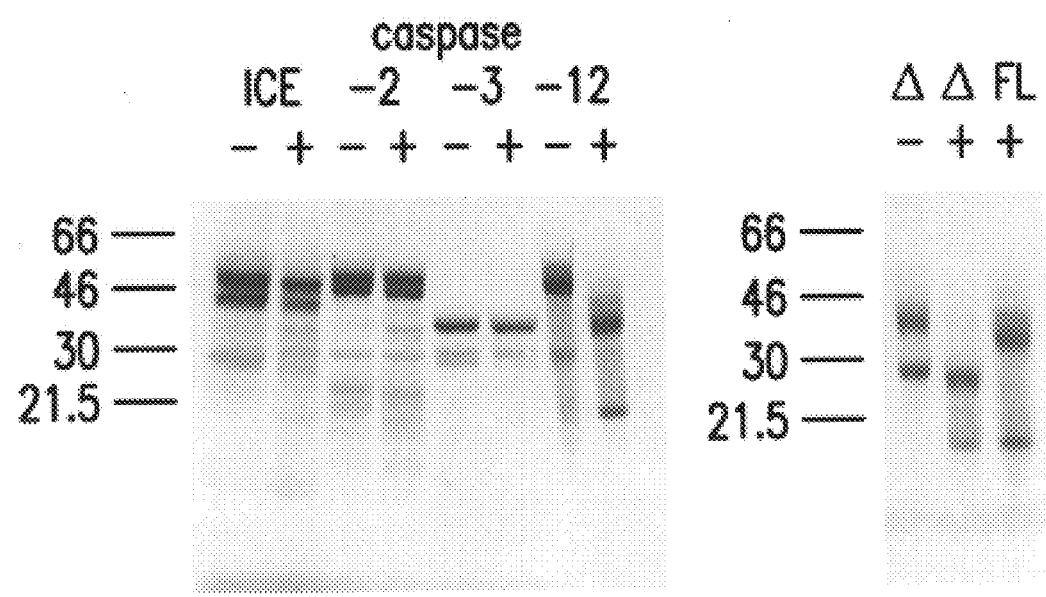
Figure 8B:
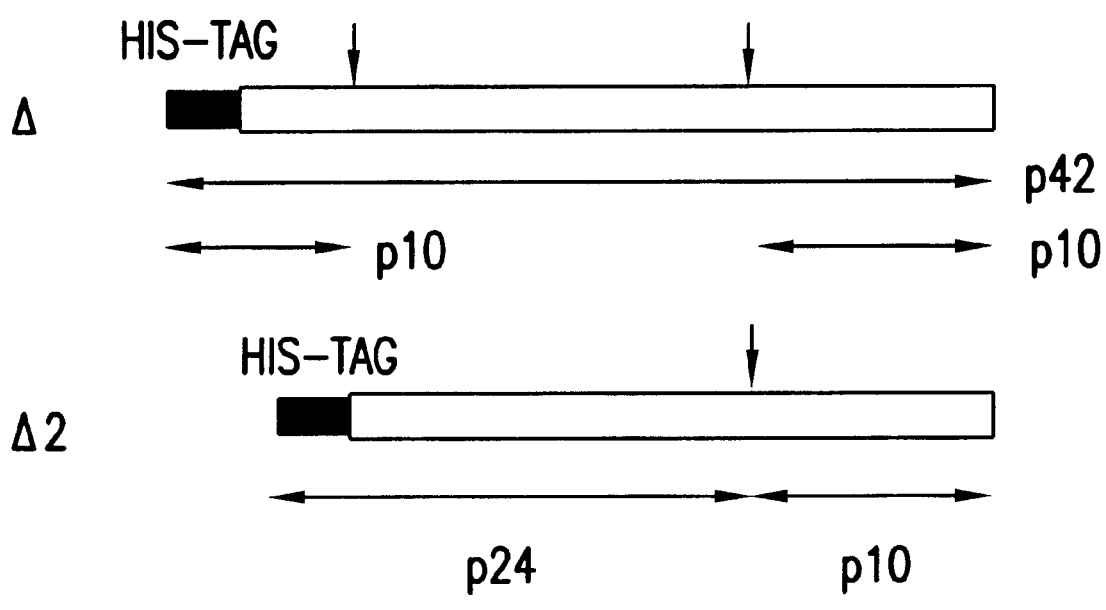

The presence of the smaller tagged protein (10 kDa) suggests that another autoprocessing occurred at an Asp residue which is approximately 50 residues apart from Gly95 (about 90 residues including the tag). It was suspected that the mature p20 subunit of caspase-12 was lost because the N-terminal His tag was removed through autoprocessing (FIG. 8B). To recover the mature form of caspase-12 (p20 and p10), another version of truncated caspase-12 (caspase-12Δ2) which lacked a region of MetI through Asp 144 was expressed. FIG. 8A shows that purified caspase-12Δ2 consists of two major fragments (p24 and p10). p24 had the His tag and the N-terminal of p10 had the sequence starting from Thr319, as revealed by microsequencing. The sequence of p10 indicates that autoprocessing at the Asp318 again occurred in caspase-12Δ2 as well as caspase-12Δ (FIG. 8B). The subunit composition (two polypeptides) and sizes (the 20 kDa subunit tagged with the 4.2 kDa His-rich sequence and the other subunit of 10 kDa) of the purified protein is similar to the mature form of ICE, which consists of 20 kDa and 10 kDa subunits.

The His-tagged caspase-12 recombinant protein was incubated with other members of the caspase family in vitro to determine if caspase-12 can cleave these pro-enzymes. Among the caspase family members examined, caspase-12Δ2 can efficiently process pro-caspase-12 (48 kDa) into fragments. With the disappearance of the intact pro-caspase-12, fragments of about 35 kDa and 13 kDa by caspase-12Δ2 were generated (FIG. 8C). When [$^{35}$S]-labeled caspase-12Δ was incubated with active caspase-12Δ2, the 38 kDa polypeptide was cleaved into 26 kDa and 13 kDa fragments (FIG. 8C). Therefore the truncated polypeptide contains the major cleavage site which divides caspase-12Δ2 into the N-terminal 26 kDa and the C-terminal 13 kDa.

Other members of the family including pro-ICE, pro-caspase-2 and pro-caspase-3, however, were resistant to the recombinant caspase-12Δ2 as only faint bands of cleavage products were visible after incubation with caspase-12Δ2 for the same (FIG. 8C) or longer time period (3 hr). Resistance of ICE, caspase-2 and caspase-3 to caspase-12Δ2 cleavage suggests that these proteases are unlikely to be the substrate for caspase-12 in vivo.

The cleavage of pro-caspase-12 by caspase-12Δ2 was inhibited by thiol reagents. Pretreatment of caspase-12Δ2 with either 5,5'-dithio-bis(2-nitrobenzoic acid) or iodoacetamide completely inhibited its proteolytic activity. This result demonstrates that caspase-12 is a cysteine protease. On the other hand, caspase-12 cleavage activity cannot be inhibited by up to 10 μM YVAD-CHO, the peptide inhibitor with a preference for ICE (Thornberry, N. A., et al., *Nature* 356:768–774 (1992)), or up to 10 μM DEVD-CHO, a peptide inhibitor with a preference for CPP32 (Nicholson, D. W., et al, *Nature* 376:37–43 (1995)). Consistent with this result is that purified caspase-12Δ2 showed little activity for cleavage of pro-IL-1β and poly(ADP-ribose) polymerase, which are the preferred substrates for ICE and caspase-3, respectively. These data suggest that the substrate specificity of caspase-12 mature protein is unique among the known caspases. Therefore, one use of caspase-12 and shortened forms of casp-12, such as casp-12Δ2, may be to specifically cleave proteins for polypeptide mapping.

EXAMPLE 8

Cloning DNA Encoding Caspase-12

A DNA molecule encoding the caspase-12 protein is cloned by hybridizing a desired DNA molecule to the sequence or antisense sequence of, for example, DNA SEQ ID NO:1 or DNA SEQ ID NO:13 under stringent hybridization conditions. Those DNA molecules hybridizing to the probe sequences are selected and transformed into a host cell. The transformants that express caspase-12 are selected and cloned.

One possible set of hybridization conditions for the cloning of the DNA encoding caspase-12 protein is as follows:
1) prehybridizing for 1 hour;
2) hybridizing overnight at 65° C. in the hybridization buffer; and
3) washing once for 15 minutes in 2×SSX at room temperature, then two times for 30 minutes in 0.1×SSC and 0.1% SDS at 60° C.

EXAMPLE 9

Molecular Weight Markers

The caspase-12 proteins produced recombinantly are purified by routine methods in the art (*Current Protocols in Molecular Biology*, Vol. 2, Chap. 10, John Wiley & Sons, Publishers (1994)). Because the deduced amino acid sequence is known, the molecular weight of these proteins can be precisely determined, and the proteins can be used as molecular weight markers for gel electrophoresis. The calculated molecular weight of the full length caspase-12 protein based on the deduced amino acid sequence is 48 kDa.

EXAMPLE 10

Treatment of Cells with Caspase-12

Since caspase-12 can induce programmed cell death (see, Example 3), caspase-12 is used to modulate cell death in a cell. This is accomplished by contacting a cell with a caspase-12 polypeptide. Caspase-12L, caspase 12S, caspase-12Δ, or caspase-12Δ2 is used for this purpose.

All art mentioned herein is incorporated by reference into the disclosure. Having now fully described the invention by way of illustration and example for purposes of clarity and understanding, it will be apparent to those of ordinary skill in the art that certain changes and modifications may be made in the disclosed embodiments and such modifications are intended to be within the scope of the present invention.

What is claimed is:

1. An isolated nucleic acid molecule at least 90% identical to a nucleic acid molecule selected from the group consisting of:
   (a) a nucleic acid molecule consisting of a nucleotide sequence encoding the amino acid sequence of caspase-12S as shown in FIG. 9 (SEQ ID NO: 14);
   (b) a nucleic acid molecule consisting of a nucleotide sequence encoding the amino acid sequence of caspase-12S as encoded by the cDNA clone contained in ATCC Deposit No. 209710;
   (c) a nucleic acid molecule consisting of the nucleotide sequence of caspase-12S as shown in FIG. 9 (SEQ ID NO:13);
   (d) a nucleic acid molecule consisting of a nucleotide sequence encoding caspase-12Δ (amino acid residues 95 to 419 of SEQ ID NO:2); and
   (e) a nucleic acid molecule consisting of a nucleotide sequence encoding caspase-12Δ2 (amino acid residues 145 to 419 of SEQ ID NO:2),
wherein said nucleic acid encodes a polypeptide that increases apoptosis.

2. The nucleic acid molecule of claim 1, wherein said nucleic acid molecule consists of a nucleotide sequence encoding the amino acid sequence of caspase-12S as shown in FIG. 9 (SEQ ID NO:14).

3. The nucleic acid molecule of claim 1, wherein said nucleic acid molecule consists of a nucleotide sequence encoding the amino acid sequence of caspase-12S as encoded by the cDNA clone contained in ATCC Deposit No. 209710.

4. The nucleic acid molecule of claim 1, wherein said nucleic acid molecule consists of the nucleotide sequence of caspase-12S as shown in FIG. 9 (SEQ ID NO:14).

5. The nucleic acid molecule of claim 1, wherein said nucleic acid molecule consists nucleotide sequence encoding caspase-12Δ (amino acid residues 95 to 419 of SEQ ID NO:2).

6. The nucleic acid molecule of claim 1, wherein said nucleic acid molecule consists of a nucleotide sequence encoding caspase-12Δ2 (amino acid residues 145 to 419 of SEQ ID NO:2).

7. A nucleic acid molecule which hybridizes under stringent conditions to the nucleic acid molecule of claim 1, wherein said stringent hybridization conditions comprise:

(i) prehybridizing;

(ii) hybridizing overnight at 65° C. in the hybridization buffer; and (iii) washing once for 15 minutes in 2×SSC at room temperature, then two times for 30 minutes in 0.1×SSC and 0.1% SDS at 60° C., wherein said nucleic acid encodes a polypeptide that increases apoptosis.

8. An isolated nucleic acid molecule encoding a caspase-12S polypeptide, said nucleic acid molecule prepared by a process comprising:

(a) hybridizing a population of nucleic acid molecules to a nucleic acid molecule comprising the sense or anti-sense nucleotide sequence of SEQ ID NO:13, wherein the hybridization is performed under stringent hybridization conditions, wherein said stringent hybridization conditions comprise:

(i) prehybridizing;

(ii) hybridizing overnight at 65° C. in the hybridization buffer; and (iii) washing once for 15 minutes in 2×SSC at room temperature, then two times for 30 minutes in 0.1× SSC and 0.1% SDS at 60° C., (b) selecting those nucleic acid molecules of said population that hybridize to said nucleic acid molecule comprising the sense or antisense nucleotide sequence of SEQ ID NO:13; and (c) selecting nucleic acid molecules of (b) that encode caspase-12S, wherein said nucleic acid encodes a polypeptide that increases apoptosis.

9. A vector comprising the nucleic acid molecule of claim 1.

10. A host transformed with the vector of claim 9.

11. A method for making a caspase-12 polypeptide, comprising:

(a) inserting a nucleic acid molecule of claim 1 into a vector;

(b) transforming a host with said vector; and (c) culturing said host under conditions to induce expression of the caspase-12 polypeptide.

12. A method for selectively killing fibroblast cells comprising transfecting said cells with a vector of claim 9.

13. An isolated nucleic acid molecule at least 90% identical to a nucleic acid molecule consisting of a nucleotide sequence hybridizing under stringent conditions to the complement of (a), (b), (c), (d), or (e) of claim 1, and further wherein said stringent hybridization conditions comprise:

(i) prehybridizing;

(ii) hybridizing overnight at 65° C. in the hybridization buffer; and (iii) washing once for 15 minutes in 2×SSC at room temperature, then two times for 30 minutes in 0.1×SSC and 0.1% SDS at 60° C., wherein said nucleic acid encodes a polypeptide that increases apoptosis.

14. A nucleic acid construct comprising a nucleic acid molecule encoding a caspase-12S polypeptide operably linked to a heterologous promoter, wherein said caspase-12S polypeptide is encoded by a nucleic acid molecule at least 90% identical to a nucleic acid molecule selected from the group consisting of:

(a) a nucleic acid molecule consisting of a nucleotide sequence encoding the amino acid sequence of caspase-12S as shown in FIG. 9 (SEQ ID NO:14);

(b) a nucleic acid molecule consisting of a nucleotide sequence encoding the amino acid sequence of caspase12S as encoded by the cDNA clone contained in ATCC Deposit No. 209710; and (c) a nucleic acid molecule consisting of the nucleotide sequence of caspase-12S as shown in FIG. 9 (SEQ ID NO:13);

wherein said nucleic acid encodes a polypeptide that increases apoptosis.

15. A nucleic acid construct comprising a nucleic acid molecule encoding a caspase-12Δ polypeptide operably linked to a heterologous promoter, wherein said caspase-12Δ polypeptide is encoded by a nucleic acid molecule at least 90% identical to a nucleic acid molecule consisting of a nucleotide sequence encoding the amino acid residues 95 to 419 of SEQ ID NO:14 and encodes a polypeptide that increases apoptosis.

16. A nucleic acid construct comprising a nucleic acid molecule encoding a caspase-12Δ2 polypeptide operably linked to a heterologous promoter, wherein said caspase-12Δ2 polypeptide is encoded by a nucleic acid molecule at least 90% identical to a nucleic acid molecule consisting of a nucleotide sequence encoding the amino acid residues 145 to 419 of SEQ ID NO:14 and encodes a polypeptide that increases apoptosis.

* * * * *

SEQUENCE LISTING

```
<160> NUMBER OF SEQ ID NOS: 38

<210> SEQ ID NO 1
<211> LENGTH: 1402
<212> TYPE: DNA
<213> ORGANISM: Artificial Sequence
<220> FEATURE:
<221> NAME/KEY: CDS
<222> LOCATION: (45)..(1301)
<220> FEATURE:
<223> OTHER INFORMATION: Description of Artificial Sequence: Caspase-12
      cDNA

<400> SEQUENCE: 1
cttttttttt tttttttttt tatgtcctgg agtcctgcac agcc atg gcg gcc agg        56
                                                 Met Ala Ala Arg
                                                   1 agg aca cat gaa aga gat cca atc tac aag atc aaa ggt ttg gcc aag       104
Arg Thr His Glu Arg Asp Pro Ile Tyr Lys Ile Lys Gly Leu Ala Lys
  5                  10                  15                  20 gac atg ctg gat ggg gtt ttt gat gac ctg gtg gag aag aat gtt tta       152
Asp Met Leu Asp Gly Val Phe Asp Asp Leu Val Glu Lys Asn Val Leu
                 25                  30                  35 aat gga gat gag tta ctc aaa ata ggg gaa agt gcg agt ttc atc ctg       200
Asn Gly Asp Glu Leu Leu Lys Ile Gly Glu Ser Ala Ser Phe Ile Leu
             40                  45                  50 aac aag gct gag aat ctg gtt gag aac ttc tta gag aaa aca gac atg       248
Asn Lys Ala Glu Asn Leu Val Glu Asn Phe Leu Glu Lys Thr Asp Met
         55                  60                  65
```

```
gca gga aaa ata ttt gct ggc cac att gcc aat tcc cag gaa cag ctg      296
Ala Gly Lys Ile Phe Ala Gly His Ile Ala Asn Ser Gln Glu Gln Leu
     70              75                  80 agt tta caa ttt tct aat gat gag gat gat gga cct cag aag ata tgt      344
Ser Leu Gln Phe Ser Asn Asp Glu Asp Asp Gly Pro Gln Lys Ile Cys
 85              90                  95                 100 aca cct tct tct cca tca gaa tcc aag aga aaa gta gag gat gat gaa      392
Thr Pro Ser Ser Pro Ser Glu Ser Lys Arg Lys Val Glu Asp Asp Glu
                105                 110                 115 atg gag gta aat gct gga ttg gcc cat gaa tca cat cta atg ctg aca      440
Met Glu Val Asn Ala Gly Leu Ala His Glu Ser His Leu Met Leu Thr
            120                 125                 130 gct cct cat gga ctc cag agc tca gaa gtc caa gat aca ctg aag ctt      488
Ala Pro His Gly Leu Gln Ser Ser Glu Val Gln Asp Thr Leu Lys Leu
        135                 140                 145 tgt cca cgt gat cag ttt tgt aag ata aag aca gaa agg gca aaa gag      536
Cys Pro Arg Asp Gln Phe Cys Lys Ile Lys Thr Glu Arg Ala Lys Glu
    150                 155                 160 ata tat cca gtg atg gag aag gag gga cga aca cgt ctg gct ctc atc      584
Ile Tyr Pro Val Met Glu Lys Glu Gly Arg Thr Arg Leu Ala Leu Ile
165                 170                 175                 180 atc tgc aac aaa aag ttt gac tac ctt ttt gat aga gat aat gct gat      632
Ile Cys Asn Lys Lys Phe Asp Tyr Leu Phe Asp Arg Asp Asn Ala Asp
                185                 190                 195 act gac att ttg aac atg caa gaa cta ctt gaa aat ctt gga tac tct      680
Thr Asp Ile Leu Asn Met Gln Glu Leu Leu Glu Asn Leu Gly Tyr Ser
            200                 205                 210 gtg gtg tta aaa gaa aac ctt aca gct cag gaa atg gag aca gag tta      728
Val Val Leu Lys Glu Asn Leu Thr Ala Gln Glu Met Glu Thr Glu Leu
        215                 220                 225 atg cag ttt gct ggc cgt cca gag cac cag tcc tca gac agc aca ttc      776
Met Gln Phe Ala Gly Arg Pro Glu His Gln Ser Ser Asp Ser Thr Phe
    230                 235                 240 ctg gtg ttt atg tcc cat ggc atc ctg gaa gga atc tgt ggg gtg aag      824
Leu Val Phe Met Ser His Gly Ile Leu Glu Gly Ile Cys Gly Val Lys
245                 250                 255                 260 cac cga aac aaa aag cca gat gtt ctt cat gat gac act atc ttc aaa      872
His Arg Asn Lys Lys Pro Asp Val Leu His Asp Asp Thr Ile Phe Lys
                265                 270                 275 att ttc aac aac tct aac tgt cgg agt ctg aga aac aaa ccc aag att      920
Ile Phe Asn Asn Ser Asn Cys Arg Ser Leu Arg Asn Lys Pro Lys Ile
            280                 285                 290 ctc atc atg cag gcc tgc aga ggc aga tat aat gga act att tgg gta      968
Leu Ile Met Gln Ala Cys Arg Gly Arg Tyr Asn Gly Thr Ile Trp Val
        295                 300                 305 tcc aca aac aaa ggg ata gcc act gct gat aca gat gag gaa cgt gtg     1016
Ser Thr Asn Lys Gly Ile Ala Thr Ala Asp Thr Asp Glu Glu Arg Val
    310                 315                 320 ttg agc tgt aaa tgg aat aat agt ata aca aag gcc cat gtg gag aca     1064
Leu Ser Cys Lys Trp Asn Asn Ser Ile Thr Lys Ala His Val Glu Thr
325                 330                 335                 340 gat ttc att gct ttc aaa tct tct acc cca cat aat att tct tgg aag     1112
Asp Phe Ile Ala Phe Lys Ser Ser Thr Pro His Asn Ile Ser Trp Lys
                345                 350                 355 gta ggc aag act ggt tcc ctc ttc att tcc aaa ctc att gac tgc ttc     1160
Val Gly Lys Thr Gly Ser Leu Phe Ile Ser Lys Leu Ile Asp Cys Phe
            360                 365                 370 aaa aag tac tgt tgg tgt tat cat ttg gag gaa att ttt cga aag gtt     1208
Lys Lys Tyr Cys Trp Cys Tyr His Leu Glu Glu Ile Phe Arg Lys Val
        375                 380                 385
```

```
caa cac tca ttt gag gtc cca ggt gaa ctg acc cag atg ccc act att    1256
Gln His Ser Phe Glu Val Pro Gly Glu Leu Thr Gln Met Pro Thr Ile
    390             395                 400 gag aga gta tcc atg aca cgc tat ttc tac ctt ttt ccc ggg aat        1301
Glu Arg Val Ser Met Thr Arg Tyr Phe Tyr Leu Phe Pro Gly Asn
405             410                 415 tagcacaggc aactctcatg cagttcacag tcaagtattg ctgtagctga gaagaaaaga  1361
aaattccaag atcccaggat ttttaaatgt gtaaaactt t                       1402

<210> SEQ ID NO 2
<211> LENGTH: 419
<212> TYPE: PRT
<213> ORGANISM: Artificial Sequence
<220> FEATURE:
<223> OTHER INFORMATION: Description of Artificial Sequence: Caspase-12
      protein

<400> SEQUENCE: 2

Met Ala Ala Arg Arg Thr His Glu Arg Asp Pro Ile Tyr Lys Ile Lys
 1               5                  10                  15

Gly Leu Ala Lys Asp Met Leu Asp Gly Val Phe Asp Asp Leu Val Glu
            20                  25                  30

Lys Asn Val Leu Asn Gly Asp Glu Leu Leu Lys Ile Gly Glu Ser Ala
        35                  40                  45

Ser Phe Ile Leu Asn Lys Ala Glu Asn Leu Val Glu Asn Phe Leu Glu
    50                  55                  60

Lys Thr Asp Met Ala Gly Lys Ile Phe Ala Gly His Ile Ala Asn Ser
65                  70                  75                  80

Gln Glu Gln Leu Ser Leu Gln Phe Ser Asn Asp Glu Asp Asp Gly Pro
                85                  90                  95

Gln Lys Ile Cys Thr Pro Ser Ser Pro Ser Glu Ser Lys Arg Lys Val
            100                 105                 110

Glu Asp Asp Glu Met Glu Val Asn Ala Gly Leu Ala His Glu Ser His
        115                 120                 125

Leu Met Leu Thr Ala Pro His Gly Leu Gln Ser Ser Glu Val Gln Asp
    130                 135                 140

Thr Leu Lys Leu Cys Pro Arg Asp Gln Phe Cys Lys Ile Lys Thr Glu
145                 150                 155                 160

Arg Ala Lys Glu Ile Tyr Pro Val Met Glu Lys Glu Gly Arg Thr Arg
                165                 170                 175

Leu Ala Leu Ile Ile Cys Asn Lys Lys Phe Asp Tyr Leu Phe Asp Arg
            180                 185                 190

Asp Asn Ala Asp Thr Asp Ile Leu Asn Met Gln Glu Leu Leu Glu Asn
        195                 200                 205

Leu Gly Tyr Ser Val Val Leu Lys Glu Asn Leu Thr Ala Gln Glu Met
    210                 215                 220

Glu Thr Glu Leu Met Gln Phe Ala Gly Arg Pro Glu His Gln Ser Ser
225                 230                 235                 240

Asp Ser Thr Phe Leu Val Phe Met Ser His Gly Ile Leu Glu Gly Ile
                245                 250                 255

Cys Gly Val Lys His Arg Asn Lys Lys Pro Asp Val Leu His Asp Asp
            260                 265                 270

Thr Ile Phe Lys Ile Phe Asn Asn Ser Asn Cys Arg Ser Leu Arg Asn
        275                 280                 285

Lys Pro Lys Ile Leu Ile Met Gln Ala Cys Arg Gly Arg Tyr Asn Gly
```

-continued

```
                        290                 295                 300
Thr Ile Trp Val Ser Thr Asn Lys Gly Ile Ala Thr Ala Asp Thr Asp
305                 310                 315                 320

Glu Glu Arg Val Leu Ser Cys Lys Trp Asn Asn Ser Ile Thr Lys Ala
                325                 330                 335

His Val Glu Thr Asp Phe Ile Ala Phe Lys Ser Ser Thr Pro His Asn
            340                 345                 350

Ile Ser Trp Lys Val Gly Lys Thr Gly Ser Leu Phe Ile Ser Lys Leu
        355                 360                 365

Ile Asp Cys Phe Lys Lys Tyr Cys Trp Cys Tyr His Leu Glu Glu Ile
370                 375                 380

Phe Arg Lys Val Gln His Ser Phe Glu Val Pro Gly Glu Leu Thr Gln
385                 390                 395                 400

Met Pro Thr Ile Glu Arg Val Ser Met Thr Arg Tyr Phe Tyr Leu Phe
                405                 410                 415

Pro Gly Asn

<210> SEQ ID NO 3
<211> LENGTH: 5
<212> TYPE: PRT
<213> ORGANISM: Unknown
<220> FEATURE:
<223> OTHER INFORMATION: Description of Unknown Organism: conserved
      pentapeptide

<400> SEQUENCE: 3

Gln Ala Cys Arg Gly
1               5

<210> SEQ ID NO 4
<211> LENGTH: 418
<212> TYPE: PRT
<213> ORGANISM: Unknown
<220> FEATURE:
<223> OTHER INFORMATION: Description of Unknown Organism: Caspase-5

<400> SEQUENCE: 4

Met Phe Lys Gly Ile Leu Gln Ser Gly Leu Asp Asn Phe Val Ile Asn
1               5                   10                  15

His Met Leu Lys Asn Val Ala Gly Gln Thr Ser Ile Gln Thr Leu
            20                  25                  30

Val Pro Asn Thr Asp Gln Lys Ser Thr Ser Val Lys Lys Asp Asn His
            35                  40                  45

Lys Lys Lys Thr Val Lys Met Leu Glu Tyr Leu Gly Lys Asp Val Leu
    50                  55                  60

His Gly Val Phe Met Tyr Leu Ala Lys His Asp Val Leu Thr Leu Lys
65                  70                  75                  80

Glu Glu Glu Lys Lys Tyr Tyr Asp Ala Lys Thr Glu Asp Lys Ala
                85                  90                  95

Leu Ile Leu Val Asp Ser Leu Arg Lys Asn Arg Val Ala His Gln Met
                100                 105                 110

Phe Thr Gln Thr Leu Leu Asn Met Asp Gln Lys Ile Thr Ser Val Lys
            115                 120                 125

Pro Leu Leu Gln Ile Asp Ala Gly Pro Pro Glu Ser Ala Glu Ser Thr
    130                 135                 140

Asn Ile Leu Lys Leu Cys Pro Arg Glu Glu Phe Leu Arg Leu Cys Lys
145                 150                 155                 160
```

```
Lys Asn His Asp Glu Ile Tyr Pro Ile Lys Lys Arg Glu Asp Arg Arg
                165                 170                 175
Arg Leu Ala Leu Ile Ile Cys Asn Thr Lys Phe Asp His Leu Pro Ala
            180                 185                 190
Arg Asn Gly Ala His Tyr Asp Ile Val Gly Met Lys Arg Leu Leu Gln
        195                 200                 205
Gly Leu Gly Tyr Thr Val Val Asp Glu Lys Asn Leu Thr Ala Arg Asp
    210                 215                 220
Met Glu Ser Val Leu Arg Ala Phe Ala Ala Arg Pro Glu His Lys Ser
225                 230                 235                 240
Ser Asp Ser Thr Phe Leu Val Leu Met Ser His Gly Ile Leu Glu Gly
                245                 250                 255
Ile Cys Gly Thr Ala His Lys Lys Lys Pro Asp Val Leu Leu Tyr
            260                 265                 270
Asp Thr Ile Phe Gln Ile Phe Asn Asn Arg Asn Cys Leu Ser Leu Lys
        275                 280                 285
Asp Lys Pro Lys Val Ile Ile Val Gln Ala Cys Arg Gly Glu Lys His
    290                 295                 300
Gly Glu Leu Met Val Arg Asp Ser Pro Ala Ser Leu Ala Val Ile Ser
305                 310                 315                 320
Ser Gln Ser Ser Glu Asn Leu Glu Ala Asp Ser Val Cys Lys Ile His
                325                 330                 335
Glu Lys Lys Asp Phe Ile Ala Phe Cys Ser Ser Ser Pro His Asn Val
            340                 345                 350
Ser Trp Arg Asp Arg Thr Arg Gly Ser Ile Phe Ile Thr Glu Leu Ile
        355                 360                 365
Thr Cys Phe Gln Lys Tyr Ser Cys Cys His Leu Met Glu Ile Phe
    370                 375                 380
Arg Lys Val Gln Lys Ser Phe Glu Val Pro Gln Ala Lys Ala Gln Met
385                 390                 395                 400
Pro Thr Ile Glu Arg Ala Thr Leu Thr Arg Asp Phe Tyr Leu Phe Pro
                405                 410                 415
Gly Asn

<210> SEQ ID NO 5
<211> LENGTH: 404
<212> TYPE: PRT
<213> ORGANISM: Homo sapiens

<400> SEQUENCE: 5

Met Ala Asp Lys Val Leu Lys Glu Lys Arg Lys Leu Phe Ile Arg Ser
 1               5                  10                  15
Met Gly Glu Gly Thr Ile Asn Gly Leu Leu Asp Glu Leu Leu Gln Thr
                20                  25                  30
Arg Val Leu Asn Lys Glu Glu Met Glu Lys Val Lys Arg Glu Asn Ala
            35                  40                  45
Thr Val Met Asp Lys Thr Arg Ala Leu Ile Asp Ser Val Ile Pro Lys
        50                  55                  60
Gly Ala Gln Ala Cys Gln Ile Cys Ile Thr Tyr Ile Cys Glu Glu Asp
65                  70                  75                  80
Ser Tyr Leu Ala Gly Thr Leu Gly Leu Ser Ala Asp Gln Thr Ser Gly
                85                  90                  95
Asn Tyr Leu Asn Met Gln Asp Ser Gln Gly Val Leu Ser Ser Phe Pro
            100                 105                 110
```

```
Ala Pro Gln Ala Val Gln Asp Asn Pro Ala Met Pro Thr Ser Ser Gly
        115                 120                 125

Ser Glu Gly Asn Val Lys Leu Cys Ser Leu Glu Glu Ala Gln Arg Ile
    130                 135                 140

Trp Lys Gln Lys Ser Ala Glu Ile Tyr Pro Ile Met Asp Lys Ser Ser
145                 150                 155                 160

Arg Thr Arg Leu Ala Leu Ile Ile Cys Asn Glu Glu Phe Asp Ser Ile
                165                 170                 175

Pro Arg Arg Thr Gly Ala Glu Val Asp Ile Thr Gly Met Thr Met Leu
                180                 185                 190

Leu Gln Asn Leu Gly Tyr Ser Val Asp Val Lys Lys Asn Leu Thr Ala
            195                 200                 205

Ser Asp Met Thr Thr Glu Leu Glu Ala Phe Ala His Arg Pro Glu His
    210                 215                 220

Lys Thr Ser Asp Ser Thr Phe Leu Val Phe Met Ser His Gly Ile Arg
225                 230                 235                 240

Glu Gly Ile Cys Gly Lys Lys His Ser Glu Gln Val Pro Asp Ile Leu
                245                 250                 255

Gln Leu Met Ala Ile Phe Asn Met Leu Asn Thr Lys Met Cys Pro Ser
            260                 265                 270

Leu Lys Asp Lys Pro Lys Val Ile Ile Ile Gln Ala Cys Arg Gly Asp
            275                 280                 285

Ser Pro Gly Val Val Trp Phe Lys Asp Ser Val Gly Val Ser Gly Asn
    290                 295                 300

Leu Ser Leu Pro Thr Thr Glu Glu Phe Glu Asp Asp Ala Ile Lys Lys
305                 310                 315                 320

Ala His Ile Lys Lys Asp Phe Ile Ala Phe Cys Ser Ser Thr Pro Asp
                325                 330                 335

Asn Val Ser Trp Arg His Pro Thr Met Gly Ser Val Phe Ile Gly Arg
                340                 345                 350

Leu Ile Gly His Met Gln Glu Tyr Ala Cys Ser Cys Asp Val Glu Glu
            355                 360                 365

Ile Phe Arg Lys Val Arg Phe Ser Phe Glu Gln Pro Asp Gly Arg Ala
370                 375                 380

Gln Met Pro Thr Thr Glu Arg Val Thr Leu Thr Arg Cys Phe Tyr Leu
385                 390                 395                 400

Phe Pro Gly His

<210> SEQ ID NO 6
<211> LENGTH: 402
<212> TYPE: PRT
<213> ORGANISM: Mus musculus

<400> SEQUENCE: 6

Met Ala Asp Lys Ile Leu Arg Ala Lys Arg Lys Gln Phe Ile Asn Ser
1               5                   10                  15

Val Ser Ile Gly Thr Ile Asn Gly Leu Leu Asp Glu Leu Leu Glu Lys
            20                  25                  30

Arg Val Leu Asn Gln Glu Glu Met Asp Lys Ile Lys Leu Ala Asn Ile
        35                  40                  45

Thr Ala Met Asp Lys Ala Arg Asp Leu Cys Asp His Val Ser Lys Lys
    50                  55                  60

Gly Ala Pro Ala Ser Gln Ile Phe Ile Thr Tyr Ile Cys Asn Glu Asp
65                  70                  75                  80
```

-continued

```
Cys Tyr Leu Ala Gly Ile Leu Glu Leu Gln Ser Ala Pro Ser Ala Glu
                85                  90                  95

Thr Phe Val Ala Thr Glu Asp Ser Lys Gly His Pro Ser Ser Ser
            100                 105                 110

Glu Thr Lys Glu Glu Gln Asn Lys Glu Asp Gly Thr Phe Pro Gly Leu
        115                 120                 125

Thr Gly Thr Leu Lys Phe Cys Pro Leu Glu Lys Ala Gln Lys Leu Trp
    130                 135                 140

Lys Glu Asn Pro Ser Glu Ile Tyr Pro Ile Met Asn Thr Thr Arg
145                 150                 155                 160

Thr Arg Leu Ala Leu Ile Ile Cys Asn Thr Glu Phe Gln His Leu Ser
                165                 170                 175

Pro Arg Val Gly Ala Gln Val Asp Leu Arg Glu Met Lys Leu Leu Leu
            180                 185                 190

Glu Asp Leu Gly Tyr Thr Val Lys Val Lys Glu Asn Leu Thr Ala Leu
        195                 200                 205

Glu Met Val Lys Glu Val Lys Glu Phe Ala Ala Cys Pro Glu His Lys
    210                 215                 220

Thr Ser Asp Ser Thr Phe Leu Val Phe Met Ser His Gly Ile Gln Glu
225                 230                 235                 240

Gly Ile Cys Gly Thr Thr Tyr Ser Asn Glu Val Ser Asp Ile Leu Lys
                245                 250                 255

Val Asp Thr Ile Phe Gln Met Met Asn Thr Leu Lys Cys Pro Ser Leu
            260                 265                 270

Lys Asp Lys Pro Lys Val Ile Ile Gln Ala Cys Arg Gly Glu Lys
        275                 280                 285

Gln Gly Val Val Leu Leu Lys Asp Ser Val Arg Asp Ser Glu Glu Asp
    290                 295                 300

Phe Leu Thr Asp Ala Ile Phe Glu Asp Asp Gly Ile Lys Lys Ala His
305                 310                 315                 320

Ile Lys Lys Asp Phe Ile Ala Phe Cys Ser Ser Thr Pro Asp Asn Val
                325                 330                 335

Ser Trp Arg His Pro Val Arg Gly Ser Leu Phe Ile Glu Ser Leu Ile
            340                 345                 350

Lys His Met Lys Glu Tyr Ala Trp Ser Cys Asp Leu Glu Asp Ile Phe
        355                 360                 365

Arg Lys Val Arg Phe Ser Phe Glu Gln Pro Lys Glu Arg Leu Gln Met
    370                 375                 380

Pro Thr Ala Asp Arg Val Thr Leu Thr Lys Arg Phe Tyr Leu Phe Pro
385                 390                 395                 400

Gly His

<210> SEQ ID NO 7
<211> LENGTH: 373
<212> TYPE: PRT
<213> ORGANISM: Unknown
<220> FEATURE:
<223> OTHER INFORMATION: Description of Unknown Organism: Caspase-11

<400> SEQUENCE: 7

Met Ala Glu Asn Lys His Pro Asp Lys Pro Leu Lys Val Leu Glu Gln
 1               5                  10                  15

Leu Gly Lys Glu Val Leu Thr Glu Tyr Leu Lys Lys Leu Val Gln Ser
            20                  25                  30

Asn Val Leu Lys Leu Lys Glu Glu Asp Lys Gln Lys Phe Asn Trp Ala
```

-continued

```
                 35                  40                  45
Glu Arg Ser Asp Lys Arg Met Val Phe Val Asp Ala Met Lys Lys Lys
             50                  55                  60

His Ser Lys Val Gly Glu Met Leu Leu Gln Thr Phe Phe Ser Val Asp
 65                  70                  75                  80

Pro Gly Ser His His Gly Glu Ala Asn Leu Glu Met Glu Pro Lys
                 85                  90                  95

Lys Ser Leu Met Thr Leu Lys Leu Cys Ser Pro Glu Glu Phe Thr Arg
            100                 105                 110

Leu Cys Arg Glu Lys Thr Gln Glu Ile Tyr Pro Ile Lys Glu Ala Asn
            115                 120                 125

Gly Arg Thr Arg Lys Ala Leu Ile Ile Cys Asn Thr Glu Phe Lys His
        130                 135                 140

Leu Ser Leu Arg Tyr Gly Ala Lys Phe Asp Ile Ile Gly Met Lys Gly
145                 150                 155                 160

Leu Leu Glu Asp Leu Gly Tyr Asp Val Val Val Lys Glu Asn Leu Thr
                165                 170                 175

Ala Glu Gly Met Glu Ser Glu Met Lys Asp Phe Ala Ala Leu Ser Glu
            180                 185                 190

Lys Gln Thr Ser Asp Ser Thr Phe Leu Val Leu Met Ser His Gly Thr
        195                 200                 205

Leu His Gly Ile Cys Gly Thr Met His Ser Glu Lys Thr Pro Asp Val
    210                 215                 220

Leu Gln Tyr Asp Thr Ile Tyr Gln Ile Phe Asn Asn Cys His Cys Pro
225                 230                 235                 240

Gly Leu Arg Asp Lys Pro Lys Val Ile Ile Val Gln Ala Cys Arg Gly
                245                 250                 255

Gly Met Ser Gly Glu Met His Ile Arg Glu Ser Ser Lys Pro Gln Leu
            260                 265                 270

Cys Arg Gly Val Asp Leu Pro Arg Asn Met Glu Ala Asp Ala Val Lys
        275                 280                 285

Leu Ser His Val Lys Lys Asp Phe Ile Ala Phe Tyr Ser Thr Thr Pro
    290                 295                 300

His His Leu Ser Tyr Arg Asp Lys Thr Gly Gly Ser Tyr Phe Ile Thr
305                 310                 315                 320

Arg Leu Ile Ser Cys Phe Arg Lys His Ala Cys Ser Cys His Leu Phe
                325                 330                 335

Asp Ile Phe Leu Lys Val Gln Gln Ser Phe Glu Lys Ala Ser Ile His
            340                 345                 350

Ser Gln Met Pro Thr Ile Asp Arg Ala Thr Leu Thr Arg Tyr Phe Tyr
        355                 360                 365

Leu Phe Pro Gly Asn
    370
```

<210> SEQ ID NO 8
<211> LENGTH: 379
<212> TYPE: PRT
<213> ORGANISM: Unknown
<220> FEATURE:
<223> OTHER INFORMATION: Description of Unknown Organism: Caspase-4

<400> SEQUENCE: 8

```
Met Ala Glu Gly Asn His Arg Lys Lys Pro Leu Lys Val Leu Glu Ser
 1               5                  10                  15

Leu Gly Lys Asp Phe Leu Thr Gly Val Leu Asp Asn Leu Glu Val Gln
```

```
                    20                  25                  30
        Asn Val Leu Met Trp Lys Lys Glu Glu Lys Lys Tyr Tyr Asp Ala
                        35                  40                  45
        Lys Thr Glu Asp Lys Val Arg Ala Met Ala Asp Ser Met Gln Glu Lys
                    50                  55                  60
        Gln Arg Met Ala Gly Gln Met Leu Leu Gln Thr Phe Phe Asn Ile Asp
        65                  70                  75                  80
        Gln Ile Ser Pro Asn Lys Lys Ala His Pro Asn Met Glu Ala Gly Pro
                        85                  90                  95
        Pro Glu Ser Gly Glu Ser Thr Asp Ala Leu Lys Leu Cys Pro His Glu
                    100                 105                 110
        Glu Phe Leu Arg Leu Cys Lys Glu Arg Ala Glu Ile Tyr Pro Ile
                    115                 120                 125
        Lys Glu Arg Asn Asn Arg Thr Arg Leu Ala Leu Ile Ile Cys Asn Thr
                    130                 135                 140
        Glu Phe Asp His Leu Pro Pro Arg Asn Gly Ala Asp Phe Asp Ile Thr
        145                 150                 155                 160
        Gly Met Lys Glu Leu Leu Leu Leu Glu Gly Leu Asp Tyr Ser Val Asp
                        165                 170                 175
        Val Glu Glu Asn Leu Thr Ala Arg Asp Met Glu Ser Ala Leu Arg Ala
                    180                 185                 190
        Phe Ala Thr Arg Pro Glu His Lys Ser Ser Asp Ser Thr Phe Leu Val
                    195                 200                 205
        Leu Met Ser His Gly Ile Leu Glu Gly Ile Cys Gly Thr Val His Asp
            210                 215                 220
        Glu Lys Lys Pro Asp Val Leu Leu Tyr Asp Thr Ile Phe Gln Ile Phe
        225                 230                 235                 240
        Asn Asn Arg Asn Cys Leu Ser Leu Lys Asp Lys Pro Lys Val Ile Ile
                        245                 250                 255
        Val Gln Ala Cys Arg Gly Ala Met Arg Gly Glu Leu Met Val Arg Asp
                    260                 265                 270
        Ser Pro Ala Ser Leu Glu Val Ala Ser Ser Gln Ser Ser Glu Asn Leu
                    275                 280                 285
        Glu Glu Asp Ala Val Tyr Lys Thr His Val Glu Lys Asp Phe Ile Ala
                    290                 295                 300
        Phe Cys Ser Ser Thr Pro His Asn Val Ser Trp Arg Asp Ser Thr Met
        305                 310                 315                 320
        Gly Ser Ile Phe Ile Thr Gln Leu Ile Thr Cys Phe Gln Lys Tyr Ser
                        325                 330                 335
        Trp Cys Cys His Leu Glu Glu Val Phe Arg Lys Val Gln Gln Ser Phe
                    340                 345                 350
        Glu Thr Pro Arg Ala Lys Ala Gln Met Pro Thr Ile Glu Arg Leu Ser
                    355                 360                 365
        Met Thr Arg Tyr Phe Tyr Leu Phe Pro Gly Asn
                    370                 375

<210> SEQ ID NO 9
<211> LENGTH: 13
<212> TYPE: PRT
<213> ORGANISM: Caenorhabditis elegans

<400> SEQUENCE: 9

His Gly Cys Arg Gln Arg Ser Val Trp Asn Ser Ser Gly
  1               5                  10
```

<210> SEQ ID NO 10
<211> LENGTH: 435
<212> TYPE: PRT
<213> ORGANISM: Unknown
<220> FEATURE:
<223> OTHER INFORMATION: Description of Unknown Organism: Caspase-2

<400> SEQUENCE: 10

```
Met Ala Ala Asp Arg Gly Arg Arg Ile Leu Gly Val Cys Gly Met His
  1               5                  10                  15

Pro His His Gln Glu Thr Leu Lys Lys Asn Arg Val Val Leu Ala Lys
             20                  25                  30

Gln Leu Leu Leu Ser Glu Leu Leu Glu His Leu Leu Glu Lys Asp Ile
         35                  40                  45

Ile Thr Leu Glu Met Arg Glu Leu Ile Gln Ala Lys Val Gly Ser Phe
     50                  55                  60

Ser Gln Asn Val Glu Leu Leu Asn Leu Pro Lys Arg Gly Pro Gln
 65                  70                  75                  80

Ala Phe Asp Ala Phe Cys Glu Ala Leu Arg Glu Thr Lys Gln Gly His
                 85                  90                  95

Leu Glu Asp Met Leu Leu Thr Thr Leu Ser Gly Leu Gln His Val Leu
            100                 105                 110

Pro Pro Leu Ser Cys Asp Tyr Asp Leu Ser Leu Pro Phe Pro Val Cys
            115                 120                 125

Glu Ser Cys Pro Leu Tyr Lys Lys Leu Arg Leu Ser Thr Asp Thr Val
130                 135                 140

Glu His Ser Leu Asp Asn Lys Asp Gly Pro Val Cys Leu Gln Val Lys
145                 150                 155                 160

Pro Cys Thr Pro Glu Phe Tyr Gln Thr His Phe Gln Leu Ala Tyr Arg
                165                 170                 175

Leu Gln Ser Arg Pro Arg Gly Leu Ala Leu Val Leu Ser Asn Val His
            180                 185                 190

Phe Thr Gly Glu Lys Glu Leu Glu Phe Arg Ser Gly Gly Asp Val Asp
            195                 200                 205

His Ser Thr Leu Val Thr Leu Phe Lys Leu Leu Gly Tyr Asp Val His
210                 215                 220

Val Leu Cys Asp Gln Thr Ala Gln Val Met Gln Glu Lys Leu Gln Asn
225                 230                 235                 240

Phe Ala Gln Leu Pro Ala His Arg Val Thr Asp Ser Cys Ile Val Ala
                245                 250                 255

Leu Leu Ser His Gly Val Glu Gly Ala Ile Tyr Gly Val Asp Gly Lys
            260                 265                 270

Leu Leu Gln Leu Gln Glu Val Phe Gln Leu Phe Asp Asn Ala Asn Cys
            275                 280                 285

Pro Ser Leu Gln Asn Lys Pro Lys Met Phe Phe Ile Gln Ala Cys Arg
            290                 295                 300

Gly Asp Glu Thr Asp Arg Gly Val Asp Gln Gln Asp Gly Lys Asn His
305                 310                 315                 320

Ala Gly Ser Pro Gly Cys Glu Glu Ser Asp Ala Gly Lys Glu Lys Leu
                325                 330                 335

Pro Lys Met Arg Leu Pro Thr Arg Ser Asp Met Ile Cys Gly Tyr Ala
            340                 345                 350

Cys Leu Lys Gly Thr Ala Ala Met Arg Asn Thr Lys Arg Gly Ser Trp
            355                 360                 365
```

```
Tyr Ile Glu Ala Leu Ala Gln Val Phe Ser Glu Arg Ala Cys Asp Met
    370                 375                 380

His Val Ala Asp Met Leu Val Lys Lys Asn Ala Leu Ile Lys Asp Arg
385                 390                 395                 400

Glu Gly Tyr Ala Pro Gly Thr Glu Phe His Arg Cys Lys Glu Met Ser
                405                 410                 415

Glu Tyr Cys Ser Thr Leu Cys Arg His Leu Tyr Leu Phe Pro Gly His
            420                 425                 430

Pro Pro Thr
        435

<210> SEQ ID NO 11
<211> LENGTH: 277
<212> TYPE: PRT
<213> ORGANISM: Unknown
<220> FEATURE:
<223> OTHER INFORMATION: Description of Unknown Organism: Caspase-3

<400> SEQUENCE: 11

Met Glu Asn Thr Glu Asn Ser Val Asp Ser Lys Ser Ile Lys Asn Leu
 1               5                  10                  15

Glu Pro Lys Ile Ile His Gly Ser Glu Ser Met Asp Ser Gly Ile Ser
                20                  25                  30

Leu Asp Asn Ser Tyr Lys Met Asp Tyr Pro Glu Met Gly Leu Cys Ile
            35                  40                  45

Ile Ile Asn Asn Lys Asn Phe His Lys Ser Thr Gly Asn Thr Ser Arg
        50                  55                  60

Ser Gly Thr Asp Val Asp Ala Ala Asn Leu Arg Glu Thr Phe Arg Asn
 65                 70                  75                  80

Leu Lys Tyr Glu Val Arg Asn Lys Asn Asp Leu Thr Arg Lys Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Lys Glu Gly Ile Ile Phe
        115                 120                 125

Gly Thr Asn Gly Pro Val Asp Leu Lys Lys Ile Thr Asn Phe Phe Arg
130                 135                 140

Gly Asp Arg Cys Arg Ser Leu Thr Gly Lys Pro Lys Leu Phe Ile Ile
145                 150                 155                 160

Gln Ala Cys Arg Gly Thr Lys Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
210                 215                 220

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
                245                 250                 255

His Ala Lys Lys Gln Ile Pro Cys Ile Val Ser Met Leu Thr Lys Glu
            260                 265                 270

Leu Tyr Phe Tyr His
        275
```

```
<210> SEQ ID NO 12
<211> LENGTH: 503
<212> TYPE: PRT
<213> ORGANISM: Caenorhabditis elegans

<400> SEQUENCE: 12
```

| | | | | | | | | | | | | | | |
|---|---|---|---|---|---|---|---|---|---|---|---|---|---|---|
| Met | Met | Arg | Gln | Asp | Arg | Arg | Ser | Leu | Leu | Glu | Arg | Asn | Ile | Met | Met |
| 1 | | | | 5 | | | | | 10 | | | | | 15 | |

| Phe | Ser | Ser | His | Leu | Lys | Val | Asp | Glu | Ile | Leu | Glu | Val | Leu | Ile | Ala |
| | | | 20 | | | | | 25 | | | | | 30 | | |

| Lys | Gln | Val | Leu | Asn | Ser | Asp | Asn | Gly | Asp | Asn | Ile | Asn | Ser | Cys | Gly |
| | | 35 | | | | | 40 | | | | | 45 | | | |

| Thr | Val | Arg | Glu | Lys | Arg | Arg | Glu | Ile | Val | Lys | Ala | Val | Gln | Arg | Arg |
| | 50 | | | | | 55 | | | | | 60 | | | | |

| Gly | Asp | Val | Ala | Phe | Asp | Ala | Phe | Tyr | Asp | Ala | Leu | Arg | Ser | Thr | Gly |
| 65 | | | | | 70 | | | | | 75 | | | | | 80 |

| His | Glu | Gly | Leu | Ala | Glu | Val | Leu | Glu | Pro | Leu | Ala | Arg | Ser | Val | Asp |
| | | | | 85 | | | | | 90 | | | | | 95 | |

| Ser | Asn | Ala | Val | Glu | Phe | Glu | Cys | Pro | Met | Ser | Pro | Ala | Ser | His | Arg |
| | | | 100 | | | | | 105 | | | | | 110 | | |

| Arg | Ser | Arg | Ala | Leu | Ser | Pro | Ala | Gly | Tyr | Thr | Ser | Pro | Thr | Arg | Val |
| | | 115 | | | | | 120 | | | | | 125 | | | |

| His | Arg | Asp | Ser | Val | Ser | Ser | Val | Ser | Ser | Phe | Thr | Ser | Tyr | Gln | Asp |
| | 130 | | | | | 135 | | | | | 140 | | | | |

| Ile | Tyr | Ser | Arg | Ala | Arg | Ser | Arg | Ser | Arg | Ser | Arg | Ala | Leu | His | Ser |
| 145 | | | | | 150 | | | | | 155 | | | | | 160 |

| Ser | Asp | Arg | His | Asn | Tyr | Ser | Ser | Pro | Pro | Val | Asn | Ala | Phe | Pro | Ser |
| | | | | 165 | | | | | 170 | | | | | 175 | |

| Gln | Pro | Ser | Ser | Ala | Asn | Ser | Ser | Phe | Thr | Gly | Cys | Ser | Ser | Leu | Gly |
| | | | 180 | | | | | 185 | | | | | 190 | | |

| Tyr | Ser | Ser | Arg | Asn | Arg | Ser | Phe | Ser | Lys | Ala | Ser | Gly | Pro | Thr |
| | | 195 | | | | | 200 | | | | | 205 | | | |

| Gln | Tyr | Ile | Phe | His | Glu | Glu | Asp | Met | Asn | Phe | Val | Asp | Ala | Pro | Thr |
| | 210 | | | | | 215 | | | | | 220 | | | | |

| Ile | Ser | Arg | Val | Phe | Asp | Glu | Lys | Thr | Met | Tyr | Arg | Asn | Phe | Ser | Ser |
| 225 | | | | | 230 | | | | | 235 | | | | | 240 |

| Pro | Arg | Gly | Met | Cys | Leu | Ile | Ile | Asn | Asn | Glu | His | Phe | Glu | Gln | Met |
| | | | | 245 | | | | | 250 | | | | | 255 | |

| Pro | Thr | Arg | Asn | Gly | Thr | Lys | Ala | Asp | Lys | Asp | Asn | Leu | Thr | Asn | Leu |
| | | | 260 | | | | | 265 | | | | | 270 | | |

| Phe | Arg | Cys | Met | Gly | Tyr | Thr | Val | Ile | Cys | Lys | Asp | Asn | Leu | Thr | Gly |
| | | 275 | | | | | 280 | | | | | 285 | | | |

| Arg | Gly | Met | Leu | Leu | Thr | Ile | Arg | Asp | Phe | Ala | Lys | His | Glu | Ser | His |
| | 290 | | | | | 295 | | | | | 300 | | | | |

| Gly | Asp | Ser | Ala | Ile | Leu | Val | Ile | Leu | Ser | His | Gly | Lys | Glu | Asn | Val |
| 305 | | | | | 310 | | | | | 315 | | | | | 320 |

| Ile | Ile | Gly | Val | Asp | Asp | Ile | Pro | Ile | Ser | Thr | His | Glu | Ile | Tyr | Asp |
| | | | | 325 | | | | | 330 | | | | | 335 | |

| Leu | Leu | Asn | Ala | Ala | Asn | Ala | Pro | Arg | Leu | Ala | Asn | Lys | Pro | Lys | Ile |
| | | | 340 | | | | | 345 | | | | | 350 | | |

| Val | Phe | Val | Gln | Ala | Cys | Arg | Gly | Glu | Arg | Arg | Asp | Asn | Gly | Phe | Pro |
| | | 355 | | | | | 360 | | | | | 365 | | | |

| Val | Leu | Asp | Ser | Val | Asp | Gly | Val | Pro | Ala | Phe | Leu | Arg | Arg | Gly | Trp |
| | 370 | | | | | 375 | | | | | 380 | | | | |

```
Asp Asn Arg Asp Gly Pro Leu Phe Asn Phe Leu Gly Cys Val Arg Pro
385                 390                 395                 400

Gln Val Gln Gln Val Trp Arg Lys Lys Pro Ser Gln Ala Asp Ile Leu
            405                 410                 415

Ile Ala Tyr Ala Thr Thr Ala Gly Ile Val Ser Trp Arg Asn Ser Ala
            420                 425                 430

Arg Gly Ser Trp Phe Ile Gln Ala Val Cys Glu Val Phe Ser Thr His
            435                 440                 445

Ala Lys Asp Met Asp Val Val Glu Leu Leu Thr Glu Val Asn Lys Lys
    450                 455                 460

Val Ala Cys Gly Phe Gln Thr Ser Gln Gly Ser Asn Ile Leu Lys Gln
465                 470                 475                 480

Met Pro Glu Met Thr Ser Arg Leu Leu Lys Lys Phe Tyr Pro Trp Pro
            485                 490                 495

Glu Ala Arg Asn Ser Ala Val
            500

<210> SEQ ID NO 13
<211> LENGTH: 1050
<212> TYPE: DNA
<213> ORGANISM: Artificial Sequence
<220> FEATURE:
<221> NAME/KEY: CDS
<222> LOCATION: (1)..(1047)
<220> FEATURE:
<223> OTHER INFORMATION: Description of Artificial Sequence: Caspase-12S
      cDNA

<400> SEQUENCE: 13 atg gcg gcc agg agg aca cat gaa aga gat cca atc tac aag atc aaa        48
Met Ala Ala Arg Arg Thr His Glu Arg Asp Pro Ile Tyr Lys Ile Lys
  1               5                  10                  15 gaa ttt tct aat gat gag gat gat gga cct cag aag ata tgt aca cct        96
Glu Phe Ser Asn Asp Glu Asp Asp Gly Pro Gln Lys Ile Cys Thr Pro
                 20                  25                  30 tct tct cca tca gaa tcc aag aga aaa gta gag gat gat gaa atg gag       144
Ser Ser Pro Ser Glu Ser Lys Arg Lys Val Glu Asp Asp Glu Met Glu
             35                  40                  45 gta aat gct gga ttg gcc cat gaa tca cat cta atg ctg aca gct cct       192
Val Asn Ala Gly Leu Ala His Glu Ser His Leu Met Leu Thr Ala Pro
         50                  55                  60 cat gga ctc cag agc tca gaa gtc caa gat aca ctg aag ctt tgt cca       240
His Gly Leu Gln Ser Ser Glu Val Gln Asp Thr Leu Lys Leu Cys Pro
 65                  70                  75                  80 cgt gat cag ttt tgt aag ata aag aca gaa agg gca aaa gag ata tat       288
Arg Asp Gln Phe Cys Lys Ile Lys Thr Glu Arg Ala Lys Glu Ile Tyr
                 85                  90                  95 cca gtg atg gag aag gag gga cga aca cgt ctg gct ctc atc atc tgc       336
Pro Val Met Glu Lys Glu Gly Arg Thr Arg Leu Ala Leu Ile Ile Cys
                100                 105                 110 aac aaa aag ttt gac tac ctt ttt gat aga gat aat gct gat act gac       384
Asn Lys Lys Phe Asp Tyr Leu Phe Asp Arg Asp Asn Ala Asp Thr Asp
            115                 120                 125 att ttg aac atg caa gaa cta ctt gaa aat ctt gga tac tct gtg gtg       432
Ile Leu Asn Met Gln Glu Leu Leu Glu Asn Leu Gly Tyr Ser Val Val
        130                 135                 140 tta aaa gaa aac ctt aca gct cag gaa atg gag aca gag tta atg cag       480
Leu Lys Glu Asn Leu Thr Ala Gln Glu Met Glu Thr Glu Leu Met Gln
145                 150                 155                 160
```

```
ttt gct ggc cgt cca gag cac cag tcc tca gac agc aca ttc ctg gtg        528
Phe Ala Gly Arg Pro Glu His Gln Ser Ser Asp Ser Thr Phe Leu Val
                165                 170                 175 ttt atg tcc cat ggc atc ctg gaa gga atc tgt ggg gtg aag cac cga        576
Phe Met Ser His Gly Ile Leu Glu Gly Ile Cys Gly Val Lys His Arg
            180                 185                 190 aac aaa aag cca gat gtt ctt cat gat gac act atc ttc aaa att ttc        624
Asn Lys Lys Pro Asp Val Leu His Asp Asp Thr Ile Phe Lys Ile Phe
        195                 200                 205 aac aac tct aac tgt cgg agt ctg aga aac aaa ccc aag att ctc atc        672
Asn Asn Ser Asn Cys Arg Ser Leu Arg Asn Lys Pro Lys Ile Leu Ile
    210                 215                 220 atg cag gcc tgc aga ggc aga tat aat gga act att tgg gta tcc aca        720
Met Gln Ala Cys Arg Gly Arg Tyr Asn Gly Thr Ile Trp Val Ser Thr
225                 230                 235                 240 aac aaa ggg ata gcc act gct gat aca gat gag gaa cgt gtg ttg agc        768
Asn Lys Gly Ile Ala Thr Ala Asp Thr Asp Glu Glu Arg Val Leu Ser
                245                 250                 255 tgt aaa tgg aat aat agt ata aca aag gcc cat gtg gag aca gat ttc        816
Cys Lys Trp Asn Asn Ser Ile Thr Lys Ala His Val Glu Thr Asp Phe
            260                 265                 270 att gct ttc aaa tct tct acc cca cat aat att tct tgg aag gta ggc        864
Ile Ala Phe Lys Ser Ser Thr Pro His Asn Ile Ser Trp Lys Val Gly
        275                 280                 285 aag act ggt tcc ctc ttc att tcc aaa ctc att gac tgc ttc aaa aag        912
Lys Thr Gly Ser Leu Phe Ile Ser Lys Leu Ile Asp Cys Phe Lys Lys
    290                 295                 300 tac tgt tgg tgt tat cat ttg gag gaa att ttt cga aag gtt caa cac        960
Tyr Cys Trp Cys Tyr His Leu Glu Glu Ile Phe Arg Lys Val Gln His
305                 310                 315                 320 tca ttt gag gtc cca ggt gaa ctg acc cag atg ccc act att gag aga       1008
Ser Phe Glu Val Pro Gly Glu Leu Thr Gln Met Pro Thr Ile Glu Arg
                325                 330                 335 gta tcc atg aca cgc tat ttc tac ctt ttt ccc ggg aat tag              1050
Val Ser Met Thr Arg Tyr Phe Tyr Leu Phe Pro Gly Asn
                340                 345
```

<210> SEQ ID NO 14
<211> LENGTH: 349
<212> TYPE: PRT
<213> ORGANISM: Artificial Sequence
<220> FEATURE:
<223> OTHER INFORMATION: Description of Artificial Sequence: Caspase-12S
       protein

<400> SEQUENCE: 14

```
Met Ala Ala Arg Arg Thr His Glu Arg Asp Pro Ile Tyr Lys Ile Lys
  1               5                  10                  15

Glu Phe Ser Asn Asp Glu Asp Asp Gly Pro Gln Lys Ile Cys Thr Pro
                 20                  25                  30

Ser Ser Pro Ser Glu Ser Lys Arg Lys Val Glu Asp Asp Glu Met Glu
             35                  40                  45

Val Asn Ala Gly Leu Ala His Glu Ser His Leu Met Leu Thr Ala Pro
         50                  55                  60

His Gly Leu Gln Ser Ser Glu Val Gln Asp Thr Leu Lys Leu Cys Pro
 65                  70                  75                  80

Arg Asp Gln Phe Cys Lys Ile Lys Thr Glu Arg Ala Lys Glu Ile Tyr
                 85                  90                  95

Pro Val Met Glu Lys Glu Gly Arg Thr Arg Leu Ala Leu Ile Ile Cys
            100                 105                 110
```

-continued

```
Asn Lys Lys Phe Asp Tyr Leu Phe Asp Arg Asp Asn Ala Asp Thr Asp
            115                 120                 125

Ile Leu Asn Met Gln Glu Leu Leu Glu Asn Leu Gly Tyr Ser Val Val
        130                 135                 140

Leu Lys Glu Asn Leu Thr Ala Gln Glu Met Glu Thr Glu Leu Met Gln
145                 150                 155                 160

Phe Ala Gly Arg Pro Glu His Gln Ser Ser Asp Ser Thr Phe Leu Val
                165                 170                 175

Phe Met Ser His Gly Ile Leu Glu Gly Ile Cys Gly Val Lys His Arg
            180                 185                 190

Asn Lys Lys Pro Asp Val Leu His Asp Asp Thr Ile Phe Lys Ile Phe
        195                 200                 205

Asn Asn Ser Asn Cys Arg Ser Leu Arg Asn Lys Pro Lys Ile Leu Ile
    210                 215                 220

Met Gln Ala Cys Arg Gly Arg Tyr Asn Gly Thr Ile Trp Val Ser Thr
225                 230                 235                 240

Asn Lys Gly Ile Ala Thr Ala Asp Thr Asp Glu Glu Arg Val Leu Ser
                245                 250                 255

Cys Lys Trp Asn Asn Ser Ile Thr Lys Ala His Val Glu Thr Asp Phe
            260                 265                 270

Ile Ala Phe Lys Ser Ser Thr Pro His Asn Ile Ser Trp Lys Val Gly
        275                 280                 285

Lys Thr Gly Ser Leu Phe Ile Ser Lys Leu Ile Asp Cys Phe Lys Lys
    290                 295                 300

Tyr Cys Trp Cys Tyr His Leu Glu Glu Ile Phe Arg Lys Val Gln His
305                 310                 315                 320

Ser Phe Glu Val Pro Gly Glu Leu Thr Gln Met Pro Thr Ile Glu Arg
                325                 330                 335

Val Ser Met Thr Arg Tyr Phe Tyr Leu Phe Pro Gly Asn
            340                 345

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: DNA Primer
<220> FEATURE:
<221> NAME/KEY: unsure
<222> LOCATION: (3)
<223> OTHER INFORMATION: May be any nucleic acid
<220> FEATURE:
<221> NAME/KEY: unsure
<222> LOCATION: (6)
<223> OTHER INFORMATION: May be any nucleic acid
<220> FEATURE:
<221> NAME/KEY: unsure
<222> LOCATION: (12)
<223> OTHER INFORMATION: May be any nucleic acid

<400> SEQUENCE: 15
tgnccnggga anaggtagaa                                                      20

<210> SEQ ID NO 16
<211> LENGTH: 23
<212> TYPE: DNA
<213> ORGANISM: Artificial Sequence
<220> FEATURE:
<221> NAME/KEY: unsure
<222> LOCATION: (6)
<223> OTHER INFORMATION: May be adenine, thymine or cytosine
```

```
<220> FEATURE:
<223> OTHER INFORMATION: Description of Artificial Sequence: DNA Primer
<220> FEATURE:
<221> NAME/KEY: unsure
<222> LOCATION: (15)
<223> OTHER INFORMATION: May be any nucleic acid

<400> SEQUENCE: 16
atcatnatcc aggcntgcag rgg                                              23

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: DNA Primer

<400> SEQUENCE: 17

Phe Tyr Leu Phe Pro Gly
 1               5

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: DNA Primer

<400> SEQUENCE: 18
gagatccaat ctacaagatc                                                  20

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: DNA Primer

<400> SEQUENCE: 19
caccacagag tatccaag                                                    18

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: DNA Primer

<400> SEQUENCE: 20
ctcgaattca tggcggccag gaggacacat g                                     31

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: DNA Primer

<400> SEQUENCE: 21
ctcggatcct tcccgggaaa aggtag                                           26

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: DNA Primer
```

<400> SEQUENCE: 22
ctcggtacca tgggacctca gaagatatgt ac                                    32

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: DNA Primer

<400> SEQUENCE: 23
ctcgtcgacc cattcccggg aaaaaggtag                                       30

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: DNA Primer

<400> SEQUENCE: 24
ctggatccgt atggcggcca ggaggacaca tgaaagagat cc                         42

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: DNA Primer

<400> SEQUENCE: 25
ctcgtcgacc cattcccggg aaaaaggtag                                       30

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: DNA Primer

<400> SEQUENCE: 26
ctcctcgagc taattcccgg gaaaaagg                                         28

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: DNA Primer

<400> SEQUENCE: 27
ctcggatccg gacctcagaa gatatgtac                                        29

<210> SEQ ID NO 28
<211> LENGTH: 31
<212> TYPE: DNA
<213> ORGANISM: Artificial Sequence
<220> FEATURE:
<223> OTHER INFORMATION: Description of Artificial Sequence: DNA Primer

<400> SEQUENCE: 28
ctcggatccc taattcccgg gaaaaaggta g                                     31

<210> SEQ ID NO 29

```
<211> LENGTH: 29
<212> TYPE: DNA
<213> ORGANISM: Artificial Sequence
<220> FEATURE:
<223> OTHER INFORMATION: Description of Artificial Sequence: DNA Primer

<400> SEQUENCE: 29
ctcggatcca cactgaagct ttgtccacg                                        29

<210> SEQ ID NO 30
<211> LENGTH: 4
<212> TYPE: PRT
<213> ORGANISM: Unknown
<220> FEATURE:
<221> NAME/KEY: UNSURE
<222> LOCATION: (2)..(3)
<223> OTHER INFORMATION: May be any amino acid

<400> SEQUENCE: 30

Asp Xaa Xaa Asp
 1

<210> SEQ ID NO 31
<211> LENGTH: 13
<212> TYPE: PRT
<213> ORGANISM: Unknown
<220> FEATURE:
<223> OTHER INFORMATION: Description of Unknown Organism: ICE

<400> SEQUENCE: 31

His Gly Cys Arg Gln Arg Ser Val Trp His Pro Arg Gln
 1               5                  10

<210> SEQ ID NO 32
<211> LENGTH: 13
<212> TYPE: PRT
<213> ORGANISM: Unknown
<220> FEATURE:
<223> OTHER INFORMATION: Description of Unknown Organism: Caspase-12

<400> SEQUENCE: 32

His Gly Cys Arg Gln Lys Ser Ile Trp Val Gly Leu Gln
 1               5                  10

<210> SEQ ID NO 33
<211> LENGTH: 13
<212> TYPE: PRT
<213> ORGANISM: Unknown
<220> FEATURE:
<223> OTHER INFORMATION: Description of Unknown Organism: Caspase-11

<400> SEQUENCE: 33

His Gly Cys Arg Gln Arg Ser Leu Tyr Asp Lys His Gln
 1               5                  10

<210> SEQ ID NO 34
<211> LENGTH: 13
<212> TYPE: PRT
<213> ORGANISM: Unknown
<220> FEATURE:
<223> OTHER INFORMATION: Description of Unknown Organism: Caspase-2

<400> SEQUENCE: 34

His Gly Cys Arg Gln Arg Ser Ala Met Asn Thr Tyr Pro
 1               5                  10

<210> SEQ ID NO 35
```

```
<211> LENGTH: 13
<212> TYPE: PRT
<213> ORGANISM: Unknown
<220> FEATURE:
<223> OTHER INFORMATION: Description of Unknown Organism: Caspase-3

<400> SEQUENCE: 35

His Gly Cys Arg Gln Arg Ser Tyr Trp Asn Ser Phe Phe
 1               5                  10

<210> SEQ ID NO 36
<211> LENGTH: 4
<212> TYPE: PRT
<213> ORGANISM: Artificial Sequence
<220> FEATURE:
<223> OTHER INFORMATION: Description of Artificial Sequence: Peptide
      Inhibitor

<400> SEQUENCE: 36

Tyr Val Ala Asp
 1

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Peptide
      Inhibitor

<400> SEQUENCE: 37

Asp Glu Val Asp
 1

<210> SEQ ID NO 38
<211> LENGTH: 5
<212> TYPE: PRT
<213> ORGANISM: Unknown
<220> FEATURE:
<223> OTHER INFORMATION: Description of Unknown Organism: Pro-caspase-12

<400> SEQUENCE: 38

Asp Glu Asp Asp Gly
 1               5
```